(12) United States Patent
Inoue et al.

(10) Patent No.: US 8,048,540 B2
(45) Date of Patent: Nov. 1, 2011

(54) ORGANOMETALLIC COMPLEX, AND LIGHT-EMITTING ELEMENT, LIGHT-EMITTING DEVICE AND ELECTRONIC DEVICE INCLUDING THE ORGANOMETALLIC COMPLEX

(75) Inventors: Hideko Inoue, Atsugi (JP); Satoshi Seo, Kawasaki (JP); Nobuharu Ohsawa, Zama (JP)

(73) Assignee: Semiconductor Energy Laboratory Co., Ltd., Atsugi-shi, Kanagawa-ken (JP)

( * ) Notice: Subject to any disclaimer, the term of this patent is extended or adjusted under 35 U.S.C. 154(b) by 978 days.

(21) Appl. No.: 12/003,438

(22) Filed: Dec. 26, 2007

(65) Prior Publication Data

US 2008/0160345 A1 Jul. 3, 2008

(30) Foreign Application Priority Data

Dec. 27, 2006 (JP) ................. 2006-350895
Nov. 19, 2007 (JP) ................. 2007-299175

(51) Int. Cl.
*H01L 51/54* (2006.01)
*C09K 11/06* (2006.01)
*C07D 241/36* (2006.01)

(52) U.S. Cl. . 428/690; 428/917; 313/504; 257/E51.044; 544/225

(58) Field of Classification Search .................. None
See application file for complete search history.

(56) References Cited

U.S. PATENT DOCUMENTS

| 7,238,806 | B2 | 7/2007 | Inoue et al. |
| 2003/0059646 | A1 | 3/2003 | Kamatani et al. |
| 2003/0068526 | A1 | 4/2003 | Kamatani et al. |
| 2006/0159955 | A1 | 7/2006 | Inoue et al. |
| 2007/0034854 | A1 | 2/2007 | Inoue et al. |
| 2007/0191587 | A1 | 8/2007 | Kanitz et al. |
| 2007/0241667 | A1 | 10/2007 | Ohsawa et al. |
| 2007/0244320 | A1 | 10/2007 | Inoue et al. |
| 2009/0322217 | A1 | 12/2009 | Inoue et al. |

FOREIGN PATENT DOCUMENTS

| EP | 1873163 A | 1/2008 |
| EP | 1939208 A | 7/2008 |
| JP | 2005-298483 | 10/2005 |
| JP | 2006-151887 | 6/2006 |
| JP | 2007-091718 A | 4/2007 |
| JP | 2007-522271 | 8/2007 |
| JP | 2007-284432 A | 11/2007 |
| JP | 2008-179607 A | 8/2008 |
| WO | WO 2006/059802 | 6/2006 |
| WO | WO 2006-062144 | 6/2006 |
| WO | WO-2009/100991 | 8/2009 |
| WO | WO-2009/157498 | 12/2009 |

OTHER PUBLICATIONS

Machine translation of JP 2005-298483 (Oct. 2005).*
Search Report (Application No. 07024831.5) dated Mar. 26, 2008.
Jiun-Pey Duan et al., *New Iridium Complexes as Highly Efficient Orange-Red Emitters in Organic Light-Emitting Diodes*, Advanced Materials, vol. 15, No. 3, 2003, pp. 224-228.
Peter J. Steel et al., *Cyclometallated Compounds V. Double Cyclopalladation of Diphenyl Pyrazines and Related Ligands*, Journal of Organometallic Chemistry, 395, 1990, pp. 359-373.
Written Opinion (Application No. PCT/JP2009/061546) Dated Jul. 28, 2009.
International Search Report (Application No. PCT/JP2009/061546) Dated Jul. 28, 2009.

* cited by examiner

*Primary Examiner* — Marc R. Yamnitzky
(74) *Attorney, Agent, or Firm* — Eric J. Robinson; Robinson Intellectual Property Law Office, P.C.

(57) ABSTRACT

An organometallic complex with high emission efficiency and an organic light-emitting element having the organometallic complex are described. The organometallic complex has a structure represented by the following general formula (G1').

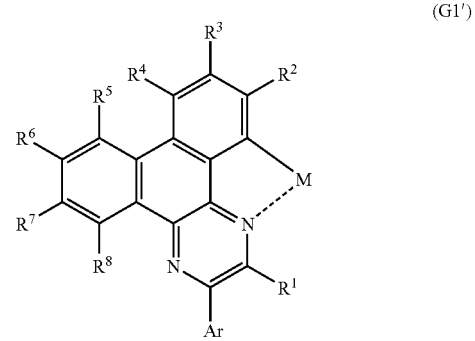

(G1')

31 Claims, 26 Drawing Sheets

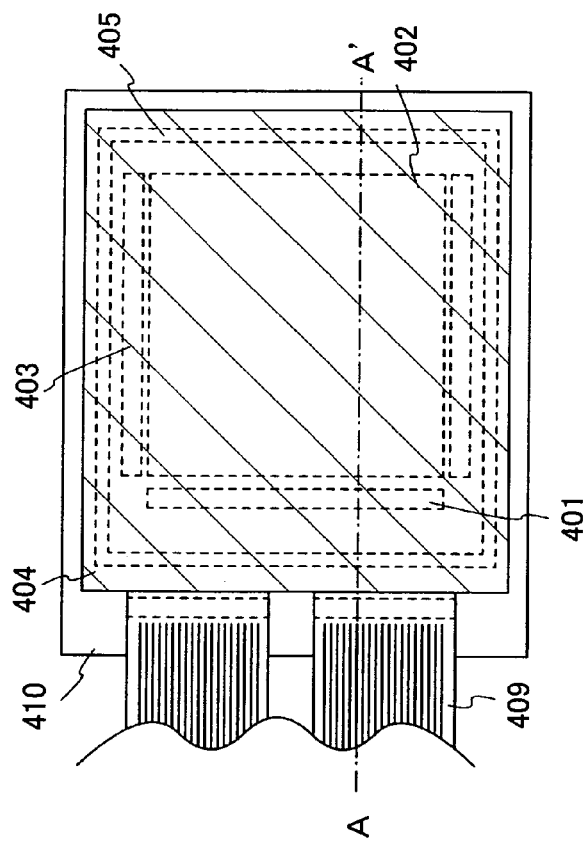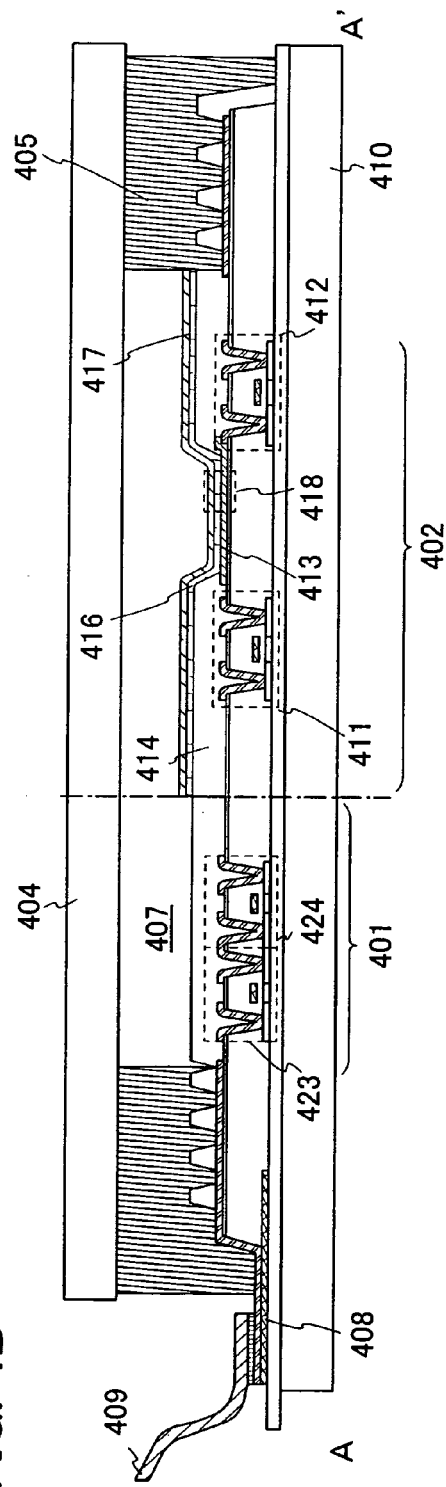
FIG. 4A
FIG. 4B

ORGANOMETALLIC COMPLEX, AND LIGHT-EMITTING ELEMENT, LIGHT-EMITTING DEVICE AND ELECTRONIC DEVICE INCLUDING THE ORGANOMETALLIC COMPLEX

BACKGROUND OF THE INVENTION

1. Field of the Invention

The present invention relates to an organometallic complex. In particular, the present invention relates to an organometallic complex that is capable of converting a triplet excited state into luminescence. Furthermore, the present invention relates to a light-emitting element, a light-emitting device, and an electronic device that include the organometallic complex.

2. Description of the Related Art

Organic compounds are brought into an excited state by the absorption of light. Through this excited state, various reactions (photochemical reactions) are caused in some cases, or luminescence is generated in some cases. Therefore, various applications of the organic compounds are made.

As one example of the photochemical reactions, a reaction of singlet oxygen with an unsaturated organic molecule (oxygen addition) is known (refer to Reference 1: Haruo INOUE, et al., Basic Chemistry Course PHOTOCHEMISTRY I (Maruzen Co., Ltd.), pp. 106-110, for example). Since the ground state of an oxygen molecule is a triplet state, oxygen in a singlet state (singlet oxygen) is not generated by direct photoexcitation. However, in the presence of another triplet excited molecule, singlet oxygen is generated to cause an oxygen addition reaction. In this case, a compound capable of forming a triplet excited molecule is referred to as a photosensitizer.

As described above, generation of singlet oxygen requires a photosensitizer capable of forming a triplet excited state by photoexcitation. However, the ground state of an ordinary organic compound is a singlet state; therefore, photoexcitation to a triplet excited state is forbidden transition and generation of a triplet excited molecule is difficult. A compound that can easily cause intersystem crossing from the singlet excited state to the triplet excited state (or a compound that allows the forbidden transition of photoexcitation directly to the triplet excited state) is thus required as such a photosensitizer. In other words, such a compound can be used as the photosensitizer and is useful.

The above compound often exhibits phosphorescence. Phosphorescence refers to luminescence generated by transition between different energies in multiplicity. In an ordinary organic compound, phosphorescence refers to luminescence generated in returning from the triplet excited state to the singlet ground state (in contrast, fluorescence refers to luminescence in returning from the singlet excited state to the singlet ground state). Application fields of a compound capable of exhibiting phosphorescence, that is, a compound capable of converting the triplet excited state into luminescence (hereinafter, referred to as a phosphorescent compound), include a light-emitting element including an organic compound as a light-emitting substance.

This light-emitting element has a simple structure in which a light-emitting layer including an organic compound that is a light-emitting substance is provided between electrodes. This light-emitting element attracts attention as a next-generation flat panel display element in terms of characteristics such as being thin and light in weight, high speed response, and direct current low voltage driving. Further, a display device including this light-emitting element is superior in contrast, image quality, and wide viewing angle.

The light-emitting element including an organic compound as a light-emitting substance has a mechanism of light emission that is carrier injection: voltage is applied between electrodes where a light-emitting layer is interposed, electrons and holes injected from the electrodes are recombined to make the light-emitting substance excited, and then light is emitted in returning from the excited state to the ground state. As in the case of photoexcitation described above, types of the excited state include a singlet excited state (S*) and a triplet excited state (T*). The statistical generation ratio thereof in the light-emitting element is considered to be S*:T*=1:3.

At room temperature, a compound capable of converting a singlet excited state to luminescence (hereinafter, referred to as a fluorescent compound) exhibits only luminescence from the singlet excited state (fluorescence), not luminescence from the triplet excited state (phosphorescence). Accordingly, the internal quantum efficiency (the ratio of generated photons to injected carriers) of a light-emitting element including the fluorescent compound is assumed to have a theoretical limit of 25% based on S*:T*=1:3.

On the other hand, in a case of a light-emitting element including the phosphorescent compound described above, the internal quantum efficiency thereof can be improved to 75 to 100% in theory; namely, the emission efficiency thereof can be 3 to 4 times as much as that of the light-emitting element including a fluorescent compound. Therefore, the light-emitting element including a phosphorescent compound has been actively developed in recent years in order to achieve a highly-efficient light-emitting element, (for example, refer to Reference 2: Jiun-Pey Duan, et al., "New Iridium Complexes as Highly Efficient Orange-Red Emitters in Organic Light-Emitting Diodes", Advanced Materials, vol. 15, No. 3, 2003, pp. 224-228). An organometallic complex that contains iridium or the like as a central metal is particularly attracting attention as a phosphorescent compound because of its high phosphorescence quantum efficiency.

SUMMARY OF THE INVENTION

An organometallic complex such as the organometallic complex disclosed in Reference 2 can be expected to be used as the photosensitizer because of its ease of causing intersystem crossing. Further, because of its ease of exhibiting luminescence (phosphorescence) from a triplet excited state, application of the organometallic complex to a light-emitting element raises expectations for a highly-efficient light-emitting element. However, in the present state, there are small number of kinds of such an organometallic complex.

The organometallic complex disclosed in Reference 2 emits orange-red light, which makes the purity of red color poor; accordingly, this organometallic complex is disadvantage in color reproducibility for application to a full-color display or the like. In contrast, in a case of an organometallic complex that emits dark red light, that is, light having an extremely long emission wavelength, although the organometallic complex is advantageous in terms of color reproducibility, the luminous efficiency (cd/A) thereof decreases.

Accordingly, it is an object of the present invention to provide an organometallic complex that can emit red light. Further, it is an object of the present invention to provide an organometallic complex having high emission efficiency. Moreover, it is an object of the present invention to provide an organometallic complex that can emit red light with high luminous efficiency.

Further, it is an object of the present invention to provide a light-emitting element having high emission efficiency. Furthermore, it is an object of the present invention to provide a light-emitting element that can emit red light with high luminous efficiency. Moreover, it is an object of the present invention to provide a light-emitting element capable of long-time driving.

Furthermore, it is an object of the present invention to provide a light-emitting device and an electronic device with low power consumption.

The present inventors have earnestly made researches in order to achieve the above objects. Consequently, the present inventors have found that a dibenzo[f,h]quinoxaline derivative represented by the following general formula (G0) can form an organometallic complex by its ortho-metalation with a metal ion of Group 9 or Group 10 of the periodic table. Further, the present inventors have also found that the organometallic complex tends to cause intersystem crossing and can efficiently exhibit phosphorescence. Furthermore, the present inventors have found that the organometallic complex emits favorable red-color light. Moreover, they have found that a light-emitting element including the organometallic complex can achieve a capability for long-time driving.

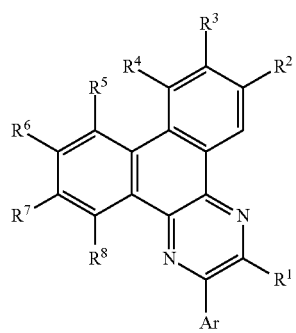

(G0)

In the formula, Ar represents an aryl group having 6 to 25 carbon atoms; $R^1$ is any one of hydrogen, an alkyl group having 1 to 4 carbon atoms, and an alkoxy group having 1 to 4 carbon atoms; $R^2$ to $R^8$ each represent any one of hydrogen, an alkyl group having 1 to 4 carbon atoms, an alkoxy group having 1 to 4 carbon atoms, and a halogen group; and at least one of pairs $R^3$ and $R^4$, $R^4$ and $R^5$, and $R^5$ and $R^6$ may be bound to each other to form a ring.

Accordingly, one aspect of the present invention is to provide an organometallic complex having a partial structure represented by the following general formula (G1').

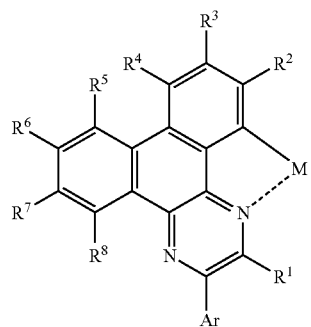

(G1')

In the formula, Ar represents an aryl group having 6 to 25 carbon atoms; $R^1$ is any one of hydrogen, an alkyl group having 1 to 4 carbon atoms, and an alkoxy group having 1 to 4 carbon atoms; $R^2$ to $R^8$ each represent any one of hydrogen, an alkyl group having 1 to 4 carbon atoms, an alkoxy group having 1 to 4 carbon atoms, and a halogen group; at least one of pairs $R^3$ and $R^4$, $R^4$ and $R^5$, and $R^5$ and $R^6$ may be bound to each other to form a ring; and M is a central metal of Group 9 elements and Group 10 elements.

$R^1$ in the dibenzo[f,h]quinoxaline derivative represented by the above general formula (G0) is preferably hydrogen in view of synthesis yield because the steric hindrance of the dibenzo[f,h]quinoxaline derivative is reduced to assist the ortho-metalation with a metal ion. Further, it is preferable that $R^2$, $R^4$, $R^5$, $R^7$, and $R^8$ be each hydrogen in view of ease of synthesis. In this case, the organometallic complex of the present invention has a structure represented by the following general formula (G2'). Accordingly, a preferable mode of the present invention is an organometallic complex having a partial structure represented by the following general formula (G2').

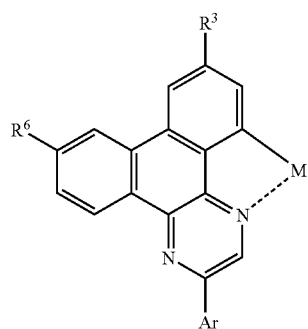

(G2')

In the formula, Ar represents an aryl group having 6 to 25 carbon atoms; $R^3$ and $R^6$ each represent any one of hydrogen, an alkyl group having 1 to 4 carbon atoms, an alkoxy group having 1 to 4 carbon atoms, and a halogen group; and M is a central metal of Group 9 elements and Group 10 elements.

It is preferable that $R^3$ and $R^6$ be each hydrogen in the above general formula (G2') in view of further ease of synthesis. Accordingly, a more preferable mode of the present invention is an organometallic complex having a partial structure represented by the following general formula (G3').

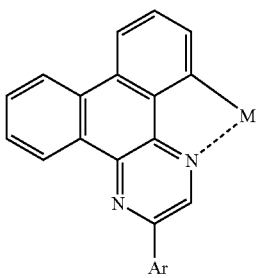

(G3')

In the formula, Ar represents an aryl group having 6 to 25 carbon atoms, and M is a central metal of Group 9 elements and Group 10 elements.

When Ar in the general formula (G3') is a substituted or unsubstituted phenyl group, red light emission with excellent color purity and high luminous efficiency can be obtained. Accordingly, a further preferable mode of the present invention is an organometallic complex having a partial structure represented by the following general formula (G4').

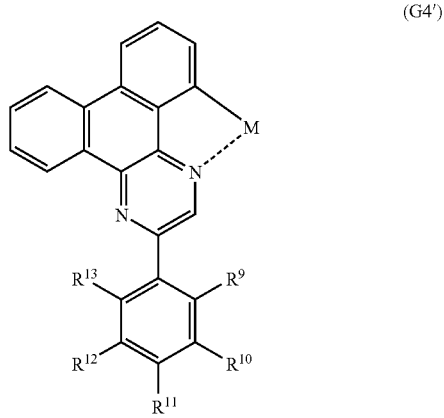

(G4')

In the formula, $R^9$ to $R^{13}$ each represent any one of hydrogen, an alkyl group having 1 to 4 carbon atoms, an alkoxy group having 1 to 4 carbon atoms, an aryl group having 6 to 12 carbon atoms, and a halogen group; and M is a central metal of Group 9 elements and Group 10 elements.

$R^9$ to $R^{13}$ in the general formula (G4') are each preferably hydrogen. Such a structure enables red light emission having the chromaticity near the red-color chromaticity defined by NTSC (National Television Standards Committee) (i.e., (x, y)=(0.67, 0.33)).

Here, an organometallic complex represented by the following general formula (G1) is preferable as a specific structure of the organometallic complex having the partial structure represented by the above general formula (G1') in view of ease of synthesis.

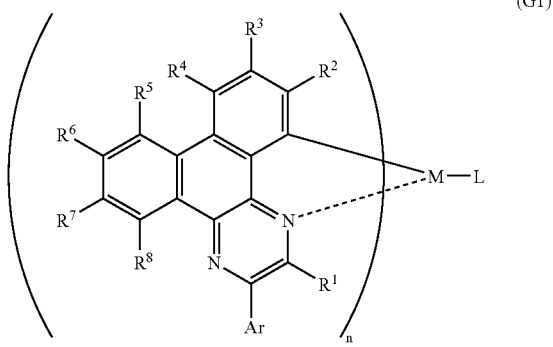

(G1)

In the formula, Ar represents an aryl group having 6 to 25 carbon atoms; $R^1$ represents any one of hydrogen, an alkyl group having 1 to 4 carbon atoms, and an alkoxy group having 1 to 4 carbon atoms; $R^2$ to $R^8$ each represent any one of hydrogen, an alkyl group having 1 to 4 carbon atoms, an alkoxy group having 1 to 4 carbon atoms, and a halogen group; at least one of pairs $R^3$ and $R^4$, $R^4$ and $R^5$, and $R^5$ and $R^6$ may be bound to each other to form a ring; M is a central metal and a Group 9 element or a Group 10 element; L represents a monoanionic ligand; and n is 2 when the central metal is a Group 9 element, and n is 1 when the central metal is a Group 10 element.

An organometallic complex represented by the following general formula (G2) is preferable as a specific structure of the organometallic complex having the structure represented by the above general formula (G1) in view of ease of synthesis.

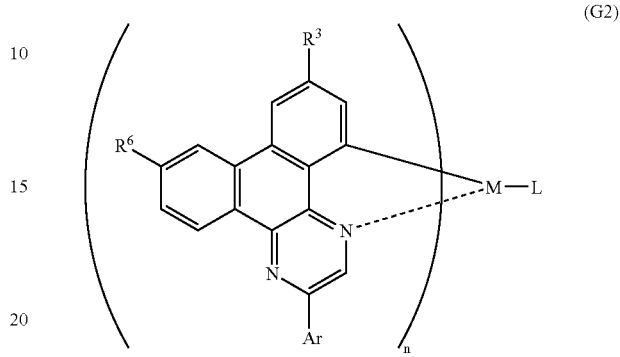

(G2)

In the formula, Ar represents an aryl group having 6 to 25 carbon atoms; $R^3$ and $R^6$ each represent any one of hydrogen, an alkyl group having 1 to 4 carbon atoms, an alkoxy group having 1 to 4 carbon atoms, and a halogen group; M is a central metal of Group 9 elements and Group 10 elements; L represents a monoanionic ligand; and n is 2 when the central metal is a Group 9 element, and n is 1 when the central metal is a Group 10 element.

More specifically, an organometallic complex represented by the following general formula (G3) is preferable as the organometallic complex having the structure represented by the above general formula (G2) in view of ease of synthesis.

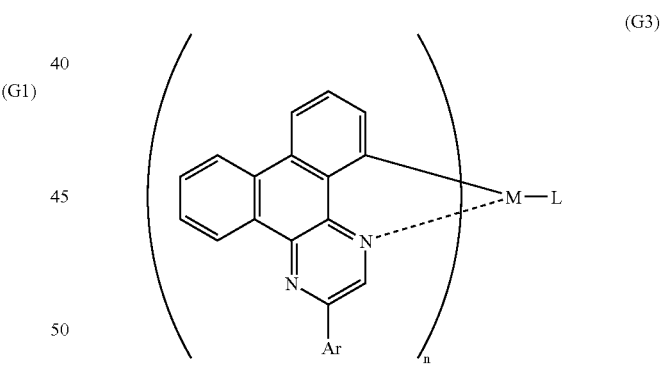

(G3)

In the formula, Ar represents an aryl group having 6 to 25 carbon atoms; M is a central metal of Group 9 elements and Group 10 elements; L represents a monoanionic ligand; and n is 2 when the central metal is a Group 9 element, and n is 1 when the central metal is a Group 10 element.

When Ar in the general formula (G3) is a substituted or unsubstituted phenyl group, red light emission with excellent color purity and high luminous efficiency can be obtained. Accordingly, an organometallic complex represented by the following general formula (G4) is further specifically preferable as the organometallic complex having the structure represented by the above general formula (G3).

(G4)

In the formula, $R^9$ to $R^{13}$ each represent any one of hydrogen, an alkyl group having 1 to 4 carbon atoms, an alkoxy group having 1 to 4 carbon atoms, an aryl group having 6 to 12 carbon atoms, and a halogen group; M is a central metal of Group 9 elements and Group 10 elements; L represents a monoanionic ligand; and n is 2 when the central metal is a Group 9 element, and n is 1 when the central metal is a Group 10 element.

$R^9$ to $R^{13}$ in the general formula (G4) are each preferably hydrogen. Such a structure enables red light emission having the chromaticity near the red-color chromaticity defined by NTSC (National Television Standards Committee) (i.e., (x, y)=(0.67, 0.33)).

The above-mentioned monoanionic ligand L is preferably any one of a monoanionic bidentate chelate ligand having a β-diketone structure, a monoanionic bidentate chelate ligand having a phenolic hydroxyl group, and a monoanionic bidentate chelate ligand in which two ligand elements are both nitrogen. This is because these ligands have high coordinating ability. More preferably, the monoanionic ligand L represents a monoanionic ligand represented by the following structural formulae (L1) to (L9). Since these ligands have high coordinating ability and can be obtained at low price, they are useful.

(L1)

(L2)

(L3)

(L4)

(L5)

(L6)

(L7)

(L8)

(L9)

In order to obtain phosphorescence more efficiently, a heavy metal is preferable as the central metal in terms of heavy atom effect. In the present invention, the central metal M in the above organometallic complex of the present invention is thus characterized to be iridium or platinum. Among them, iridium is particularly preferable because heat resistance of the organometallic complex can be improved by using iridium as the central metal M.

A coordination structure including ortho-metalation of the dibenzo[f,h]quinoxaline derivative represented by the general formula (G0) with a metal ion greatly contributes to the function of phosphorescence of the organometallic complex having the partial structure represented by any of the above general formulae (G1') to (G4') (inclusive of the organometallic complex represented by the above general formulae (G1) to (G4)). Therefore, another aspect of the present invention is a light-emitting material including the organometallic complex as described above.

The organometallic complex of the present invention is highly effective in realizing higher efficiency in a case of being applied to a light-emitting element because the organometallic complex of the present invention is capable of phosphorescence, that is, conversion of triplet excitation energy to light. Thus, the present invention also provides a light-emitting element including the above-described organometallic complex.

At this time, the organometallic complex of the present invention is effective in use for a light-emitting substance in terms of emission efficiency. Therefore, one aspect of the present invention is a light-emitting element including the organometallic complex of the present invention as a light-emitting substance. The light-emitting element preferably has a structure in which a light-emitting layer is interposed between a pair of electrodes, the light-emitting layer has a first layer and a second layer, the first layer includes the organometallic complex of the present invention and a first organic compound, and the second layer includes the organometallic complex of the present invention and a second organic compound.

The light-emitting element of the present invention, which is formed as described above, can realize high emission efficiency, and thus, a light-emitting device (e.g., an image display device) including this light-emitting element can have low power consumption. Accordingly, the present invention includes a light-emitting device and an electronic device including the above-described light-emitting element of the present invention.

The light-emitting device of the present invention is characterized by including a layer including a light-emitting substance between a pair of electrodes, a light-emitting element including the above-described organometallic complex in the layer including a light-emitting substance, and a control unit to control light emission from the light-emitting element. In this specification, the term "light-emitting device" includes an image display device including a light-emitting element. Further, the category of the light-emitting device includes a module including a substrate provided with a light-emitting element, attached with a connector, for example, a tape automated bonding (TAB) tape such as an anisotropic conductive film or a tape carrier package (TCP); a module in which an end of the connector is provided with a printed wiring board; or a module in which an integrated circuit (IC) is directly mounted on a substrate, provided with a light-emitting element, by a chip on glass (COG) method; and the like.

The electronic device of the present invention is characterized by including a display portion that includes the above-described light-emitting element and the control unit to control light emission from the light-emitting element.

The organometallic complex of the present invention can emit red light. Further, the organometallic complex of the present invention is an organometallic complex having high emission efficiency. Furthermore, the organometallic complex of the present invention can emit red light with high luminous efficiency.

Further, a light-emitting element that emits red light with high emission efficiency, a light-emitting element that emits red light with high luminous efficiency, and a light-emitting element capable of long-time driving can be obtained by using the organometallic complex of the present invention for manufacturing the light-emitting element.

Further, by using the organometallic complex of the present invention, it is possible to obtain a light-emitting device and an electronic device that not only obtain effect of the organometallic complex of the present invention and the light-emitting element including it but also achieve low power consumption.

BRIEF DESCRIPTION OF THE DRAWINGS

In the accompanying drawings:

FIGS. 4A and 4B are views illustrating a light-emitting device of the present invention;

DETAILED DESCRIPTION OF THE INVENTION

Figure 1:
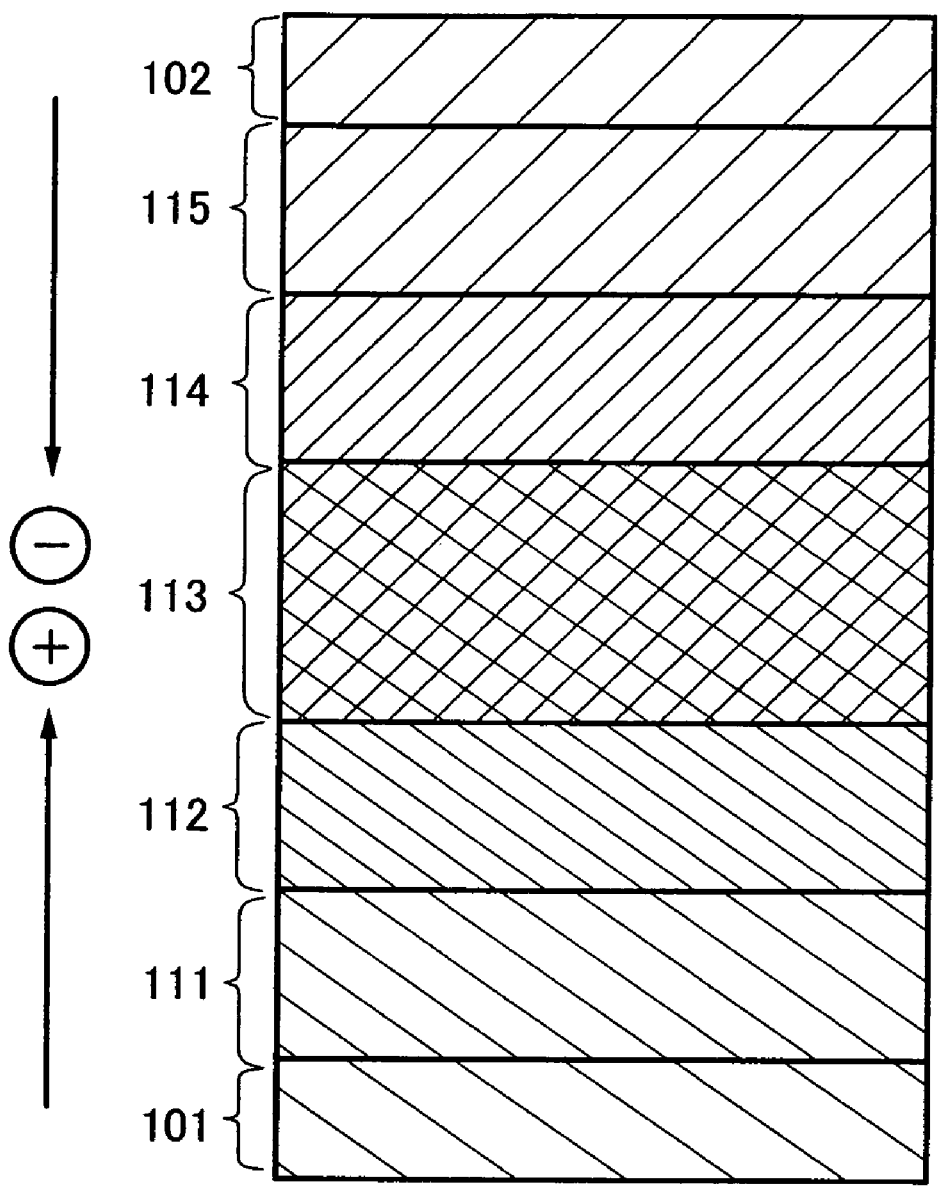
FIG. 1 is a view illustrating a light-emitting element of the present invention.

Hereinafter, embodiment modes and examples of the present invention will be described with reference to the accompanying drawings. It is to be noted that the present invention can be carried out in many various modes. It is easily understood by those skilled in the art that various changes may be made in forms and details without departing from the spirit and the scope of the present invention. Therefore, the present invention should not be limited to the description of the embodiment modes and examples below.

Embodiment Mode 1

Embodiment Mode 1 will describe the organometallic complex of the present invention.
<Synthetic Method of a Dibenzo[f,h]quinoxaline Derivative Represented by the General Formula (G0)>

An organometallic complex of the present invention is formed by ortho-metalation of a dibenzo[f,h]quinoxaline derivative represented by the following general formula (G0) with a metal ion of Group 9 or Group 10.

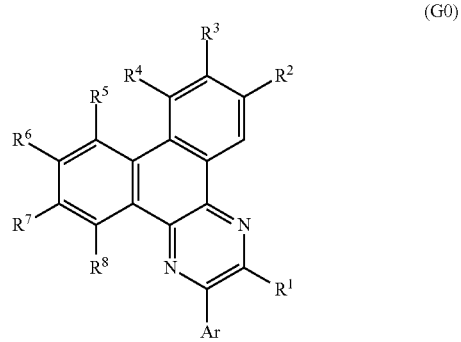

(G0)

In the formula, Ar represents an aryl group having 6 to 25 carbon atoms; $R^1$ represents any one of hydrogen, an alkyl group having 1 to 4 carbon atoms, and an alkoxy group having 1 to 4 carbon atoms; $R^2$ to $R^8$ each represent any one of hydrogen, an alkyl group having 1 to 4 carbon atoms, an alkoxy group having 1 to 4 carbon atoms, and a halogen group; and at least one of pairs $R^3$ and $R^4$, $R^4$ and $R^5$, and $R^5$ and $R^6$ may be bound to each other to form a ring.

Hereinafter, explanation will be made on synthetic methods of the dibenzo[f,h]quinoxaline derivative represented by the general formula (G0) separately for each of the cases where $R^1$ in the general formula (G0) is an alkyl group having 1 to 4 carbon atoms or an alkoxy group having 1 to 4 carbon atoms (the following general formula (G0-1)) and where $R^1$ is hydrogen (the following general formula (G0-2)).

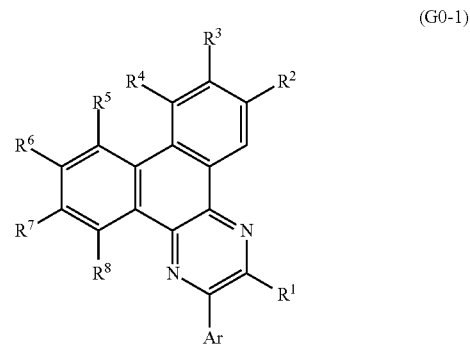

(G0-1)

In the formula, Ar represents an aryl group having 6 to 25 carbon atoms; $R^1$ represents any one of an alkyl group having 1 to 4 carbon atoms and an alkoxy group having 1 to 4 carbon atoms; $R^2$ to $R^8$ each represent any one of hydrogen, an alkyl group having 1 to 4 carbon atoms, an alkoxy group having 1 to 4 carbon atoms, and a halogen group; and at least one of pairs $R^3$ and $R^4$, $R^4$ and $R^5$, and $R^5$ and $R^6$ may be bound to each other to form a ring.

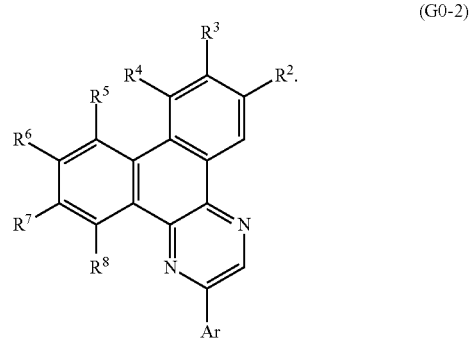

(G0-2)

In the formula, Ar represents an aryl group having 6 to 25 carbon atoms; $R^2$ to $R^8$ each represent any one of hydrogen, an alkyl group having 1 to 4 carbon atoms, an alkoxy group having 1 to 4 carbon atoms, and a halogen group; and at least one of pairs $R^3$ and $R^4$, $R^4$ and $R^5$, and $R^5$ and $R^6$ may be bound to each other to form a ring.

First, the dibenzo[f,h]quinoxaline derivative represented by the general formula (G0-1) can be synthesized according to the following simple synthetic scheme. For example, the dibenzo[f,h]quinoxaline derivative can be obtained by a reaction of a diaminophenanthrene compound (A1) and a diketone compound (A2) as shown in the following scheme (a).

(a)

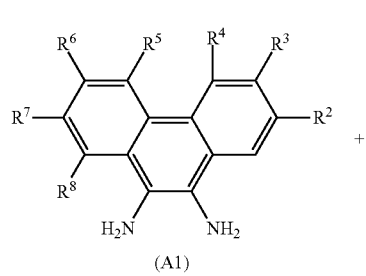
(A1)

+

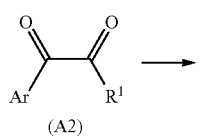
(A2)

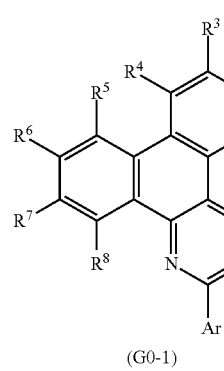
(G0-1)

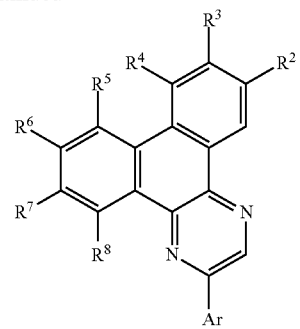
(G0-2)

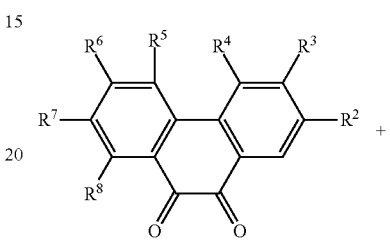
(A1″)

+

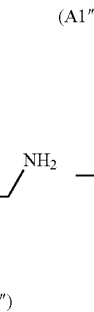
(A2″)

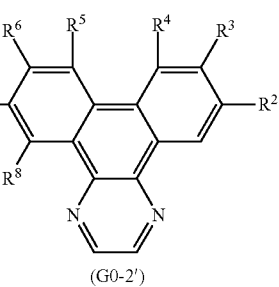
(G0-2′)

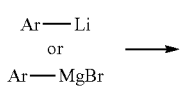
(A3)

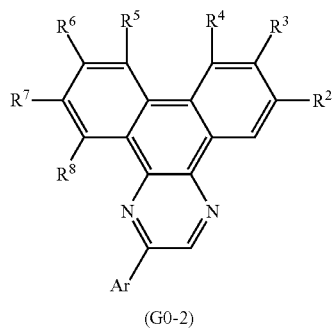
(G0-2)

The dibenzo[f,h]quinoxaline derivative represented by the general formula (G0-2) can be synthesized according to the following simple synthetic scheme. For example, as shown in the following scheme (a′), the dibenzo[f,h]quinoxaline derivative can be obtained by a reaction of a diaminophenanthrene compound (A1′) and a diketone compound (A2′). Alternatively, as shown in the following scheme (a″), the dibenzo[f,h]quinoxaline derivative can be obtained as follows: a diketone compound (A1″) is reacted with a diamine compound (A2″) to obtain a dibenzo[f,h]quinoxaline derivative (G0-2′) and then this dibenzo[f,h]quinoxaline derivative (G0-2′) is reacted with an aryllithium compound or an arylmagnesium bromide compound (A3).

(a′)

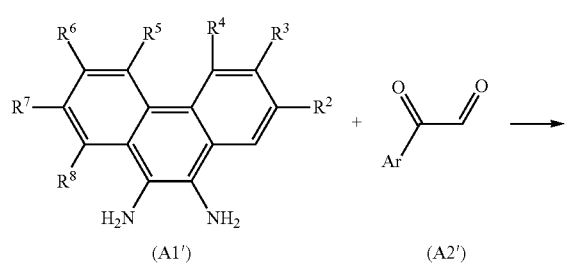 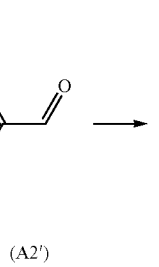
(A1′) (A2′)

Since various kinds of the above-described compounds (A1), (A2), (A1′), (A2′), (A1″), (A2″), and (A3) are available commercially or can be synthesized, many kinds of the dibenzo[f,h]quinoxaline derivative represented by the above-described general formula (G0) can be synthesized.

<Synthetic Method of the Organometallic Complex of the Present Invention Having a Partial Structure Represented by the General Formula (G1′)>

Next, an organometallic complex of the present invention that is formed by ortho-metalation of the dibenzo[f,h]quinoxaline derivative represented by the general formula (G0), that is, an organometallic complex having a partial structure represented by the following general formula (G1′) will be described.

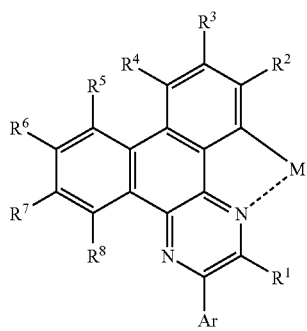

(G1')

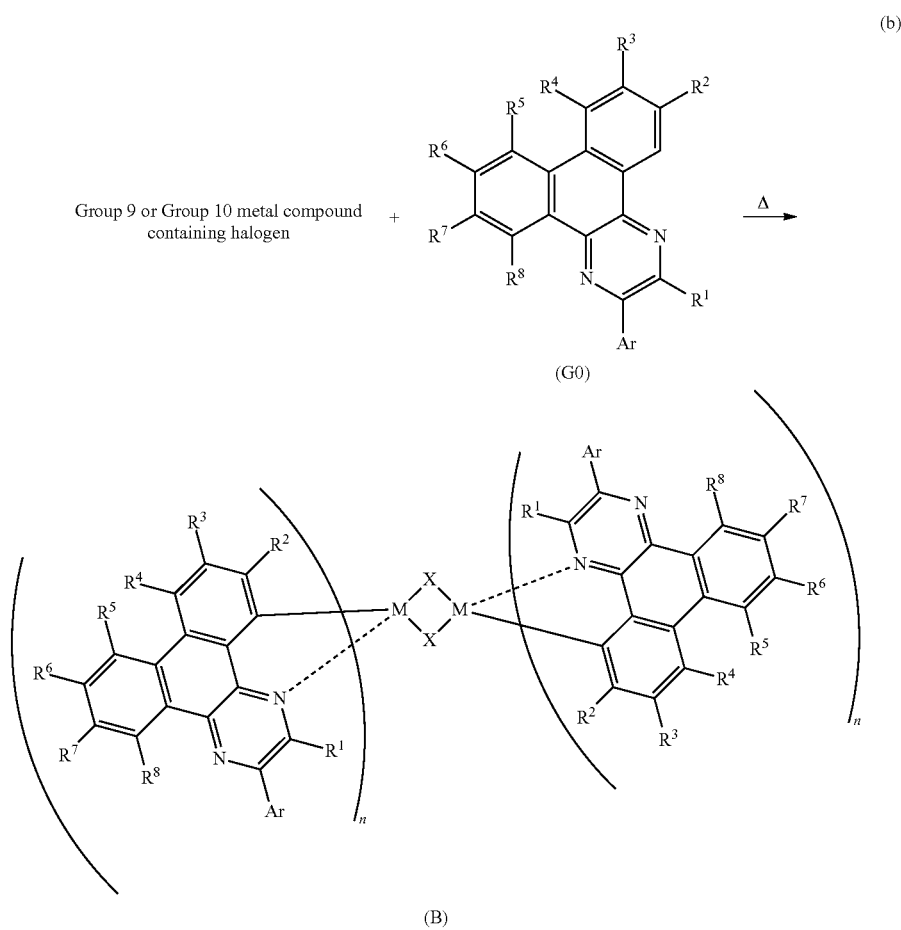

eral formula (G0) and a Group 9 or Group 10 metal compound containing halogen (e.g., a metal halide or a metal complex) are heated in an appropriate solvent to obtain a dinuclear complex (B) which is one kind of the organometallic complex of the present invention having the structure represented by the general formula (G1'). Examples of the Group 9 or Group 10 metal compound containing halogen include rhodium chloride hydrate, palladium chloride, iridium chloride hydrate, iridium chloride hydrate hydrochloride, potassium tetrachloroplatinate(II), and the like, but are not limited to these examples. It is to be noted that, in the synthetic scheme (b), M represents a Group 9 element or a Group 10 element, and X represents a halogen element. In addition, n is 2 when M is a Group 9 element, and n is 1 when M is a Group 10 element.

In the formula, Ar represents an aryl group having 6 to 25 carbon atoms; $R^1$ represents any one of hydrogen, an alkyl group having 1 to 4 carbon atoms, and an alkoxy group having 1 to 4 carbon atoms; $R^2$ to $R^8$ each represent any one of hydrogen, an alkyl group having 1 to 4 carbon atoms, an alkoxy group having 1 to 4 carbon atoms, and a halogen group; at least one of pairs $R^3$ and $R^4$, $R^4$ and $R^5$, and $R^5$ and $R^6$ may be bound to each other to form a ring; and M is a central metal of Group 9 elements and Group 10 elements.

First, as shown in the following synthetic scheme (b), the dibenzo[f,h]quinoxaline derivative represented by the gen- Further, as shown in the following synthetic scheme (c), the dinuclear complex (B) and the dibenzo[f,h]quinoxaline derivative represented by the general formula (G0) are heated at a high temperature of about 200° C. in a high boiling solvent such as glycerol to obtain one kind (C) of the organometallic complex of the present invention having the partial structure represented by the general formula (G1'). Furthermore, as shown in the following synthetic scheme (c'), the dinuclear complex (B) and a compound capable of ortho-metalation (more generally, a compound capable of cyclometalation) such as phenylpyridine are heated at a high temperature of about 200° C. in a high boiling solvent such as glycerol to obtain one kind (C') of the organometallic complex of the present invention having the partial structure represented by the general formula (G1'). It is to be noted that, in the synthetic schemes (c) and (c'), M represents a Group 9 element or a Group 10 element, and X represents a halogen element. In addition, n is 2 when M is a Group 9 element, and n is 1 when M is a Group 10 element.
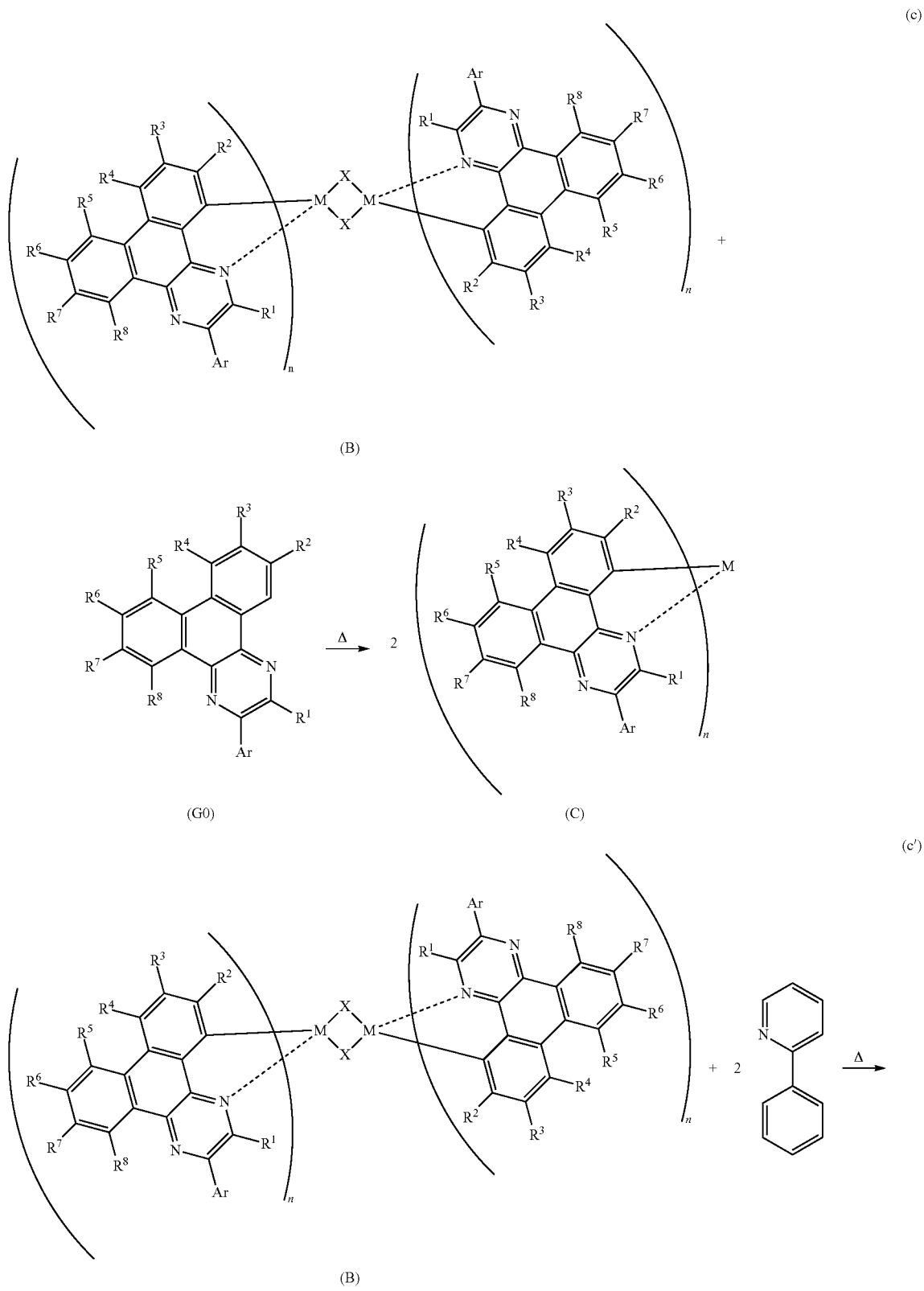

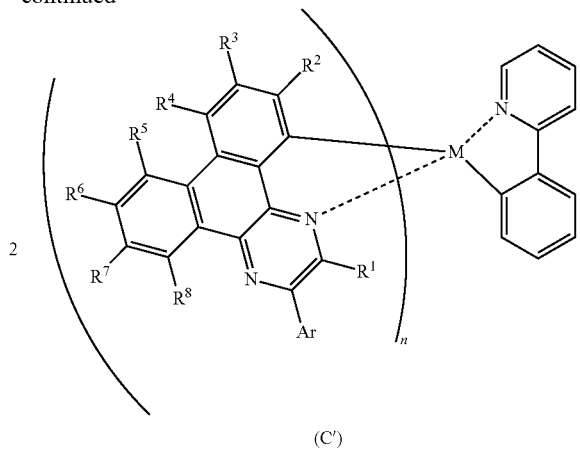

(C′)

<Synthetic Method of the Organometallic Complex Having a Structure of the Present Invention Represented by the General Formula (G1)>

Here, explanation will be made on the organometallic complex represented by the following general formula (G1), which is a preferable specific example among the above organometallic complexes having the partial structure represented by the general formula (G1').

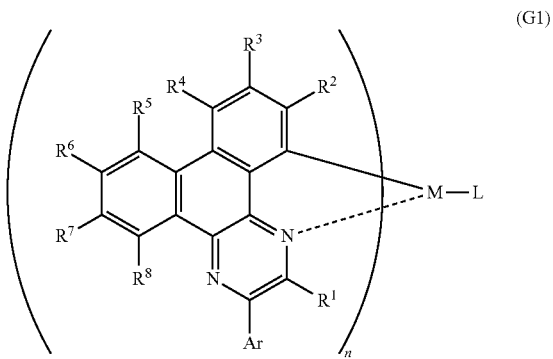

(G1)

In the formula, Ar represents an aryl group having 6 to 25 carbon atoms; $R^1$ is any one of hydrogen, an alkyl group having 1 to 4 carbon atoms, and an alkoxy group having 1 to 4 carbon atoms; $R^2$ to $R^8$ each represent any one of hydrogen, an alkyl group having 1 to 4 carbon atoms, an alkoxy group having 1 to 4 carbon atoms, and a halogen group; at least one of pairs $R^3$ and $R^4$, $R^4$ and $R^5$, and $R^5$ and $R^6$ may be bound to each other to form a ring; M is a central of Group 9 elements and Group 10 elements; L represents a monoanionic ligand; and n is 2 when the central metal is a Group 9 element, and n is 1 when the central metal is a Group 10 element.

The organometallic complex of the present invention represented by the above general formula (G1) can be synthesized according to the following synthetic scheme (c″). That is, it can be obtained as follows: the dinuclear complex (B) obtained according to the above synthetic scheme (b) is reacted with HL that is a material of a monoanionic ligand L, and a proton of HL is eliminated and coordinated to the central metal M. It is to be noted that, in the synthetic scheme (c″), M represents a Group 9 element or a Group 10 element and X represents a halogen element. In addition, n is 2 when M is a Group 9 element, and n is 1 when M is a Group 10 element.

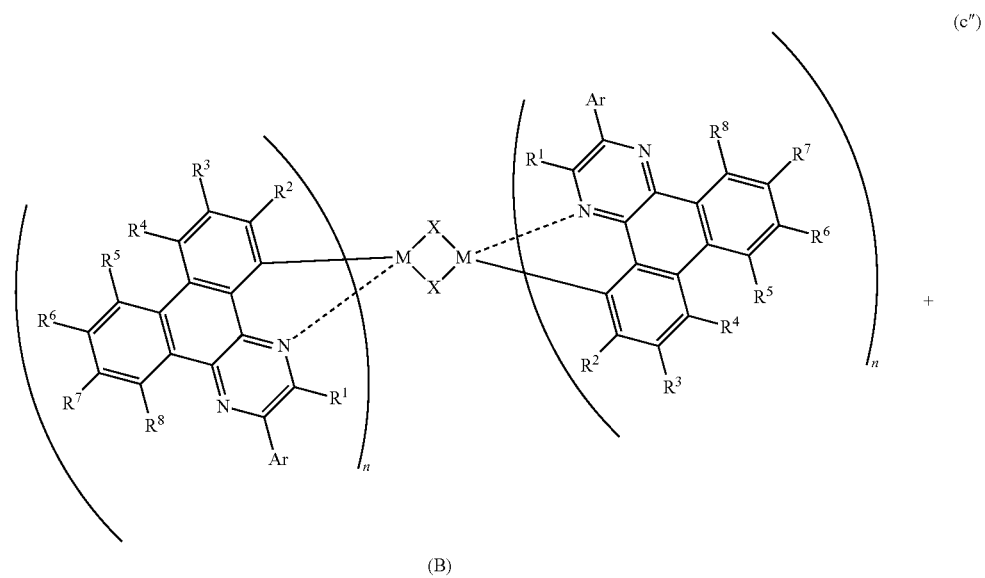

(c″)

(B)

2HL $\xrightarrow{\Delta}$ 2

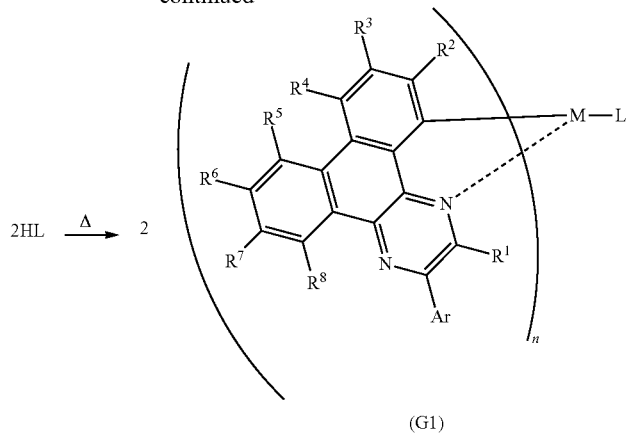

(G1)

<Specific Structural Formulae of the Organometallic Complex of the Present Invention Having a Partial Structure Represented by the General Formula (G1') and the Organometallic Complex of the Present Invention Represented by the General Formula (G1)>

Next, specific structural formulae of the organometallic complex of the present invention having a partial structure represented by the general formula (G1') and the organometallic complex of the present invention represented by the general formula (G1) will be disclosed.

First, although the central metal M is selected from Group 9 elements or Group 10 elements, iridium(III) or platinum(II) is preferable in terms of emission efficiency. In particular, iridium(III) is preferable because of its thermal stability.

Next, a ligand portion P surrounded by dashed lines in the following general formulae (G1') and (G1) is described. As described above, M represents a Group 9 element or a Group 10 element. L represents a monoanionic ligand (specific examples are described below). In addition, n is 2 when M is a Group 9 element, and n is 1 when M is a Group 10 element.

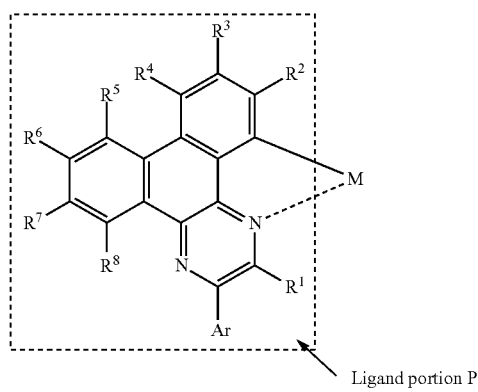

(G1')

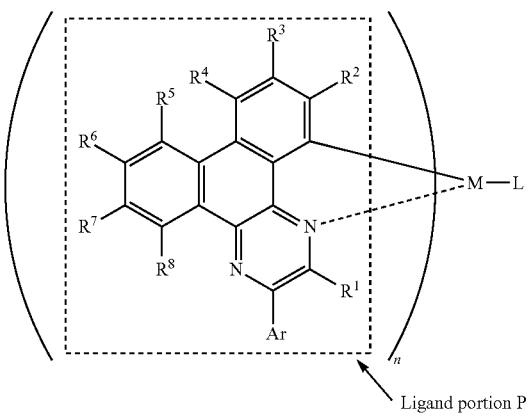

-continued
(G1)

Specific examples of a substituent $R^1$ include an alkyl group such as a methyl group, an ethyl group, an isopropyl group, or a tert-butyl group as well as an alkoxy group such as a methoxy group, an ethoxy group, an isopropoxy group, or a tert-butoxy group. A case in which $R^1$ is hydrogen reduces steric hindrance of the ligand portion P to assist the ortho-metalation with a metal ion, and is thus preferable in terms of synthesis yield.

Specific examples of substituents $R^2$ to $R^8$ include hydrogen; an alkyl group such as a methyl group, an ethyl group, an isopropyl group, or a tert-butyl group; an alkoxy group such as a methoxy group, an ethoxy group, an isopropoxy group, or a tert-butoxy group; an acyl group such as an acetyl group; and a halogen group such as a fluoro group. A methylene group is given as a specific example in a case where $R^4$ and $R^5$ are bound to each other to form a ring. Further, a methylenedioxy group and the like are given as specific examples in a case where $R^3$ and $R^4$ are bound to each other to form a ring, and $R^5$ and $R^6$ are bound to each other to form a ring.

Specific examples of the aryl group Ar include a substituted or unsubstituted phenyl group, a 1-naphthyl group, a 2-naphthyl group, a spirofluorene-2-yl group, a 9,9-dialkylfluorene-2-yl group such as a 9,9-dimethylfluorene-2-yl group, and the like. In particular, when a substituted or unsubstituted phenyl group is used as the aryl group Ar, red light emission with excellent color purity and high luminous efficiency can be obtained. In a case where the phenyl group has a substituent, the substituent may specifically be an alkyl group such as a methyl group, an ethyl group, an isopropyl group, or a tert-butyl group; an alkoxy group such as a methoxy group, an ethoxy group, an isopropoxy group, or a tert-butoxy group; an aryl group such as a phenyl group or a 4-biphenylyl group; a halogen group such as a fluoro group; or a trifluoromethyl group. It is to be noted that, in this specification, "carbon atoms" in the aryl group represented by "Ar" refer to carbon atoms to form a ring, not carbon atoms in the substituent bound to the ring.

In a case where $R^1$ to $R^8$ are each hydrogen, a structure in which the aryl group Ar is an unsubstituted phenyl group is preferable because it enables red light emission having the chromaticity near the red-color chromaticity defined by NTSC (National Television Standards Committee) (i.e., (x, y)=(0.67, 0.33)).

As the structure of the ligand portion P in the above general formulae (G0) and (G1), more specifically, any structure of the following ligand groups 1 and 2 can be applied. However, the present invention is not limited to these structures. In the formulae, α indicates a position of carbon that is bound to the central metal M. β indicates a position of nitrogen that is coordinated to the central metal M.

Ligand Group 1

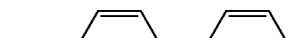

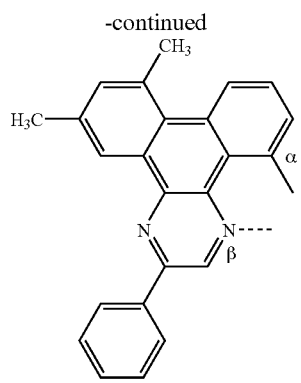

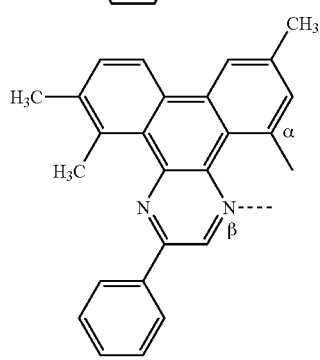

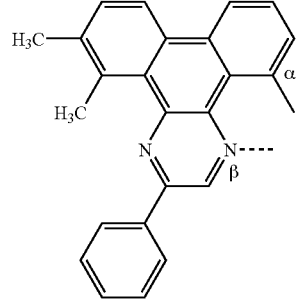

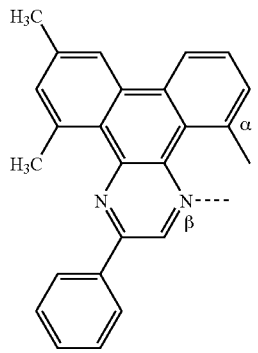

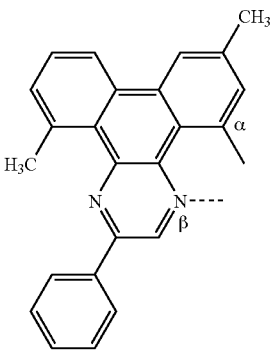

25
-continued
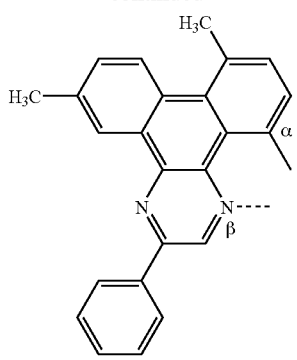
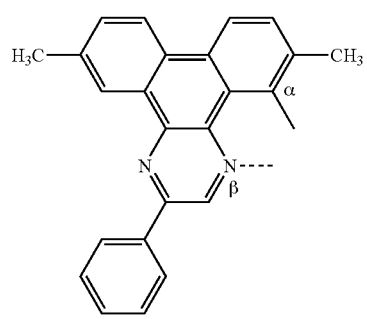
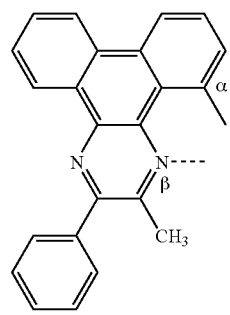
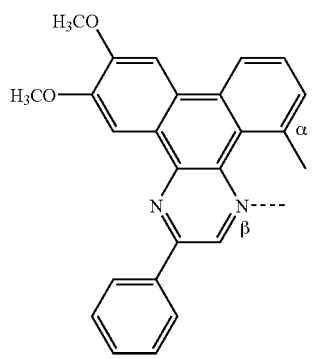
26
Ligand Group 2
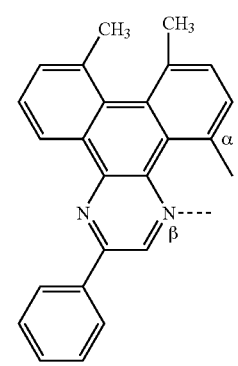
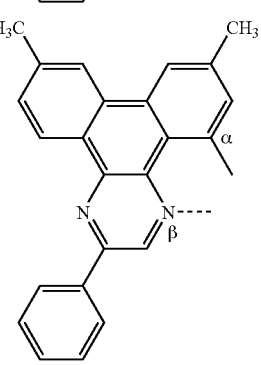
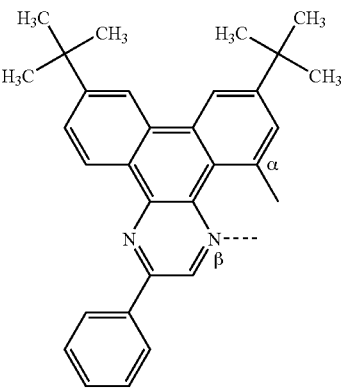
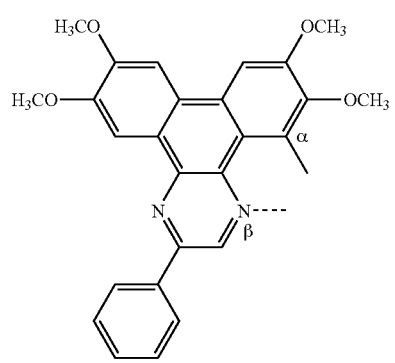

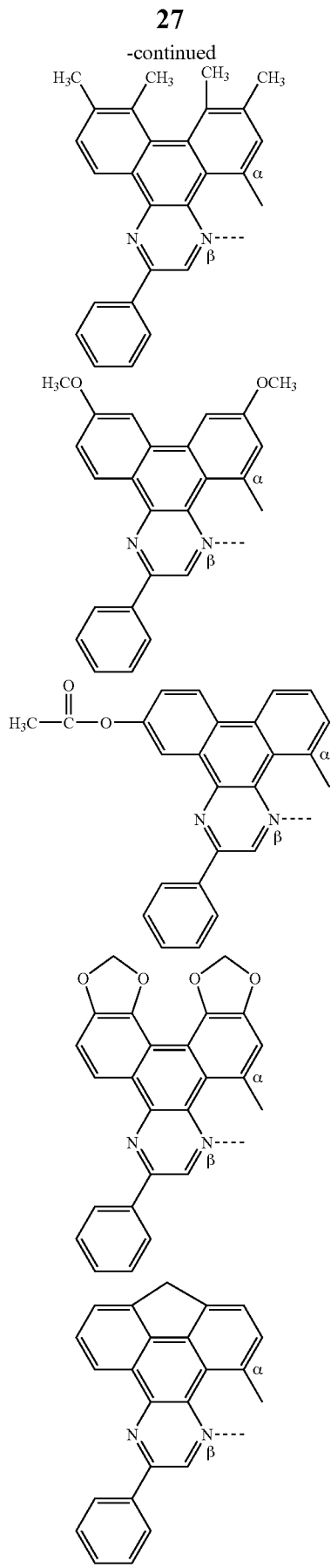

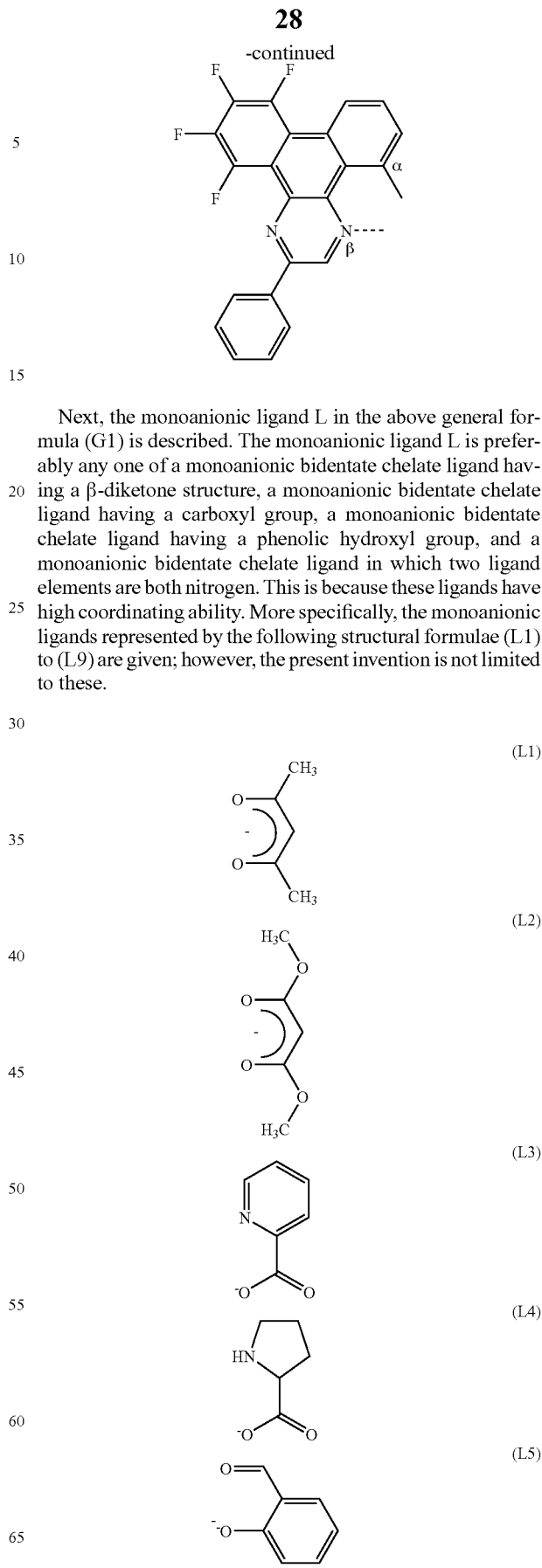

Next, the monoanionic ligand L in the above general formula (G1) is described. The monoanionic ligand L is preferably any one of a monoanionic bidentate chelate ligand having a β-diketone structure, a monoanionic bidentate chelate ligand having a carboxyl group, a monoanionic bidentate chelate ligand having a phenolic hydroxyl group, and a monoanionic bidentate chelate ligand in which two ligand elements are both nitrogen. This is because these ligands have high coordinating ability. More specifically, the monoanionic ligands represented by the following structural formulae (L1) to (L9) are given; however, the present invention is not limited to these.

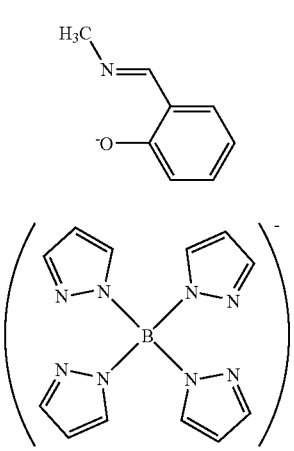 (L6)

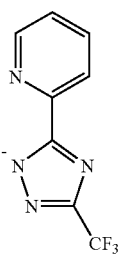 (L7)

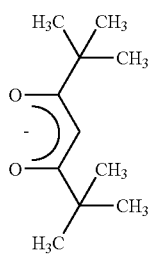 (L8)

(L9)

An appropriate combination of the central metal M, the ligand groups 1 and 2, and the monoanionic ligand L as described above constitute the organometallic complex of the present invention. Hereinafter, specific structural formulae of the organometallic complex of the present invention are given (the following structural formulae (1) to (54)). However, the present invention is not limited to these.

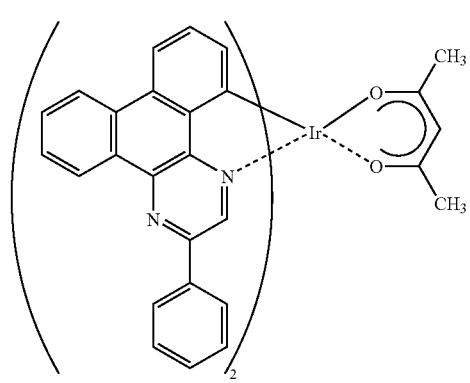 (1)

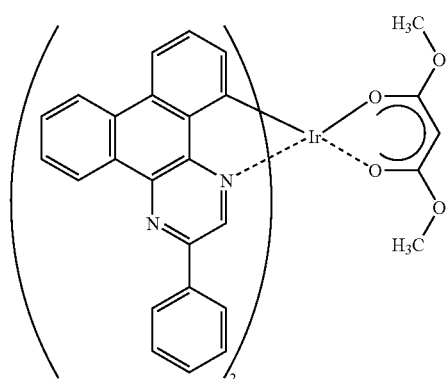 (2)

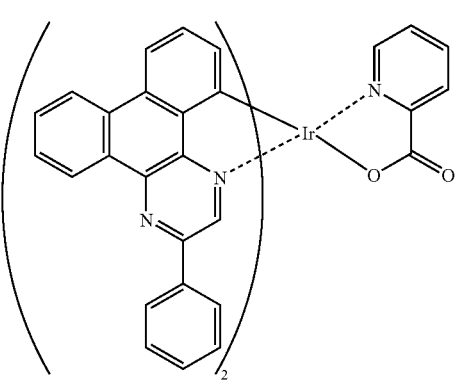 (3)

(4)

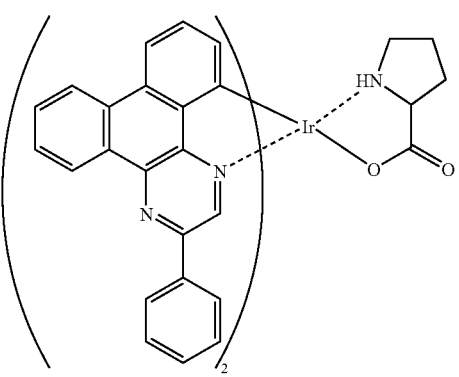 (5)

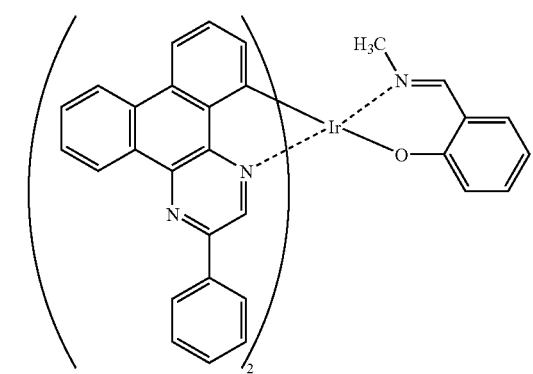
(6)
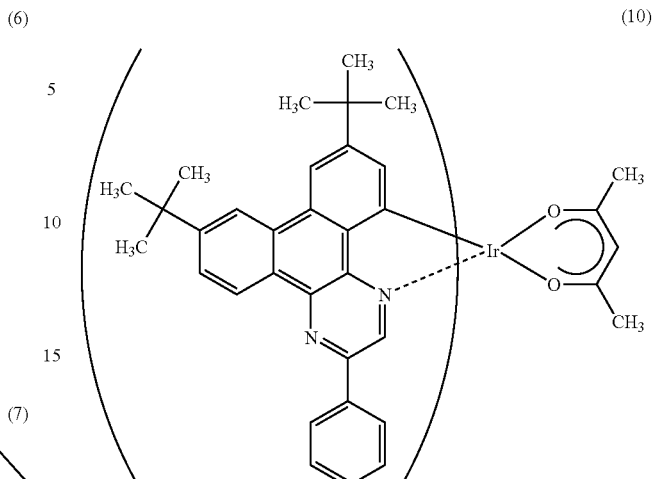
(10)
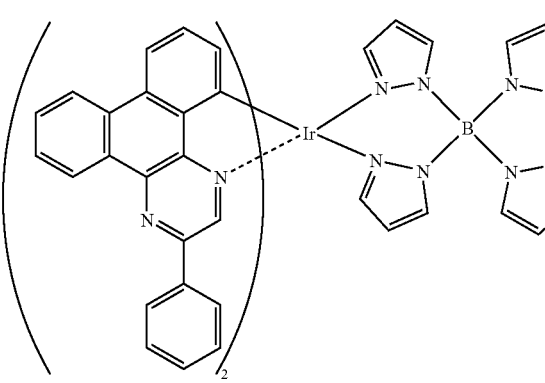
(7)
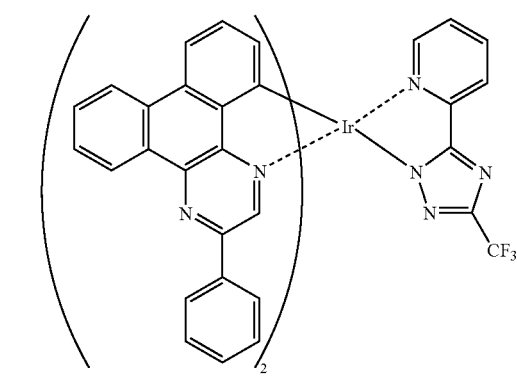
(8)
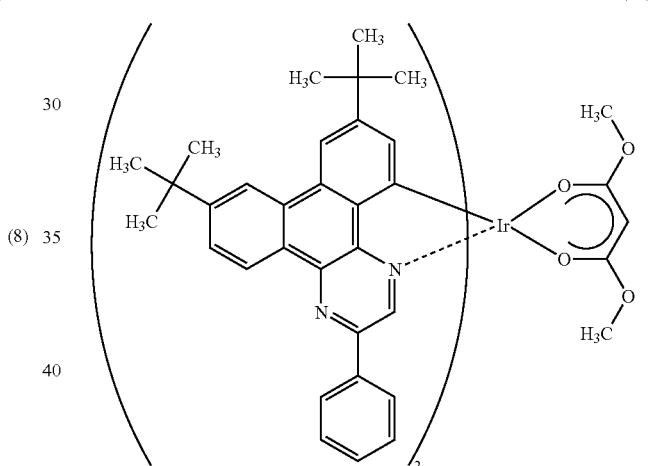
(11)
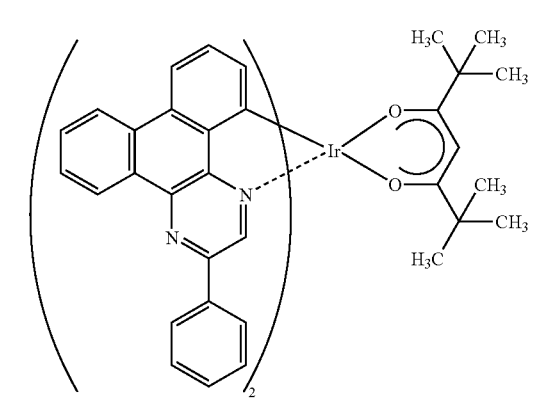
(9)
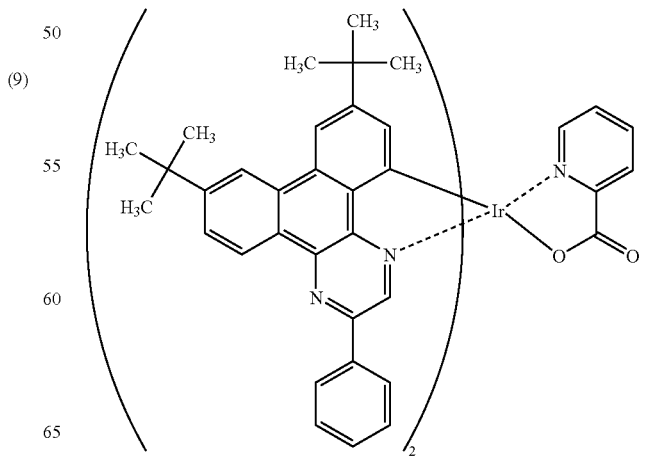
(12)

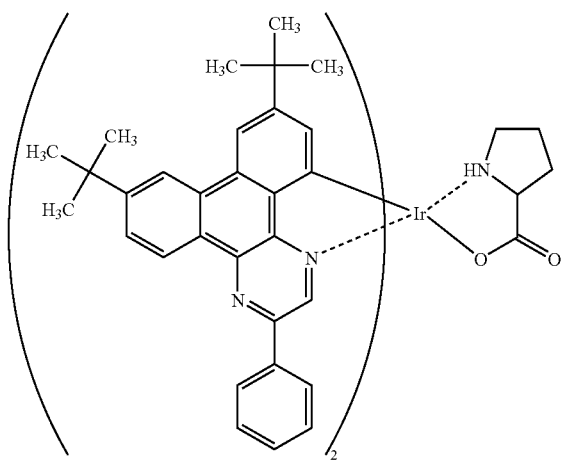
(13)
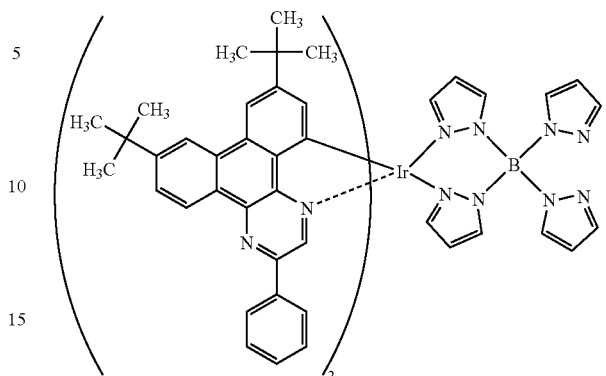
(16)
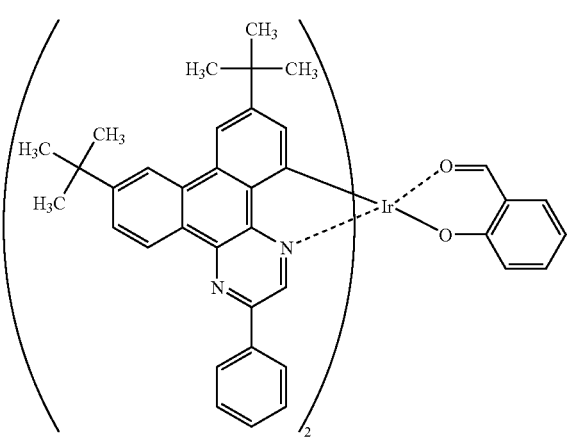
(14)
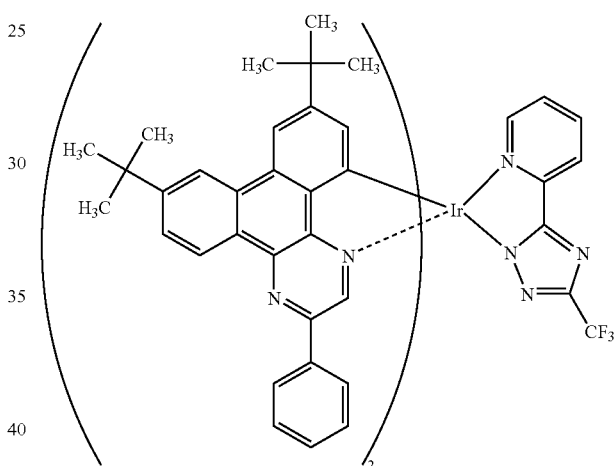
(17)
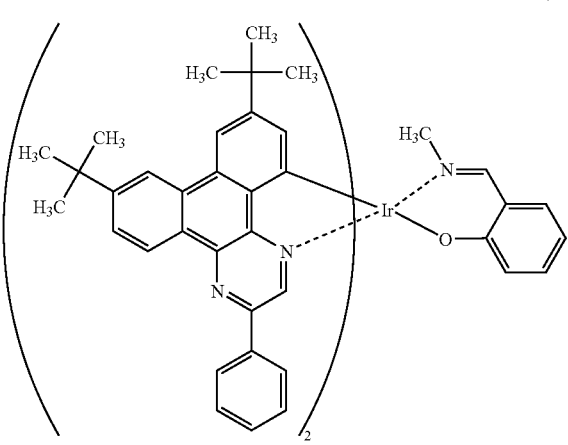
(15)
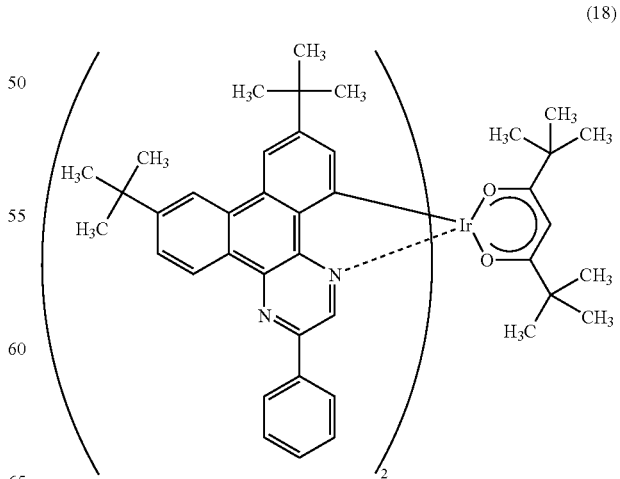
(18)

(19)
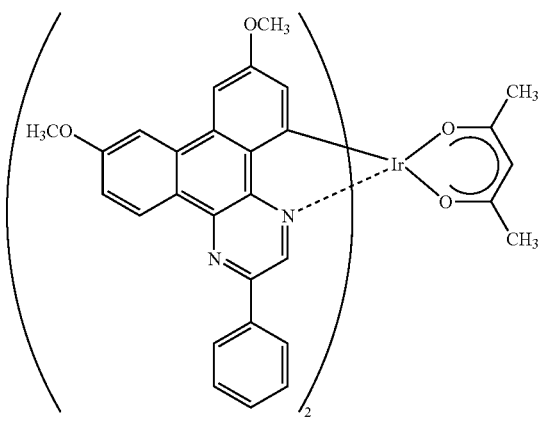
(20)
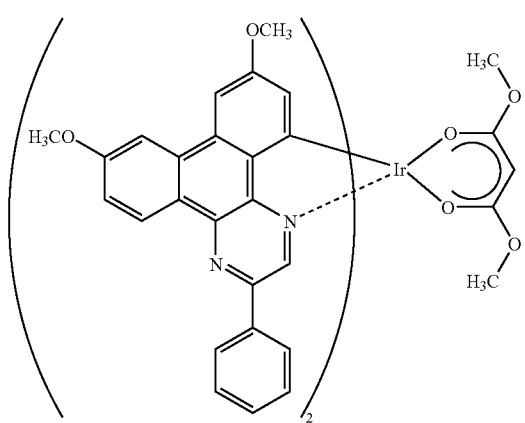
(21)
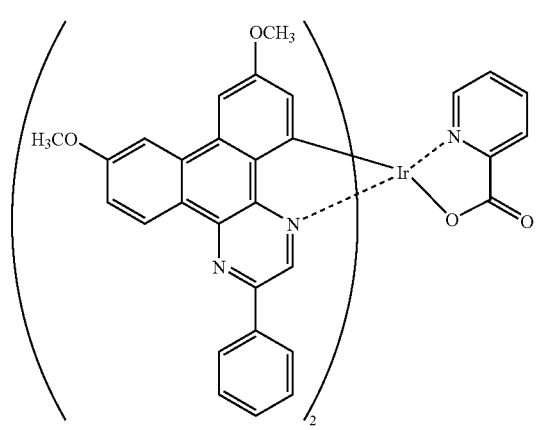
(22)
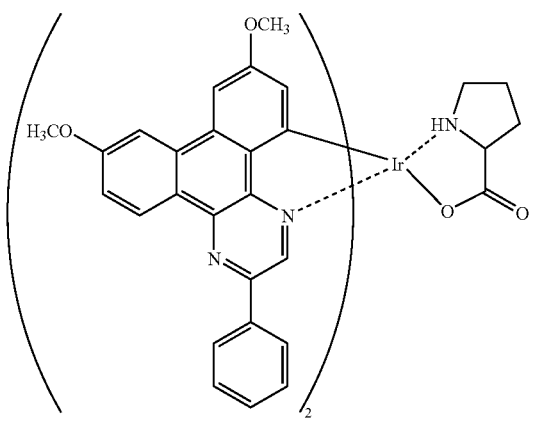
(23)
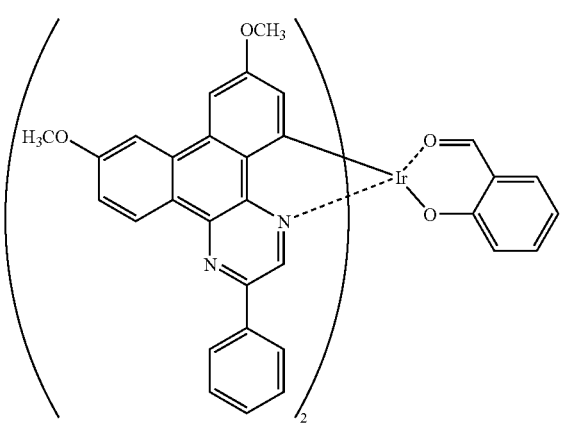
(24)
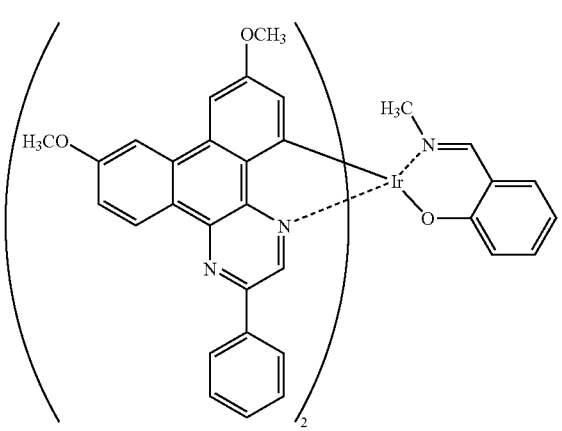

-continued
(25)
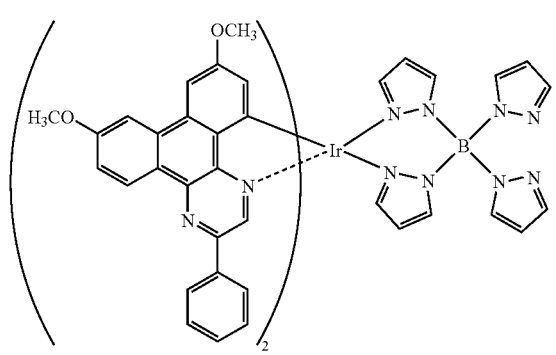
(26)
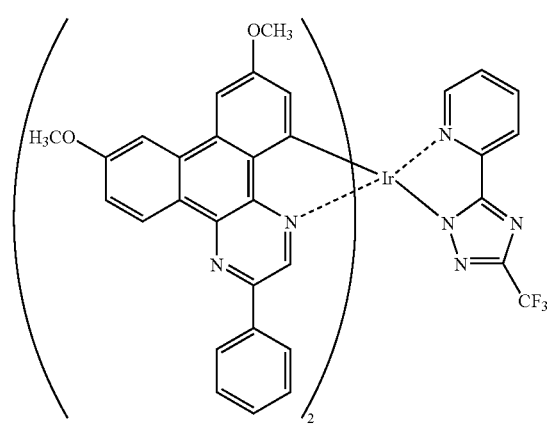
(27)
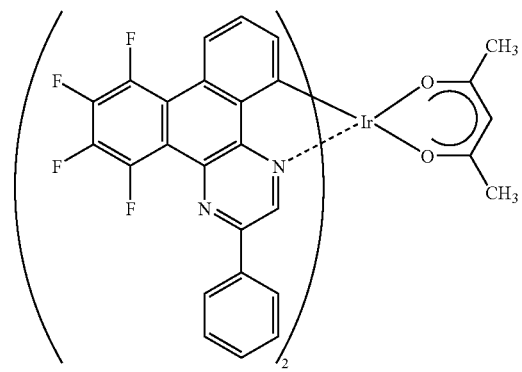
(28)
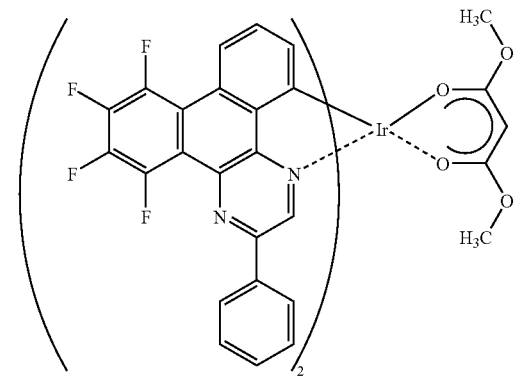
-continued
(29)
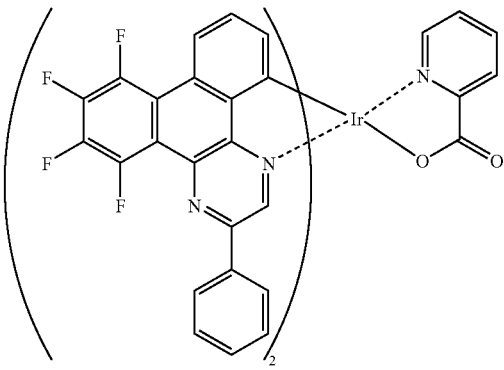
(30)
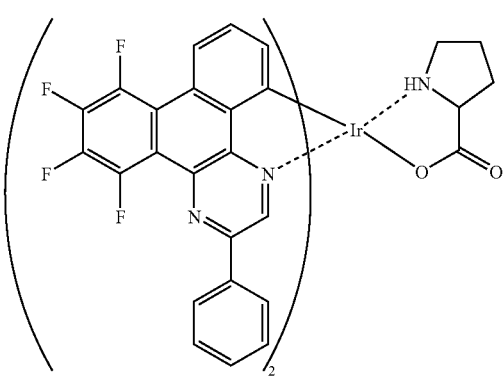
(31)
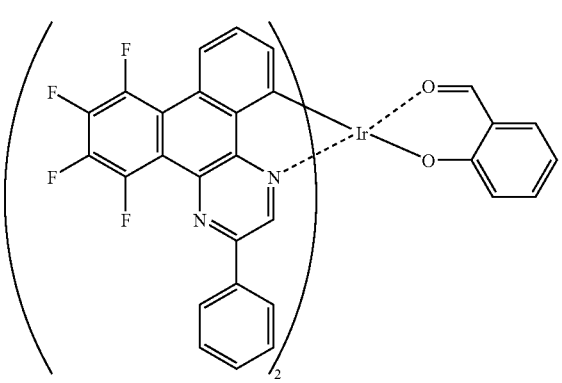
(32)
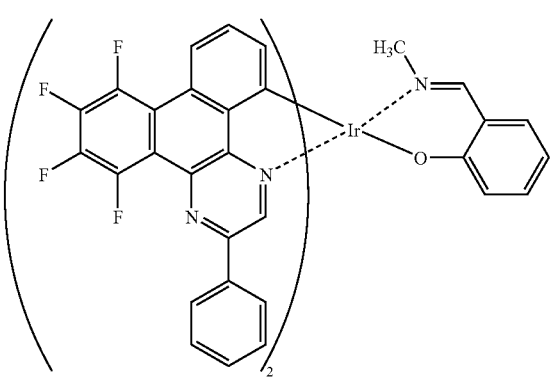

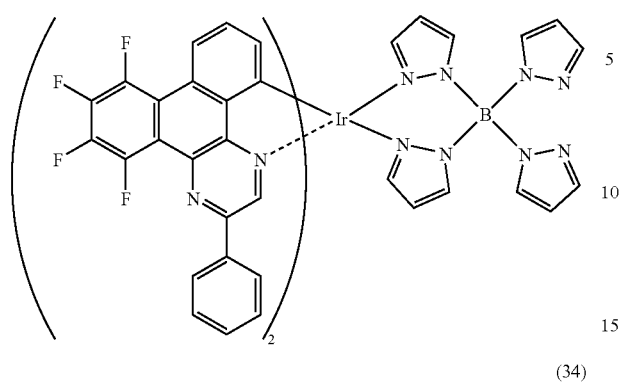
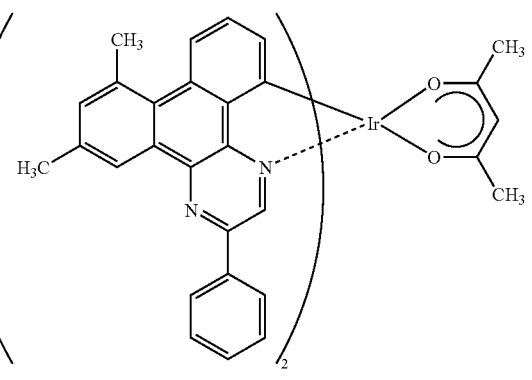

(41)
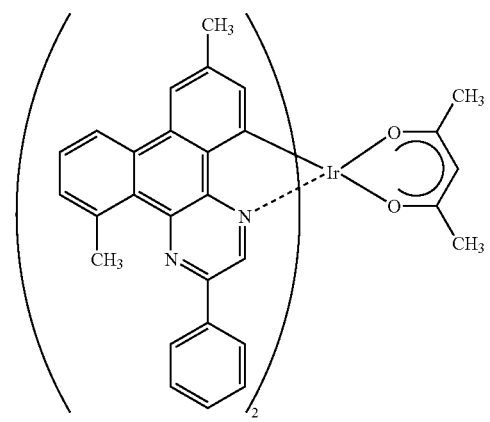
(42)
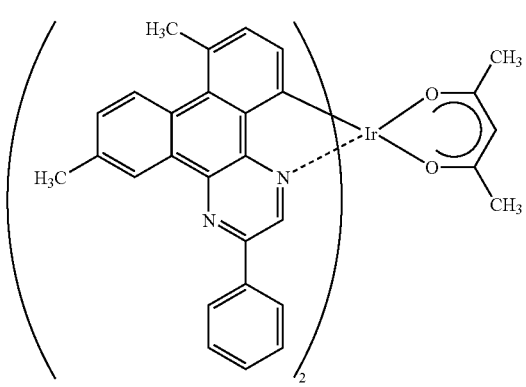
(43)
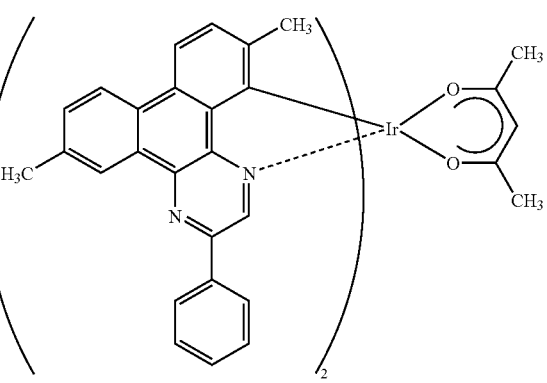
(44)
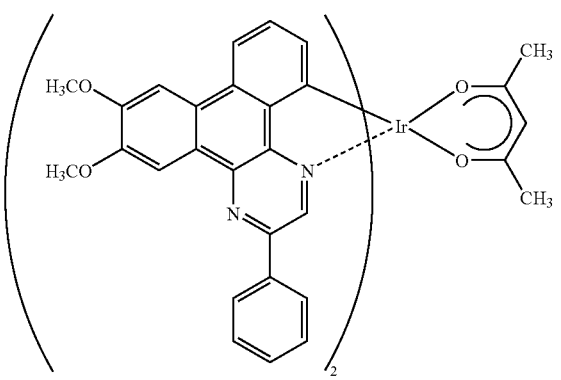
(45)
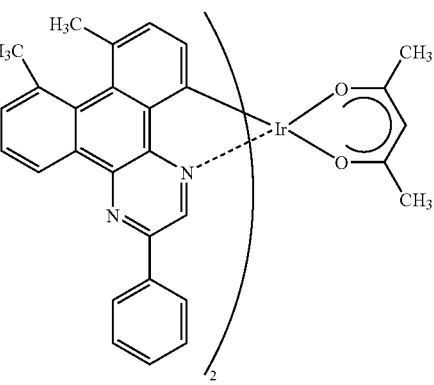
(46)
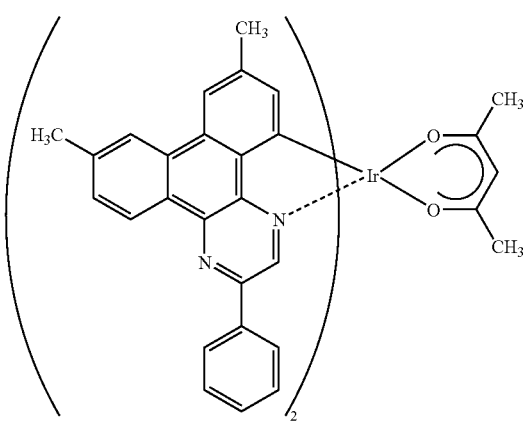
(47)
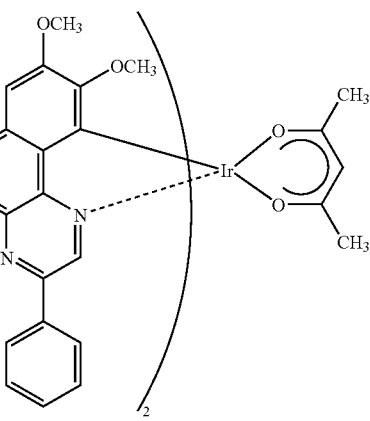

(48)
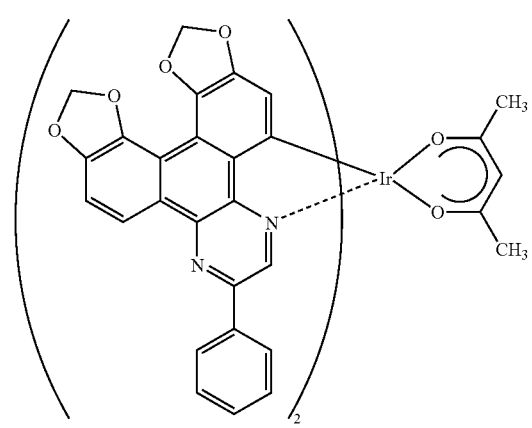

(49)
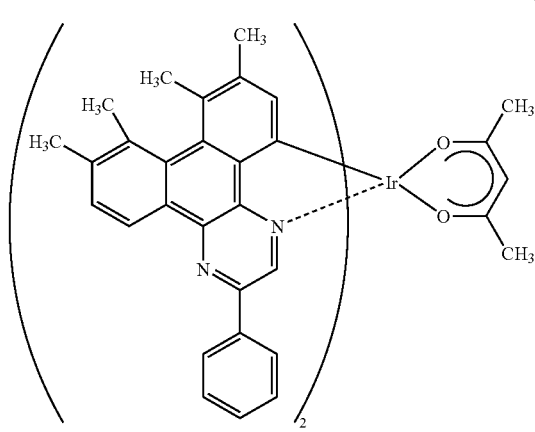

(50)
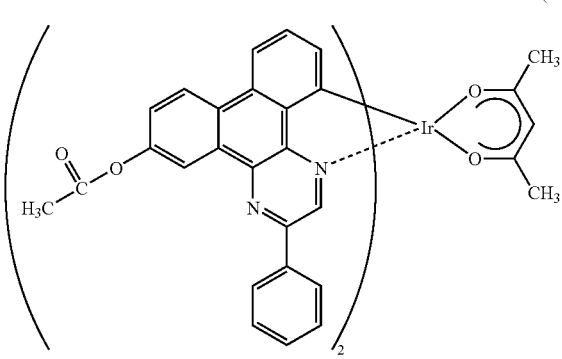

(51)
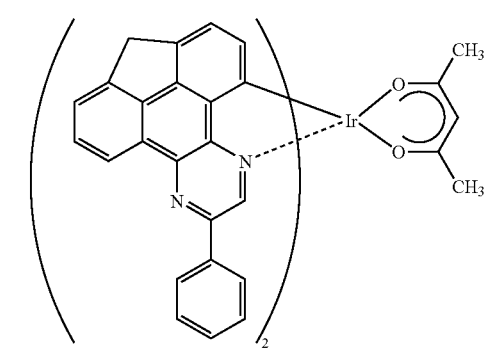

(52)
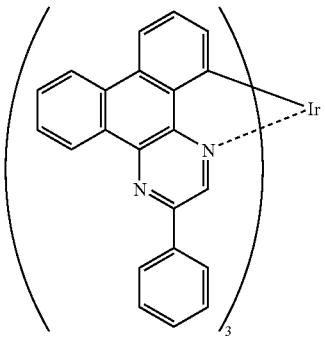

(53)
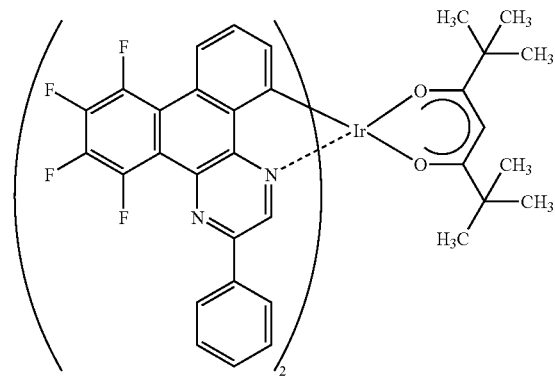

(54)
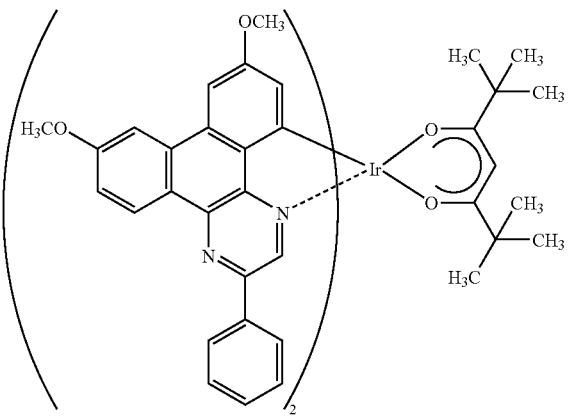

It is to be noted that, although a geometrical isomer or a stereoisomer can be included, depending on the type of ligand, in the organometallic complexes represented by the above structural formulae (1) to (54), both isomers are included in the organometallic complex of the present invention.

The organometallic complex represented by structural formula (52) includes two geometrical isomers of a facial isomer and a meridional isomer. The organometallic complex of the present invention includes both isomers.

The foregoing organometallic complex of the present invention can be used as a photosensitizer owing to capability of intersystem crossing. Further, it can exhibit phosphorescence. Thus, the organometallic complex of the present invention can be used as a light-emitting material or a light-emitting substance for a light-emitting element.

Embodiment Mode 2

Embodiment Mode 2 will describe a mode of a light-emitting element that includes the organometallic complex of the present invention, described in Embodiment Mode 1, as a light-emitting substance with reference to FIG. 1.

FIG. 1 illustrates a light-emitting element including a light-emitting layer 113 between a first electrode 101 and a second electrode 102. The light-emitting layer 113 includes the organometallic complex of the present invention as described above in Embodiment Mode 1.

By applying voltage to such a light-emitting element, holes injected from the first electrode 101 and electrons injected from the second electrode 102 are recombined with each other in the light-emitting layer 113 to bring the organometallic complex of the present invention to an excited state. Light is emitted when the organometallic complex in the excited state returns to the ground state. The organometallic complex of the present invention thus functions as a light-emitting substance of the light-emitting element. It is to be noted that the first electrode 101 and the second electrode 102 function as an anode and a cathode, respectively, in the light-emitting element of Embodiment Mode 2.

Here, the light-emitting layer 113 includes the organometallic complex of the present invention. The light-emitting layer 113 is preferably a layer including a substance that has a larger triplet excitation energy than the organometallic complex of the present invention as a host and also including the organometallic complex of the present invention, which is dispersed as a guest. Thus, quenching of light emission from the organometallic complex of the present invention caused depending on the concentration can be prevented. It is to be noted that the triplet excitation energy refers to an energy difference between a ground state and a triplet excited state.

Non-limiting preferable examples of the substance used for dispersing the organometallic complex of the present invention (i.e., a host) include a compound having an arylamine skeleton, such as 2,3-bis(4-diphenylaminophenyl)quinoxaline (abbreviation: TPAQn) or 4,4'-bis[N-(1-naphthyl)-N-phenylamino]biphenyl (abbreviation: NPB); a carbazole derivative such as 4,4'-di(N-carbazolyl)biphenyl (abbreviation: CBP) or 4,4',4''-tris(N-carbazolyl)triphenylamine (abbreviation: TCTA); and a metal complex such as bis[2-(2-hydroxyphenyl)pyridinato]zinc (abbreviation: Znpp$_2$), bis[2-(2-hydroxyphenyl)benzoxazolato]zinc (abbreviation: Zn(PBO)$_2$), bis(2-methyl-8-quinolinolato)(4-phenylphenolato)aluminum (abbreviation: BAlq) or tris(8-quinolinolato)aluminum (abbreviation: Alq$_3$). In particular, the organometallic complex of the present invention can emit light efficiently with the use of a metal complex such as bis[2-(2-hydroxyphenyl)pyridinato]zinc (abbreviation: Znpp$_2$), bis[2-(2-hydroxyphenyl)benzoxazolato]zinc (abbreviation: Zn(PBO)$_2$), or bis(2-methyl-8-quinolinolato)(4-phenylphenolato)aluminum (abbreviation: BAlq). Alternatively, a high molecular compound may be used as the substance used for dispersing the organometallic complex of the present invention. In this case, a solution obtained by dissolving the organometallic complex of the present invention and the high molecular compound in an appropriate solvent is applied by a wet method such as ink jetting or spin coating to form the light-emitting layer 113. Non-limiting examples of the solvent include tetrahydrofuran (THF), acetonitrile, dichloromethane, dichloroethane, toluene, xylene, and a mixed solvent thereof as well as lower alcohol such as methanol, ethanol, n-propanol, n-butanol, or sec-butanol. Examples of the high molecular compound include a hole transporting high molecular compound such as poly(N-vinylcarbazole) (abbreviation: PVK), poly(4-vinyltriphenylamine) (abbreviation: PVTPA), poly[N-(4-{N'-[4-(4-diphenylamino)phenyl]phenyl-N'-phenylamino}phenyl)methacrylamide] (abbreviation: PTPDMA), or poly[N,N'-bis(4-butylphenyl)-N,N'-bis(phenyl)benzidine (abbreviation: Poly-TPD). An electron transporting high molecular compound such as poly[(9,9-dihexylfluorene-2,7-diyl)-co-(pyridin-3,5-diyl)] (abbreviation: PF-Py) or poly[(9,9-dioctylfluorene-2,7-diyl)-co-(2,2'-pyridin-6,6-diyl)] (abbreviation: PF-BPy) can alternatively be used as the high molecular compound. It is to be noted that the light-emitting layer 113 can be formed not only by sputtering or evaporation but also by a wet method such as ink jetting or spin coating.

Because the organometallic complex of the present invention can emit red light, a light-emitting element that emits red light can be obtained. Because the organometallic complex of the present invention has high emission efficiency, a light-emitting element with high emission efficiency can be obtained. Further, a light-emitting element capable of long-time driving can be obtained. Furthermore, a light-emitting element that emits red light with high luminous efficiency can be obtained.

Since the light-emitting element of the present invention has high emission efficiency, power consumption can be reduced.

Although there are no particular limitations on the first electrode 101, it is preferably formed using a substance having a high work function in a case of functioning as an anode as in this embodiment mode. Specific examples of the substance having a high work function include gold (Au), platinum (Pt), nickel (Ni), tungsten (W), chromium (Cr), molybdenum (Mo), iron (Fe), cobalt (Co), copper (Cu), palladium (Pd), and the like in addition to indium tin oxide (ITO), indium tin oxide containing silicon oxide (ITSO), and indium oxide containing zinc oxide at 2 to 20 wt % (IZO). The first electrode 101 can be formed by, for example, sputtering, evaporation, or the like.

Further, although there are also no particular limitations on the second electrode 102, it is preferably formed of a substance having a low work function in a case of functioning as a cathode as in this embodiment mode. Specific examples of the substance having a low work function include an alkali metal such as lithium (Li) or cesium (Cs), an alkaline-earth metal such as magnesium (Mg) or calcium (Ca), and a rare-earth metal such as erbium (Er) or ytterbium (Yb), in addition to aluminum (Al) and indium (In). In addition, an alloy such as an aluminum-lithium alloy (AlLi) and a magnesium-silver alloy (MgAg) can be included. The second electrode 102 can be formed by, for example, sputtering, evaporation, or the like.

In order to extract emitted light to the outside, it is necessary that one or both of the first electrode 101 and the second electrode 102 be an electrode formed using a conductive film that can transmit visible light, such as ITO, or an electrode with a thickness of several to several tens of nm so as to transmit visible light.

A hole transporting layer 112 may be provided between the first electrode 101 and the light-emitting layer 113 as illustrated in FIG. 1. Here, the hole transporting layer is a layer that has a function of transporting holes injected from the first electrode 101 to the light-emitting layer 113. In this manner, the hole transporting layer 112 is provided to keep the first electrode 101 away from the light-emitting layer 113; thus, quenching of light emission due to metal can be prevented. However, the hole transporting layer 112 is not necessarily provided.

Although there are no particular limitations on a substance forming the hole transporting layer 112, the following substances can be typically used as this substance: an aromatic amine compound such as 4,4'-bis[N-(1-naphthyl)-N-phenylamino]biphenyl (abbreviation: NPB), 4,4'-bis[N-(3-methylphenyl)-N-phenylamino]biphenyl (abbreviation: TPD), 4,4'-bis[N-(9,9-dimethylfluoren-2-yl)-N-phenylamino]biphenyl (abbreviation: DFLDPBi), 4,4',4''-tris(N,N-diphenylamino)triphenylamine (abbreviation: TDATA), or 4,4',4''-tris[N-(3-methylphenyl)-N-phenylamino]triphenylamine (abbreviation: m-MTDATA). Moreover, a high molecular compound such as poly(4-vinyltriphenylamine) (abbreviation: PVTPA) can also be used.

The hole transporting layer 112 may have a multilayer structure in which two or more layers are stacked, or may be formed of a mixture of two or more kinds of substances.

Further, an electron transporting layer 114 may be provided between the second electrode 102 and the light-emitting layer 113 as illustrated in FIG. 1. Here, the electron transporting layer is a layer that has a function of transporting electrons injected from the second electrode 102 to the light-emitting layer 113. In this manner, the electron transporting layer 114 is provided to keep the second electrode 102 away from the light-emitting layer 113; thus, quenching of light emission due to a metal can be prevented. However, the electron transporting layer 114 is not necessarily provided.

Although there are no particular limitations on a substance forming the electron transporting layer 114, the following substances can be typically used as this substance: metal complexes such as tris(8-quinolinolato)aluminum (abbreviation: $Alq_3$), tris(4-methyl-8-quinolinolato)aluminum (abbreviation: $Almq_3$), bis(10-hydroxybenzo[h]quinolinato)beryllium (abbreviation: $BeBq_2$), bis(2-methyl-8-quinolinolato)(4-phenylphenolato)aluminum (abbreviation: BAlq), bis[2-(2-hydroxyphenyl)benzoxazolato]zinc (abbreviation: ZnBOX), and bis[2-(2-hydroxyphenyl)benzothiazolato]zinc (abbreviation: $Zn(BTZ)_2$). Further, a heteroaromatic compound such as 2-(4-biphenylyl)-5-(4-tert-butylphenyl)-1,3,4-oxadiazole (abbreviation: PBD), 1,3-bis[5-(p-tert-butylphenyl)-1,3,4-oxadiazol-2-yl]benzene (abbreviation: OXD-7), 3-(4-tert-butylphenyl)-4-phenyl-5-(4-biphenylyl)-1,2,4-triazole (abbreviation: TAZ), 3-(4-tert-butylphenyl)-4-(4-ethylphenyl)-5-(4-biphenylyl)-1,2,4-triazole (abbreviation: p-EtTAZ), bathophenanthroline (abbreviation: BPhen), bathocuproin (abbreviation: BCP), or 4,4'-bis(5-methylbenzoxazol-2-yl)stilbene (abbreviation: BzOs) can be used. Moreover, a high molecular compound such as poly(2,5-pyridin-diyl) (abbreviation: PPy) can also be used.

The electron transporting layer 114 may have a multilayer structure in which two or more layers are stacked, or may be formed of a mixture of two or more kinds of substances.

Further, a hole injecting layer 111 may be provided between the first electrode 101 and the hole transporting layer 112 as illustrated in FIG. 1. Here, the hole injecting layer is a layer that has a function of assisting injection of holes from the electrode functioning as an anode into the hole transporting layer 112. However, the hole injecting layer 111 is not necessarily provided.

Although there are no particular limitations on a substance forming the hole injecting layer 111, the following substances can be used as this substance: metal oxide such as vanadium oxide, niobium oxide, tantalum oxide, chromium oxide, molybdenum oxide, tungsten oxide, manganese oxide, rhenium oxide, and ruthenium oxide. Further, a phthalocyanine compound such as phthalocyanine (abbreviation: $H_2Pc$) or copper phthalocyanine (abbreviation: CuPc) can be used. Moreover, the substances used for forming the hole transporting layer 112 as described above can also be used. Further, a high molecular compound such as a mixture of poly(ethylenedioxythiophene) and poly(styrenesulfonate) (abbreviation: PEDOT/PSS) can also be used.

A composite material of an organic compound and an electron acceptor may be used for the hole injecting layer 111. Such a composite material is superior in a hole injecting property and a hole transporting property since holes are generated in the organic compound by the electron acceptor. In this case, the organic compound is preferably a material excellent in transporting the generated holes. Specifically, the foregoing substances forming the hole transporting layer 112 (e.g., aromatic amine compound) can be used for example. As the electron acceptor, a substance having an electron accepting property to the organic compound may be used. Specifically, transition metal oxide is preferable and examples thereof include vanadium oxide, niobium oxide, tantalum oxide, chromium oxide, molybdenum oxide, tungsten oxide, manganese oxide, rhenium oxide, ruthenium oxide, and the like. Lewis acid such as iron(III)chloride or aluminum(III) chloride can also be used. In addition, an organic compound such as 7,7,8,8-tetracyano-2,3,5,6-tetrafluoroquinodimethane (abbreviation: $F_4$-TCNQ) can also be used.

The hole injecting layer 111 may have a multilayer structure in which two or more layers are stacked, or may be formed of a mixture of two or more kinds of substances.

Further, an electron injecting layer 115 may be provided between the second electrode 102 and the electron transporting layer 114 as illustrated in FIG. 1. Here, the electron injecting layer is a layer that has a function of assisting injection of electrons from the electrode functioning as a cathode into the electron transporting layer 114. However, the electron injecting layer 115 is not necessarily provided.

Although there are no particular limitations on a substance forming the electron injecting layer 115, an alkali metal compound or an alkaline-earth metal compound such as lithium fluoride (LiF), cesium fluoride (CsF), calcium fluoride ($CaF_2$), or lithium oxide ($LiO_x$) can be given. In addition, a rare-earth metal compound such as erbium fluoride ($ErF_3$) can also be used. The above-mentioned substances forming the electron transporting layer 114 can also be used.

A composite material of an organic compound and an electron donor may be used for the electron injecting layer 115. Such a composite material is excellent in an electron injecting property and an electron transporting property since electrons are generated in the organic compound by the electron donor. In this case, the organic compound is preferably a material excellent in transporting the generated electrons. Specifically, the foregoing substances forming the electron transporting layer 114 (e.g., a metal complex or a heteroaromatic compound) can be used for example. As the electron donor, a substance showing an electron donating property to the organic compound may be used, and preferable specific examples thereof include an alkali metal, an alkaline-earth metal, and a rare-earth metal such as lithium, cesium, magnesium, calcium, erbium, and ytterbium. Further, alkali metal oxide or alkaline-earth metal oxide such as lithium oxide ($LiO_x$), calcium oxide ($CaO_x$), barium oxide ($BaO_x$), or the like can be used. Lewis base such as magnesium oxide can also be used. In addition, an organic compound such as tetrathiafulvalene (abbreviation: TTF) can also be used.

In the foregoing light-emitting element of the present invention, each of the hole injecting layer 111, the hole transporting layer 112, the light-emitting layer 113, the electron transporting layer 114, and the electron injecting layer 115 may be formed by sputtering, evaporation, ink jetting, or coating. In addition, each of the first electrode 101 and the second electrode 102 may also be formed by sputtering, evaporation, or the like, or a wet method such as ink jetting or coating.

Embodiment Mode 3

The light-emitting element of the present invention may have a plurality of light-emitting layers. A plurality of light-emitting layers are provided and then each of them emits light. Accordingly, light that is a combination of light emitted from the plurality of light-emitting layers can be obtained; for example, white light can be obtained. In Embodiment Mode 3, a light-emitting element having a plurality of light-emitting layers will be described with reference to FIG. 2.

Figure 2:
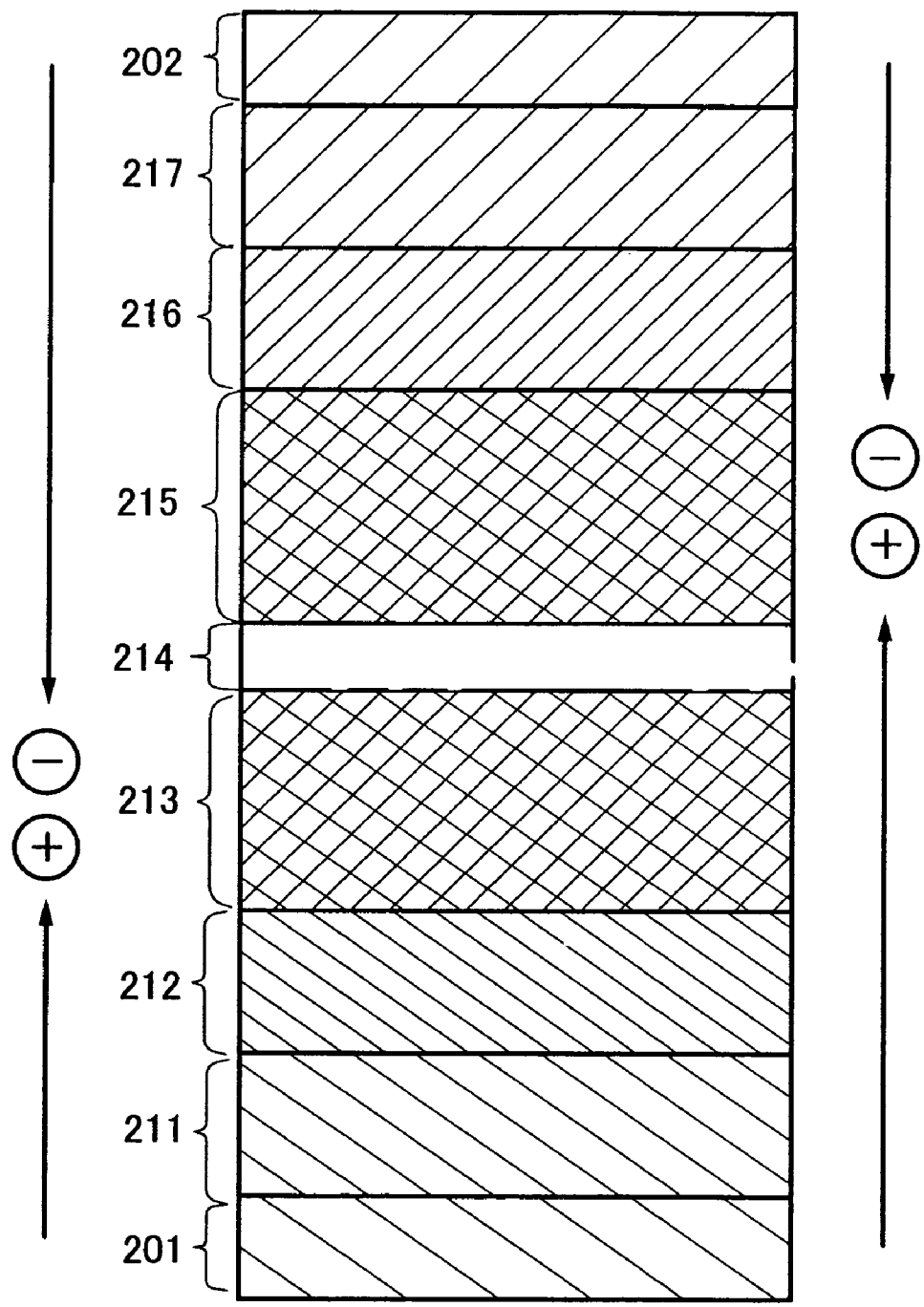
FIG. 2 is a view illustrating a light-emitting element of the present invention.

In FIG. 2, a first light-emitting layer 213 and a second light-emitting layer 215 are provided between a first electrode 201 and a second electrode 202. Light that is a combination of light emitted from the first light-emitting layer 213 and light emitted from the second light-emitting layer 215 are mixed can be obtained. A separation layer 214 is preferably formed between the first light-emitting layer 213 and the second light-emitting layer 215.

When voltage is applied so that the potential of the first electrode 201 is higher than the potential of the second electrode 202, current flows between the first electrode 201 and the second electrode 202, and holes and electrons are recombined with each other in the first light-emitting layer 213, the second light-emitting layer 215, or the separation layer 214. The generated excitation energy is distributed to the first light-emitting layer 213 and the second light-emitting layer 215 to bring each of a first light-emitting substance contained in the first light-emitting layer 213 and a second light-emitting substance contained in the second light-emitting layer 215 to an excited state. Then, the first and second light-emitting substances in the excited state emit light when returning to the ground state.

The first light-emitting layer 213 includes the first light-emitting substance typified by a fluorescent compound such as perylene, 2,5,8,11-tetra(tert-butyl)perylene (abbreviation: TBP), 4,4'-bis(2,2-diphenylvinyl)biphenyl (abbreviation: DPVBi), 4,4'-bis[2-(9-ethylcarbazol-3-yl)vinyl]biphenyl (abbreviation: BCzVBi), bis(2-methyl-8-quinolinolato)(4-phenylphenolato)aluminum (abbreviation: BAlq), or bis(2-methyl-8-quinolinolato)galliumchloride (abbreviation: Gamq$_2$Cl); or a phosphorescent compound such as bis{2-[3', 5'-bis(trifluoromethyl)phenyl]pyridinato-N,C$^{2'}$}iridium(III) picolinate (abbreviation: Ir(CF$_3$ppy)$_2$(pic)), bis[2-(4',6'-difluorophenyl)pyridinato-N,C$^{2'}$]iridium(III)acetylacetonate (abbreviation: FIr(acac)), bis[2-(4',6'-difluorophenyl)pyridinato-N,C$^{2'}$]iridium(III)picolinate (abbreviation: FIrpic), or bis[2-(4',6'-difluorophenyl)pyridinato-N,C$^{2'}$]iridium(III) tetra(1-pyrazolyl)borate (abbreviation: FIr$_6$), from which light emission with a peak at 450 to 510 nm in an emission spectrum (i.e., blue light to blue green light) can be obtained. When the first light-emitting substance is a fluorescent compound, the first light-emitting layer 213 may preferably have a structure in which a substance having a larger singlet excitation energy than the first light-emitting substance is used as a first host and the first light-emitting substance is dispersed as a guest. Alternatively, when the first light-emitting substance is a phosphorescent compound, the first light-emitting layer 213 preferably has a structure in which a substance having a larger triplet excitation energy than the first light-emitting substance is used as a first host and the first light-emitting substance is dispersed as a guest. As the first host, 9,10-di(2-naphthyl)anthracene (abbreviation: DNA), 2-tert-butyl-9,10-di(2-naphthyl)anthracene (abbreviation: t-BuDNA) or the like can be used as well as NPB, CBP, TCTA, or the like that are described above. It is noted that the singlet excitation energy refers to an energy difference between a ground state and a singlet excited state, and the triplet excitation energy refers to an energy difference between a ground state and a triplet excited state.

The second light-emitting layer 215 includes the organometallic complex of the present invention to emit red light. Further, since the organometallic complex of the present invention has high emission efficiency, a light-emitting element with high emission efficiency can be obtained. Further, a light-emitting element with capability of long-time driving can be obtained. Moreover, a light-emitting element with low power consumption can be obtained.

The second light-emitting layer 215 may have a similar structure to the light-emitting layer 113 described above in Embodiment Mode 2.

Specifically, the separation layer 214 can be formed using TPAQn, NPB, CBP, TCTA, Znpp$_2$, ZnBOX, or the like which are described above. The separation layer 214 is provided in this manner, and therefore a defect that emission intensity of one of the first light-emitting layer 213 and the second light-emitting layer 215 is stronger than that of the other thereof can be prevented. However, the separation layer 214 is not necessarily provided, and it may be provided as appropriate such that the ratio between emission intensities of the first light-emitting layer 213 and the second light-emitting layer 215 can be adjusted.

In Embodiment Mode 3, the organometallic complex of the present invention is used for the second light-emitting layer 215 and another light-emitting substance is used for the first light-emitting layer 213, whereas the organometallic complex of the present invention may be used for the first light-emitting layer 213 and another light-emitting substance may be used for the second light-emitting layer 215.

In Embodiment Mode 3, a light-emitting element including two light-emitting layers is described as illustrated in FIG. 2; however, the number of light-emitting layers is not limited to two, and may be three, for example. Light emitted from each light-emitting layer may be mixed. Consequently, white-color light can be obtained, for example.

The first electrode 201 may have a similar structure to the first electrode 101 described above in Embodiment Mode 2. The second electrode 202 may also have a similar structure to the second electrode 102 described above in Embodiment Mode 2.

In Embodiment Mode 3, as illustrated in FIG. 2, a hole injecting layer 211, a hole transporting layer 212, an electron transporting layer 216, and an electron injecting layer 217 are provided. As to structures of these layers, the structures of the respective layers described in Embodiment Mode 2 may be applied. However, these layers are not necessarily provided and may be provided depending on the element characteristics.

Embodiment Mode 4

Embodiment Mode 4 will exemplify a light-emitting element in which a plurality of light-emitting layers are provided and light is emitted from each of these layers with a different element structure from that in Embodiment Mode 3. Therefore, also in Embodiment Mode 4, light that is a combination of light emitted from a plurality of light-emitting layers can be obtained; that is, white-color light can be obtained, for example. Hereinafter, explanation will be made with reference to FIG. 3.

Figure 3:
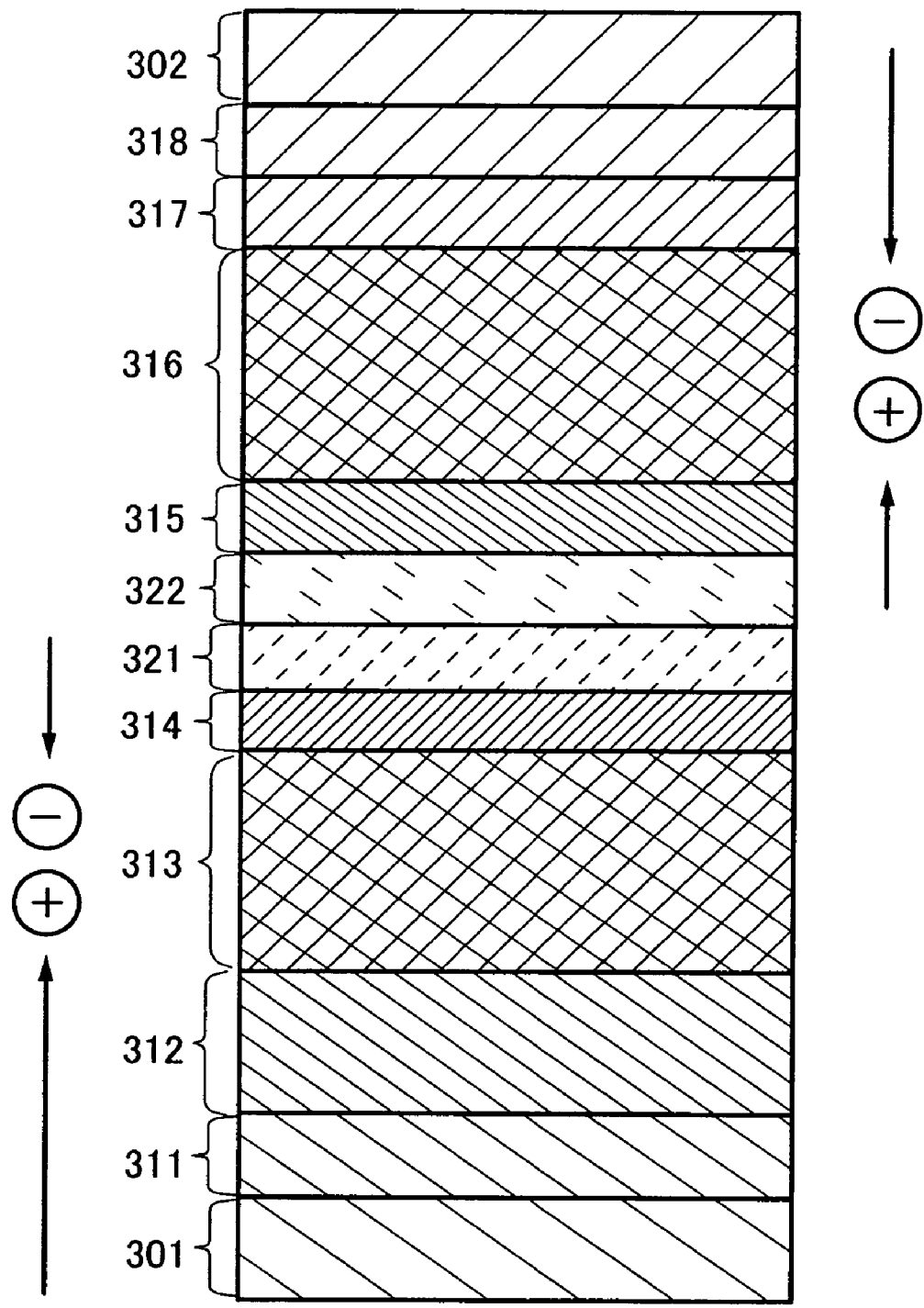
FIG. 3 is a view illustrating a light-emitting element of the present invention.

In the light-emitting element of FIG. 3, a first light-emitting layer 313 and a second light-emitting layer 316 are provided between a first electrode 301 and a second electrode 302. An N layer 321 and a P layer 322 are provided as charge generating layers between the first light-emitting layer 313 and the second light-emitting layer 316.

The N layer 321 is a layer that generates electrons, and the P layer 322 is a layer that generates holes. When voltage is applied such that the potential of the first electrode 301 is higher than that of the second electrode 302, holes injected from the first electrode 301 and electrons injected from the N layer 321 are recombined with each other in the first light-emitting layer 313, and thus a first light-emitting substance contained in the first light-emitting layer 313 emits light. Further, electrons injected from the second electrode 302 and holes injected from the P layer 322 are recombined with each other in the second light-emitting layer 316, and thus a second light-emitting substance contained in the second light-emitting layer 316 emits light.

The first light-emitting layer 313 may have a similar structure to the first light-emitting layer 213 of Embodiment Mode 3, and light with a peak of emission spectrum at 450 nm to 510 nm (i.e., blue light to blue green light) can be obtained. The second light-emitting layer 316 may have a similar structure to the second light-emitting layer 215 of Embodiment Mode 3, and includes the organometallic complex of the present invention to emit red light. Since the organometallic complex of the present invention has high emission efficiency, a light-emitting element with high emission efficiency can be obtained. Further, a light-emitting element with low power consumption can be obtained.

Since the N layer 321 is a layer that generates electrons, it may be formed using the composite material of the organic compound and the electron donor described above in Embodiment Mode 2. With such a structure, electrons can be injected to the first light-emitting layer 313 side.

Since the P layer 322 is a layer that generates holes, it may be formed using the composite material of the organic compound and the electron acceptor described above in Embodiment Mode 2. With such a structure, holes can be injected to the second light-emitting layer 316 side. For the P layer 322, metal oxide having an excellent hole injecting property, such as molybdenum oxide, vanadium oxide, ITO, or ITSO, can be used.

Here, Embodiment Mode 4 describes a light-emitting element in which the two light-emitting layers are provided as illustrated in FIG. 3; however, the number of light-emitting layers is not limited to two, and may be three, for example. Light emitted from each light-emitting layer may be mixed. Consequently, white-color light can be obtained, for example.

The first electrode 301 may have a similar structure to the first electrode 101 described above in Embodiment Mode 2. The second electrode 302 may also have a similar structure to the second electrode 102 described above in Embodiment Mode 2.

In Embodiment Mode 4, as illustrated in FIG. 3, a hole injecting layer 311, hole transporting layers 312 and 315, electron transporting layers 314 and 317, and an electron injecting layer 318 are provided. As to structures of these layers, the structures of the respective layers described above in Embodiment Mode 2 may also be applied. However, these layers are not necessarily provided and may be provided as appropriate depending on the element characteristics.

Embodiment Mode 5

In Embodiment Mode 5, a mode of a light-emitting element including the organometallic complex of the present invention as a sensitizer will be described with reference to FIG. 1.

FIG. 1 illustrates the light-emitting element including the light-emitting layer 113 between the first electrode 101 and the second electrode 102. The light-emitting layer 113 includes the organometallic complex of the present invention as described above in Embodiment Mode 1, and a fluorescent compound that can emit light with a longer wavelength than the organometallic complex of the present invention.

In such a light-emitting element, holes injected from the first electrode 101 and electrons injected from the second electrode 102 are recombined with each other in the light-emitting layer 113 to bring the fluorescent compound to an excited state. Then, light is emitted when the fluorescent compound in the excited state returns to the ground state. At this time, the organometallic complex of the present invention acts as a sensitizer for the fluorescent compound to make more molecules of the fluorescent compound be in the singlet excited state. In this manner, a light-emitting element with excellent emission efficiency can be obtained by using the organometallic complex of the present invention as a sensitizer. It is to be noted that the first electrode 101 and the second electrode 102 function as an anode and as a cathode, respectively, in the light-emitting element of Embodiment Mode 5.

The light-emitting layer 113 includes the organometallic complex of the present invention and the fluorescent compound that can emit light with a longer wavelength than the organometallic complex of the present invention. The light-emitting layer 113 preferably has a structure in which a substance having a larger triplet excitation energy than the organometallic complex of the present invention and a larger singlet excitation energy than the fluorescent compound is used as a host, and the organometallic complex of the present invention and the fluorescent compound are dispersed as a guest.

There are no particular limitations on the substance used for dispersing the organometallic complex of the present invention and the fluorescent compound (i.e., host), and the substances given above as examples of the host in Embodiment Mode 2, or the like can be used.

Although there are also no particular limitations on the fluorescent compound, a preferable example thereof is a compound that can emit red light to infrared light, such as 4-dicyanomethylene-2-isopropyl-6-[2-(1,1,7,7-tetramethyljulolidin-9-yl)ethenyl]-4H-pyran (abbreviation: DCJTI), magnesium phthalocyanine, magnesium porphyrin, phthalocyanine, or the like.

The first electrode 101 and the second electrode 102 may have similar structures to those described above in Embodiment Mode 2.

In Embodiment Mode 5, as illustrated in FIG. 1, the hole injecting layer 111, the hole transporting layer 112, the electron transporting layer 114, and the electron injecting layer 115 are provided. As to structures of these layers also, the structures of the respective layers described above in Embodiment Mode 2 may be applied. However, these layers are not necessarily needed and may be provided as appropriate depending on the element characteristics.

Light emission with high efficiency can be obtained from the above-described light-emitting element by using the organometallic complex of the present invention as a sensitizer.

Embodiment Mode 6

In Embodiment Mode 6, a light-emitting device manufactured using the organometallic complex of the present invention will be described.

In Embodiment Mode 6, a light-emitting device manufactured using the organometallic complex of the present invention will be described with reference to FIGS. 4A and 4B. FIG. 4A is a top view of the light-emitting device, and FIG. 4B is a cross sectional view of FIG. 4A taken along a line A-A'. Reference numeral 401 denotes a driver circuit portion (source side driver circuit); 402 denotes a pixel portion; and 403 denotes a driver circuit portion (gate side driver circuit), which are indicated by dotted lines. Reference numeral 404 denotes a sealing substrate; 405 denotes a sealing material; and 407 denotes a space surrounded by the sealing material 405.

A lead wiring 408 is a wiring to transmit a signal to be inputted to the source side driver circuit 401 and the gate side driver circuit 403, and receives a video signal, a clock signal, a start signal, a reset signal, and the like from a flexible printed circuit (FPC) 409 which serves as an external input terminal. It is to be noted that, although only an FPC is illustrated here, this FPC may be provided with a printed wiring board (PWB). The light-emitting device in this specification includes, in its category, not only a light-emitting device itself but also a light-emitting device attached with an FPC or a PWB.

Next, a cross-sectional structure is described with reference to FIG. 4B. Although the driver circuit portions and the pixel portion 402 having a plurality of pixels are formed over a substrate 410, the source side driver circuit 401 which is one of the driver circuit portions and one of the plurality of pixels in the pixel portion 402 are illustrated here.

A CMOS circuit that is a combination of an n-channel TFT 423 and a p-channel TFT 424 is formed as the source side driver circuit 401. Each driver circuit portion may be any one of various circuits such as a CMOS circuit, a PMOS circuit, and an NMOS circuit. Although a driver integration type in which a driver circuit is formed over a substrate is described in this embodiment mode, a driver circuit is not necessarily formed over a substrate and can be formed outside a substrate.

The pixel portion 402 has the plurality of pixels, each of which includes a switching TFT 411, a current control TFT 412, and a first electrode 413 which is electrically connected to the drain of the current control TFT 412. It is to be noted that an insulator 414 is formed so as to cover an end portion of the first electrode 413. Here, a positive photosensitive acrylic resin film is used for the insulator 414.

The insulator 414 is formed so as to have a curved surface having curvature at an upper end portion or a lower end portion thereof in order to obtain favorable coverage. For example, in a case of using a positive photosensitive acrylic resin as a material for the insulator 414, the insulator 414 is preferably formed so as to have a curved surface with a curvature radius (0.2 μm to 3 μm) only at the upper end portion thereof. Either a negative type that becomes insoluble in an etchant by light or a positive type that becomes soluble in an etchant by light can be used as the insulator 414.

A layer 416 containing a light-emitting substance and a second electrode 417 are formed over the first electrode 413. Here, a material having a high work function is preferable as a material used for the first electrode 413 to serve as an anode. For example, the first electrode 413 can be formed using a stacked layer of a titanium nitride film and a film containing aluminum as its main component; a three-layer structure of a titanium nitride film, a film containing aluminum as its main component, and another titanium nitride film; or the like, as well as a single-layer film such as an indium tin oxide (ITO) film, an indium tin oxide film containing silicon, an indium zinc oxide (IZO) film, a titanium nitride film, a chromium film, a tungsten film, a Zn film, or a Pt film. When the first electrode 413 has a stacked layer structure, it can have low resistance as a wiring, form a favorable ohmic contact, and further function as an anode.

The layer 416 containing a light-emitting substance is formed by various methods such as evaporation using an evaporation mask, ink jetting, and spin coating. The layer 416 containing a light-emitting substance includes the organometallic complex of the present invention, described in Embodiment Mode 1, as a part. As a material to be combined therewith, a low molecular material, a medium molecular material (inclusive of oligomer and dendrimer), or a high molecular material may be used. Although a single layer or a stacked layer of an organic compound is generally used as the layer 416 containing a light-emitting substance, the present invention may include a structure in which an organic compound film containing an inorganic compound is used as the layer 416 containing a light-emitting substance.

As a material used for the second electrode 417 to be formed over the layer 416 containing a light-emitting substance, a material having a low work function (Al, Ag, Li, Ca, or an alloy or a compound of them, such as MgAg, MgIn, AlLi, LiF, $CaF_2$, calcium nitride, or calcium fluoride) is preferably used. In a case where light emitted from the layer 416 containing a light-emitting substance is transmitted through the second electrode 417 which serves as a cathode, a stacked layer of a metal thin film with reduced film thickness and a transparent conductive film (formed using an indium oxide-tin oxide alloy (ITO), an indium oxide-zinc oxide alloy ($In_2O_3$—ZnO), zinc oxide (ZnO), or the like) is preferably used as the second electrode 417.

Attachment of the sealing substrate 404 to the substrate 410 with the sealing material 405 makes a structure in which a light-emitting element 418 is provided in the space 407 surrounded by the substrate 410, the sealing substrate 404, and the sealing material 405. It is to be noted that there is also a structure in which the space 407 is filled with the sealing material 405 as well as a structure in which the space 407 is filled with an inert gas (e.g., nitrogen or argon).

An epoxy-based resin is preferably used as the sealing material 405. The material desirably allows as little moisture and oxygen as possible to penetrate. As the sealing substrate 404, a plastic substrate made of fiberglass-reinforced plastics (FRP), polyvinyl fluoride (PVF), polyester, an acrylic resin, or the like can be used besides a glass substrate or a quartz substrate.

In the above-described manner, a light-emitting device manufactured using the organometallic complex of the present invention can be obtained.

The light-emitting device of the present invention includes the organometallic complex described in Embodiment Mode 1 to have favorable characteristics. Specifically, since the light-emitting element with high emission efficiency is included, a light-emitting device with low power consumption and capability of long-time driving can be obtained. Further, since red light emission with high luminous efficiency can be realized, a light-emitting device with low power consumption and excellent color reproducibility, which is suitable for a full-color display, can be obtained.

Figure 5A:
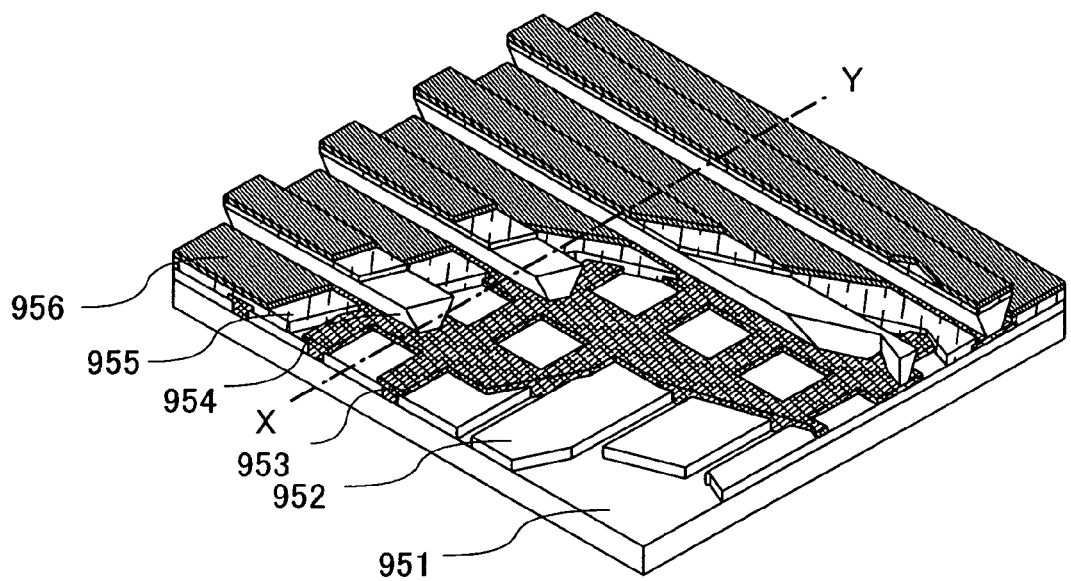
FIGS. 5A and 5B are views illustrating a light-emitting device of the present invention.
Figure 5B:
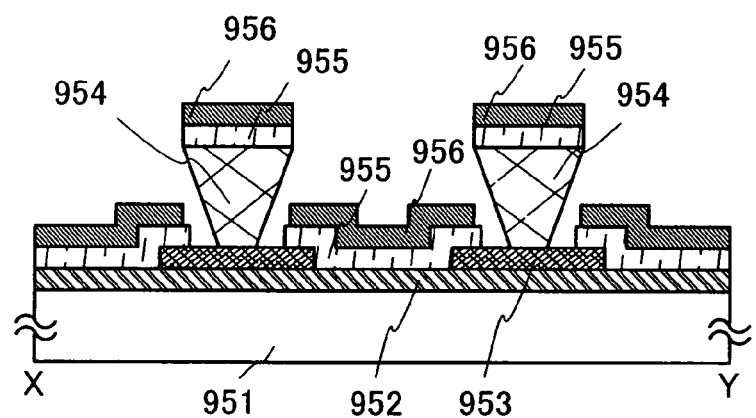

Although, as described above, description is made of an active matrix light-emitting device that controls driving of a light-emitting element with transistors, the present invention may include a passive matrix light-emitting device that drives a light-emitting element without particularly providing an element for driving such as a transistor. FIGS. 5A and 5B illustrate a passive matrix light-emitting device manufactured by using the present invention. FIG. 5A is a perspective view illustrating the passive matrix light-emitting device and FIG.

5B is a cross sectional view of FIG. 5A taken along a line X-Y. In FIGS. 5A and 5B, an electrode 952 and an electrode 956 are provided over a substrate 951, and a layer 955 containing a light-emitting substance is provided between the electrodes 952 and 956. An end portion of the electrode 952 is covered with an insulating layer 953. A partition layer 954 is provided over the insulating layer 953. Side walls of the partition layer 954 slope so that a distance between one side wall and the other side wall becomes narrower toward a substrate surface. That is, a cross section of the partition layer 954 in the direction of a short side is trapezoidal, and a base (side that is provided in the same direction as a plane direction of the insulating layer 953 and in contact with the insulating layer 953) is shorter than the upper side (side that is provided in the same direction as the plane direction of the insulating layer 953 and not in contact with the insulating layer 953). By providing the partition layer 954 in this manner, a defect of the light-emitting element caused by static electricity or the like can be prevented.

Embodiment Mode 7

In Embodiment Mode 7, electronic devices of the present invention each including the light-emitting device described in Embodiment Mode 6 will be described. The electronic devices of the present invention each include the organometallic complex described in Embodiment Mode 1 to include a display portion with high emission efficiency, low power consumption, and capability of long-time driving. Further, the electronic devices of the present invention each include a display portion having excellent color reproducibility.

The electronic devices each including the light-emitting element manufactured using the organometallic complex of the present invention include cameras such as video cameras or digital cameras, goggle type displays, navigation systems, audio reproducing devices (e.g., car audio components and audio components), computers, game machines, portable information terminals (e.g., mobile computers, mobile phones, portable game machines, and electronic books), and image reproducing devices provided with a recording medium (specifically, devices capable of reproducing a recording medium such as a digital versatile disc (DVD) and provided with a display device that can display the image), and the like. Specific examples of these electronic devices are illustrated in FIGS. 6A to 6D.

Figure 6A:
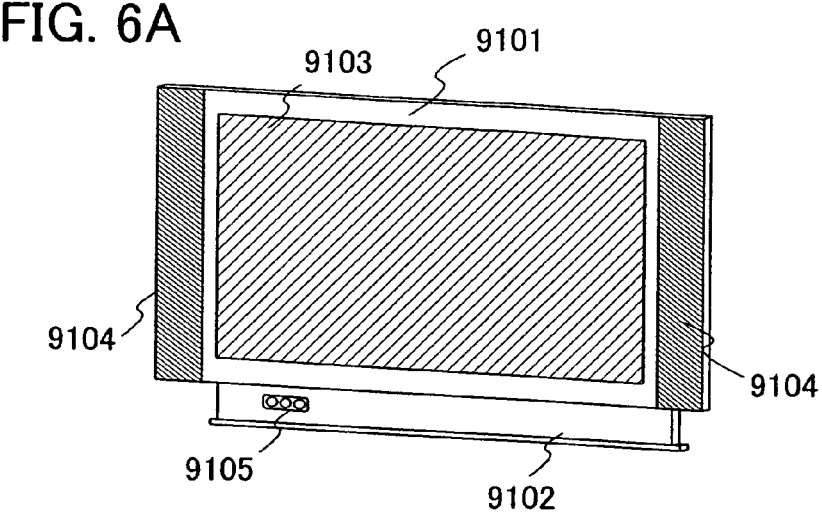
FIGS. 6A to 6D are views illustrating electronic devices of the present invention.

FIG. 6A illustrates a television set according to the present invention. The television set includes a chassis 9101, a supporting base 9102, a display portion 9103, a speaker portion 9104, a video input terminal 9105, and the like. In the television set, the display portion 9103 has a matrix arrangement of light-emitting elements that are similar to those described in Embodiment Modes 2 to 5. The light-emitting elements are characterized by high emission efficiency and excellent color reproducibility. The display portion 9103 including the light-emitting elements has similar features and enables the television set to emit light with high luminance and to have low power consumption. Accordingly, the television set according to the present invention, which achieves low power consumption and high image quality, can be provided as a product that is suitable for any residential environment.

Figure 6B:
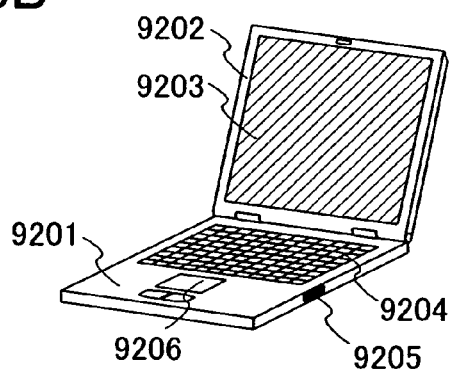

FIG. 6B illustrates a computer according to the present invention. The computer includes a main body 9201, a chassis 9202, a display portion 9203, a keyboard 9204, an external connection port 9205, a pointing device 9206, and the like. In this computer, the display portion 9203 has a matrix arrangement of light-emitting elements that are similar to those described in Embodiment Modes 2 to 5. The light-emitting elements are characterized by high emission efficiency and excellent color reproducibility. The display portion 9203 including the light-emitting elements has similar features to achieve light emission with high luminance and the decrease in power consumption. Accordingly, the computer according to the present invention, which achieves low power consumption and high image quality, can be provided as a product that is suitable for the environment.

Figure 6C:
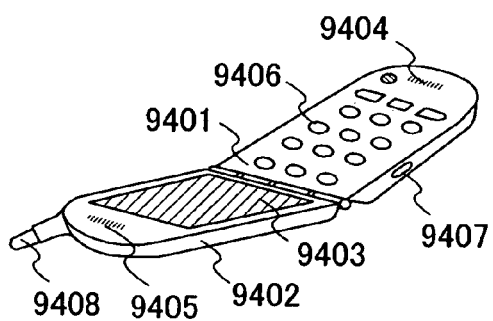

FIG. 6C illustrates a mobile phone according to the present invention. The mobile phone includes a main body 9401, a chassis 9402, a display portion 9403, an audio input portion 9404, an audio output portion 9405, operation keys 9406, an external connection port 9407, an antenna 9408, and the like. In the mobile phone, the display portion 9403 has a matrix arrangement of light-emitting elements that are similar to those described in Embodiment Modes 2 to 5. The light-emitting elements are characterized by high emission efficiency and excellent color reproducibility. The display portion 9403 including the light-emitting elements has similar features to achieve light emission with high luminance and the decrease in power consumption. Accordingly, the mobile phone according to the present invention, which achieves low power consumption and high image quality, can be provided as a product that is suitable for portable use.

Figure 6D:
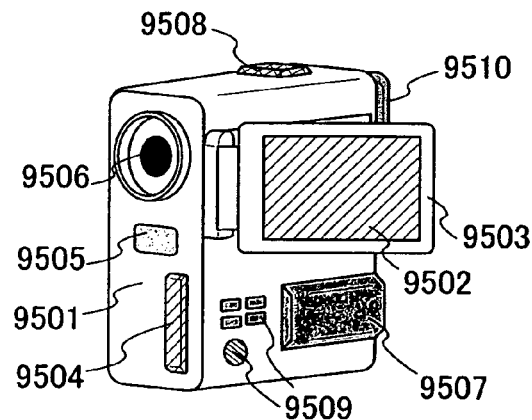

FIG. 6D illustrates a camera according to the present invention. The camera includes a main body 9501, a display portion 9502, a chassis 9503, an external connection port 9504, a remote control receiving portion 9505, an image receiving portion 9506, a battery 9507, an audio input portion 9508, operation keys 9509, an eye piece portion 9510, and the like. In this camera, the display portion 9502 has a matrix arrangement of light-emitting elements that are similar to those described in Embodiment Modes 2 to 5. The light-emitting elements are characterized by high emission efficiency, capability of long-time driving, and excellent color reproducibility. The display portion 9502 including the light-emitting elements has similar features to achieve light emission with high luminance and the decrease in power consumption. Accordingly, the camera according to the present invention, which achieves low power consumption and high image quality, can be provided as a product that is suitable for portable use.

As described above, the applicable range of the light-emitting device of the present invention is so wide that the light-emitting device can be applied to electronic devices in various fields. By using the organometallic complex of the present invention, electronic devices that each have a display portion with high emission efficiency, capability of long-time driving, and low power consumption can be provided. Further, electronic devices including a display portion having excellent color reproducibility can be provided.

The light-emitting device of the present invention can also be used as a lighting device. One mode using the light-emitting element of the present invention as a lighting device will be described with reference to FIG. 7.

Figure 7:
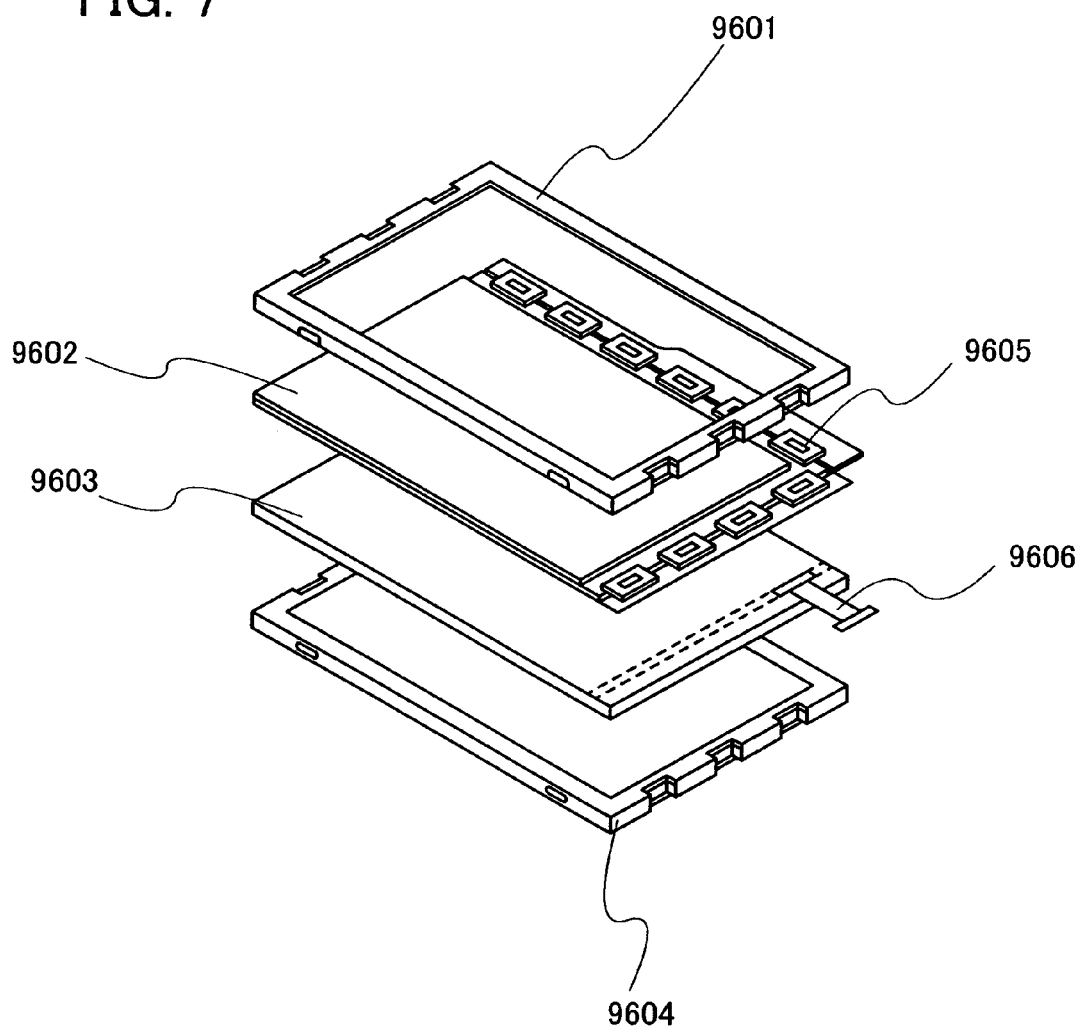
FIG. 7 is a view illustrating an electronic device of the present invention.

FIG. 7 illustrates an example of a liquid crystal display device using the light-emitting device of the present invention as a backlight. The liquid crystal display device illustrated in FIG. 7 includes a chassis 9601, a liquid crystal layer 9602, a backlight 9603, and a chassis 9604, and the liquid crystal layer 9602 is connected to a driver IC 9605. The light-emitting device of the present invention is used as the backlight 9603, and current is supplied through a terminal 9606.

By using the light-emitting device of the present invention as a backlight of a liquid crystal display device, the backlight can achieve high emission efficiency and low power consumption. The light-emitting device of the present invention is a lighting device with plane light emission, and can have a large area. Therefore, the backlight can have a large area, and thus a liquid crystal display device having a large area can be realized. Furthermore, the light-emitting device of the present invention has a thin shape and consumes low power, and thus a thin shape and low power consumption of a display device can also be realized. Moreover, the light-emitting device of the present invention can emit light with high luminance, and thus the liquid crystal display device including the light-emitting device of the present invention can also emit light with high luminance.

Figure 8:
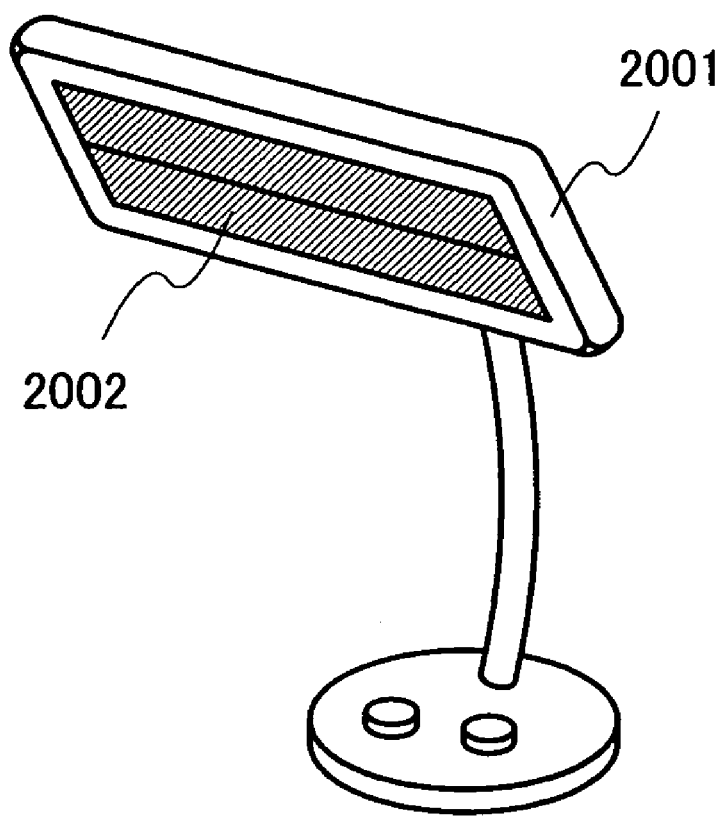
FIG. 8 is a view illustrating a lighting device of the present invention.

FIG. 8 illustrates an example of using the light-emitting device to which the present invention is applied as a table lamp that is a lighting device. The table lamp illustrated in FIG. 8 includes a chassis 2001 and a light source 2002 to which the light-emitting device of the present invention is applied. The light-emitting device of the present invention achieves high emission efficiency, capability of long-time driving, and low power consumption, and thus the table lamp also achieves high emission efficiency, capability of long-time driving, and low power consumption.

Figure 9:
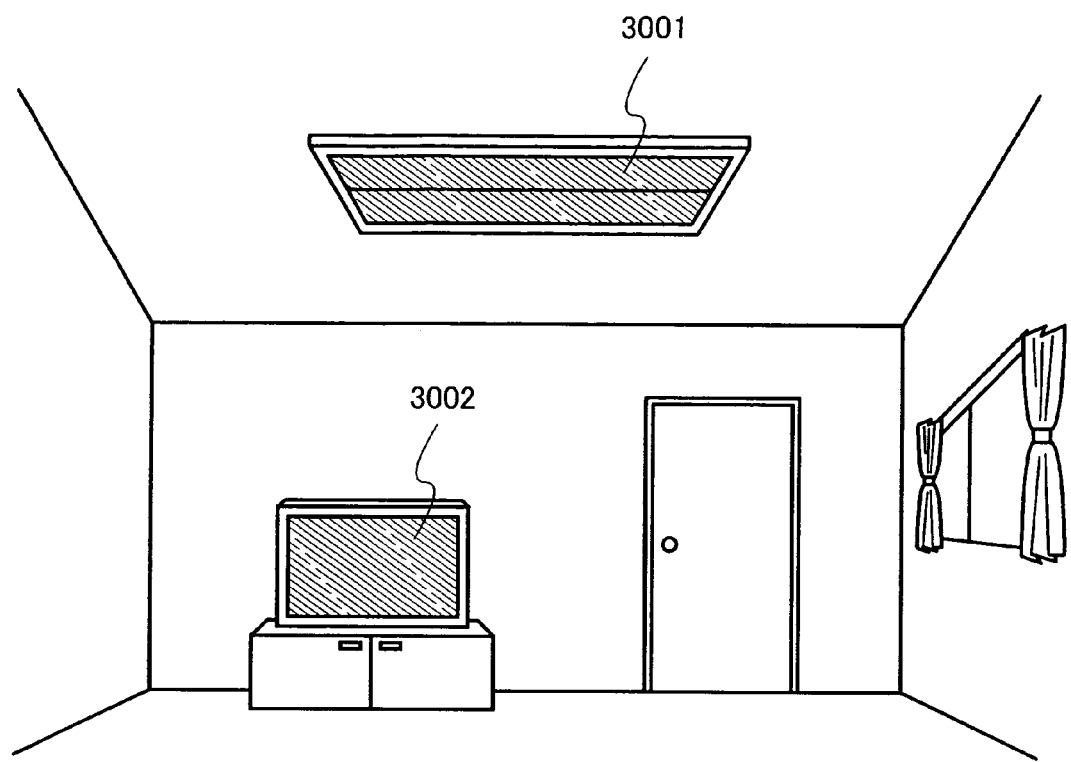
FIG. 9 is a view illustrating a lighting device of the present invention.

FIG. 9 illustrates an example of using the light-emitting device to which the present invention is applied as an indoor lighting device 3001. The light-emitting device of the present invention can have a large area, and thus the light-emitting device of the present invention can be used as a lighting device having a large area. Further, the light-emitting device of the present invention has a thin shape and consumes low power, and thus the light-emitting device of the present invention can be used as a lighting device having a thin shape and consuming low power. As described above, in a room where the light-emitting device to which the present invention is applied is used as the indoor lighting device 3001, a television set 3002 according to the present invention as illustrated in FIG. 6A is placed so that public broadcasting and movies can be watched. In such a case, since both of the devices consume low power, a powerful image can be watched in a bright room without concern about electricity charges.

EXAMPLE 1

Synthetic Example 1

Synthetic Example 1 will specifically exemplify a synthetic example of (acetylacetonato)bis(2-phenyldibenzo[f,h]quinoxalinato)iridium(III) (abbreviation: Ir(dbq-P)$_2$(acac)) which is the organometallic complex of the present invention, represented by the structural formula (1) in Embodiment Mode 1.

Step 1: Synthesis of 2-phenyldibenzo[f,h]quinoxaline

Abbreviation: Hdbq-P

First, 2.16 g of phenylglyoxal and 3.36 g of 9,10-diamonophenanthrene were dissolved in a solvent of 100 mL of dehydrated ethanol under nitrogen atmosphere. The solution was refluxed for 7 hours to be reacted. The white power precipitated from the reaction was filtered. The residue was washed with ethanol and then ether to obtain an objective dibenzo[f,h]quinoxaline derivative Hdbq-P (yield: 92%). Synthetic scheme of Step 1 is shown in the following (a-1).

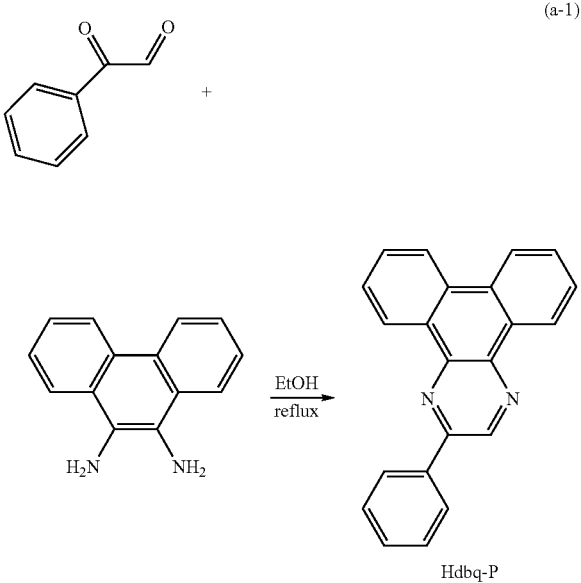

(a-1)

Step 2: Synthesis of di-1-chloro-bis[bis(2-phenyldibenzo[f,h]quinoxalinato)iridium(III)

Abbreviation: [Ir(dbq-P)$_2$Cl]$_2$

Subsequently to Step 1 described above, 24 mL of 2-ethoxyethanol, 8 mL of water, 0.61 g of the dibenzo[f,h]quinoxaline derivative Hdbq-P which was obtained in Step 1, and 0.30 g of iridium chloride hydrate (IrCl$_3$·H$_2$O) (produced by Sigma-Aldrich Corp.) were put in an eggplant type flask with a reflux pipe. The atmosphere in the flask was substituted with argon. Then, the mixture was irradiated with a microwave (2.45 GHz, 200 W) for 5 hours to be reacted. The orange powder precipitated from the reaction solution was filtered, and the residue was washed with ethanol to obtain a dinuclear complex [Ir(dbq-P)$_2$Cl]$_2$ (yield: 78%). It is to be noted that a microwave synthesis system (Discovery, manufactured by CEM Corporation) was used for the microwave irradiation. Synthetic scheme of Step 2 is shown in the following (b-1).

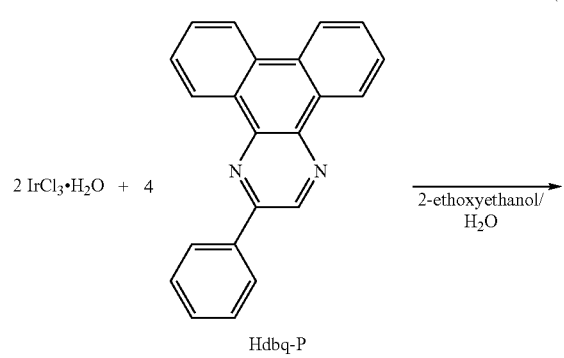

(b-1)

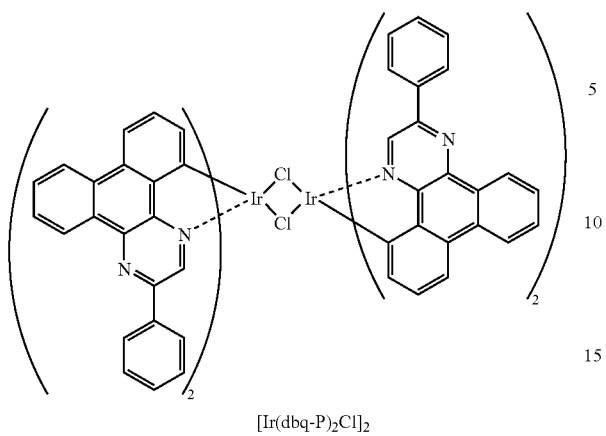

[Ir(dbq-P)₂Cl]₂

Step 3: Synthesis of (acetylacetonato)bis(2-phenyldibenzo[f,h]quinoxalinato)iridium(III)

Abbreviation: Ir(dbq-P)₂(acac)

Subsequently to Step 2 described above, 25 mL of 2-ethoxyethanol, 0.54 g of the dinuclear complex [Ir(dbq-P)₂Cl]₂ which was obtained in Step 2, 0.10 mL of acetylacetone, and 0.34 g of sodium carbonate were put in an eggplant type flask with a reflux pipe. The atmosphere in the flask was substituted with argon. Then, the mixture was irradiated with a microwave (2.45 GHz, 200 W) for 30 minutes to be reacted. The reaction solution was filtered, and the obtained filtrate was condensed and dried to obtain a residue. This residue was recrystallized with dichloromethane to obtain the organometallic complex of the present invention Ir(dbq-P)₂(acac) as a red powder (yield: 16%). Synthetic scheme of Step 3 is shown in the following (c-1).

(c-1)

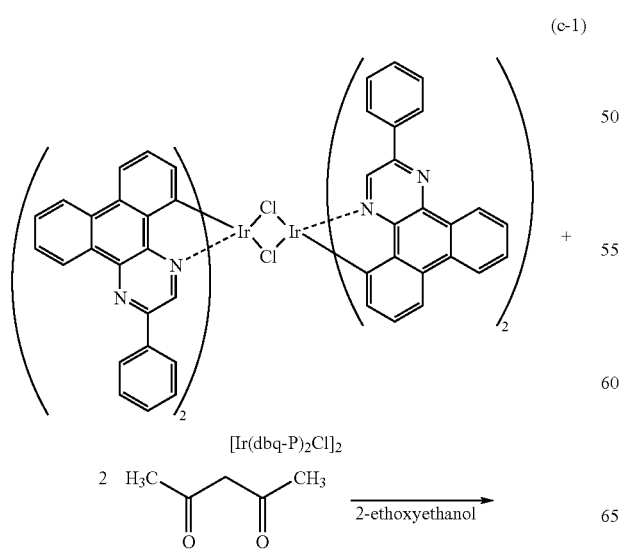

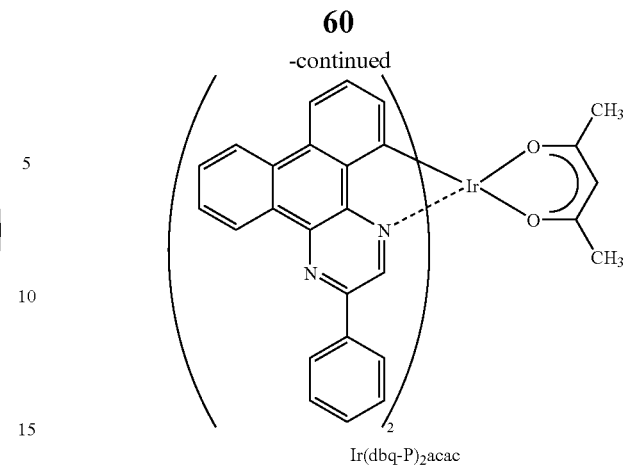

Ir(dbq-P)₂acac

Figure 10:
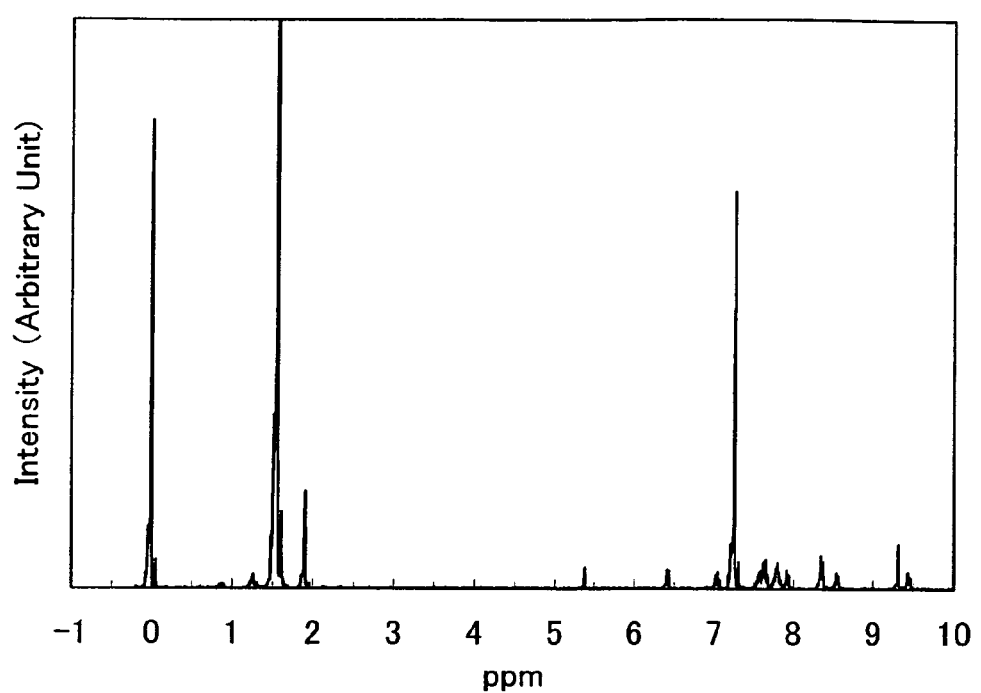
FIG. 10 is a $^1$H-NMR chart of (acetylacetonato)bis(2-phenyldibenzo[f,h]quinoxalinato)iridium(III) which is synthesized in Example 1.

An analysis result by nuclear magnetic resonance spectrometry ($^1$H-NMR) of the red powder obtained in Step 3 is described below. A $^1$H-NMR chart is illustrated in FIG. 10. It is found that the organometallic complex of the present invention Ir(dbq-P)₂(acac) represented by the above structural formula (1) was obtained in Synthetic Example 1.

$^1$H-NMR. δ (CDCl₃): 1.90 (s, 6H), 5.38 (s, 1H), 6.43 (d, 2H), 7.05 (t, 2H), 7.65 (m, 8H), 7.80 (m, 4H), 7.93 (d, 2H), 8.36 (d, 4H), 8.55 (d, 2H), 9.32 (s, 1H), 9.45 (d, 2H).

The decomposition temperature of the obtained organometallic complex of the present invention Ir(dbq-P)₂(acac) was measured by a high vacuum differential type differential thermal balance (manufactured by Bruker AXS K. K., TG/DTA2410SA). The temperature was increased at a rate of 10° C./min; as a result, the gravity decreases by 5% at 336° C. to show a favorable heat resistance.

Figure 11:
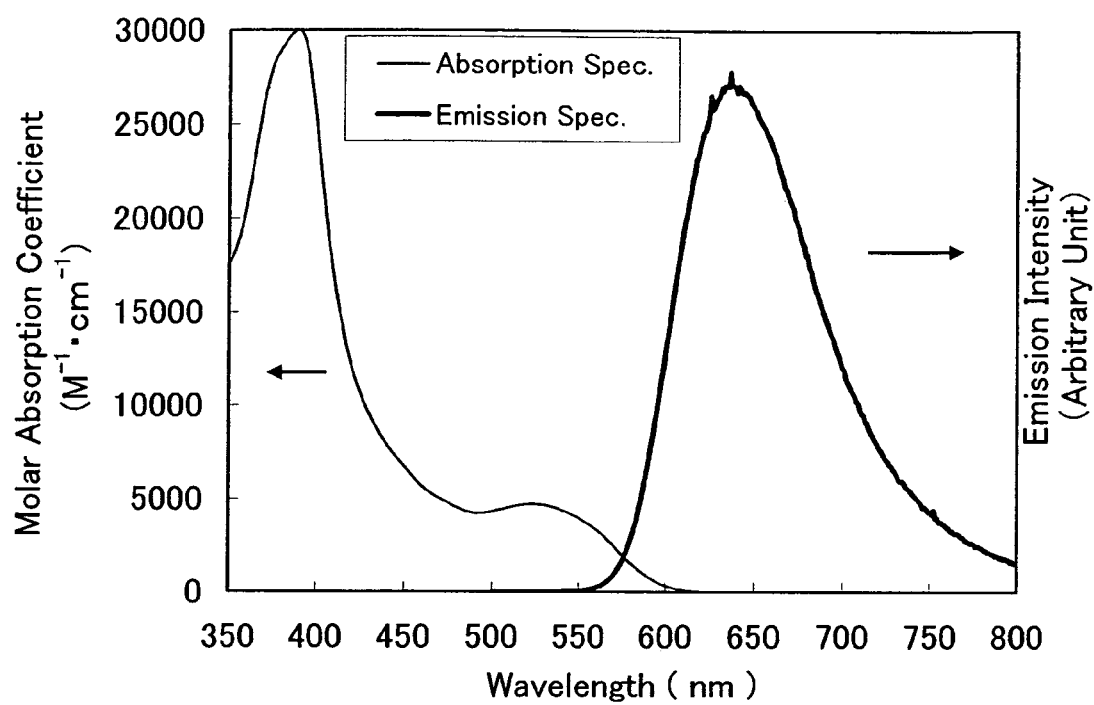
FIG. 11 is a graph illustrating an absorption spectrum and an emission spectrum of (acetylacetonato)bis(2-phenyldibenzo[f,h]quinoxalinato)iridium(III) which is synthesized in Example 1.

Next, an absorption spectrum of Ir(dbq-P)₂(acac) was measured with the use of an ultraviolet-visible light spectrophotometer (manufactured by Japan Spectroscopy Corporation, V550 type). The measurement was conducted by using a dichloromethane solution (0.091 mmol/L) at room temperature. Further, an emission spectrum of Ir(dbq-P)₂(acac) was measured with the use of a fluorescence spectrophotometer (manufactured by Hamamatsu Photonics Corporation, FS920). The measurement was conducted by using a degassed dichloromethane solution (0.32 mmol/L) at room temperature. FIG. 11 illustrates the measurement results. The horizontal axis indicates a wavelength and the vertical axis indicates a molar absorption coefficient and an emission intensity.

As illustrated in FIG. 11, the organometallic complex of the present invention Ir(dbq-P)₂(acac) has a peak of emission spectrum at 640 nm, and red light was observed from the solution.

EXAMPLE 2

Synthetic Example 2

Synthetic Example 2 will specifically exemplify a synthetic example of (acetylacetonato)bis[(2-(3-fluorophenyl)-dibenzo[f,h]quinoxalinato)iridium(III) (abbreviation: Ir(dbq-3FP)₂(acac) which is the organometallic complex of the present invention, included in the general formula (G1) in Embodiment Mode 1 and represented by the following structural formula (55).

(55)

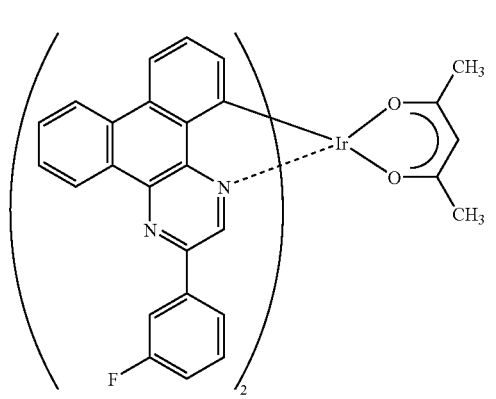

Step 1: Synthesis of 2-(3-fluorophenyl)-dibenzo[f,h]quinoxaline

Abbreviation: Hdbq-3FP

First, 27.5 mL of a hexane solution of n-butyllithium (1.58 mol/L) was dropped in a mixed solution of 6.87 g of 3-bromofluorobenzene and 40 mL of tetrahydrofuran at −78° C. under nitrogen atmosphere, and immediately after that, the obtained solution was stirred at −78° C. for 2 hours. To this solution was added 7.54 g of dibenzo[f,h]quinoxaline at −78° C. in five separate additions. The reaction temperature was increased to room temperature, and then the solution was stirred at room temperature for 12 hours. Water was added to this mixture, and an organic layer was extracted with dichloromethane used as an extraction solvent. The obtained organic layer was dried over anhydrous magnesium sulfate. The dried solution was filtered. After the solvent of this solution was distilled, the resultant substance was recrystallized with ethanol to obtain an objective quinoxaline derivative Hdbq-3FP (light orange power, yield 23%). Synthetic scheme of Step 1 is shown in the following (a-2).

(a-2)

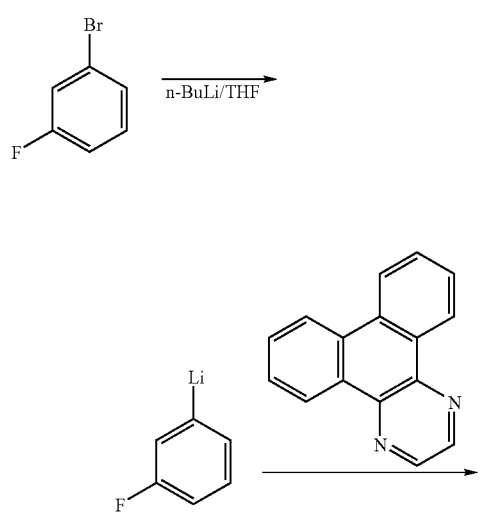

Step 2: Synthesis of di-μ-chloro-bis[bis{2-(3-fluorophenyl)-dibenzo[f,h]quinoxalinato}iridium(III)

Abbreviation: [Ir(dbq-3FP)$_2$Cl]$_2$

Subsequently to Step 1 described above, 15 mL of 2-ethoxyethanol, 5 mL of water, 2.41 g of the quinoxaline derivative Hdbq-3FP which was obtained in Step 1, and 1.01 g of iridium chloride hydrate (IrCl$_3$.H$_2$O) (produced by Sigma-Aldrich Corp.) were put in an eggplant type flask with a reflux pipe. The atmosphere in the flask was substituted with argon. Then, the mixture was irradiated with a microwave (2.45 GHz, 100 to 250 W) for 6 hours to be reacted. The orange powder precipitated from the reaction solution was filtered, and the residue was washed with ethanol to obtain a dinuclear complex [Ir(dbq-3FP)$_2$Cl]$_2$ (yield: 70%). It is to be noted that a microwave synthesis system (Discovery, manufactured by CEM Corporation) was used for the microwave irradiation. Synthetic scheme of Step 2 is shown in the following (b-2).

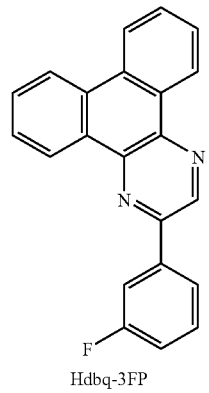

Hdbq-3FP (b-2)

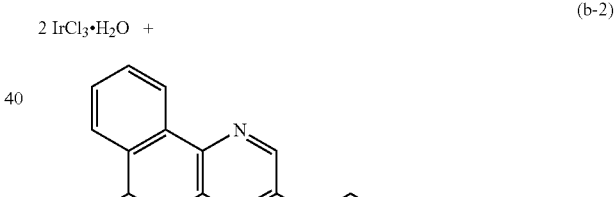

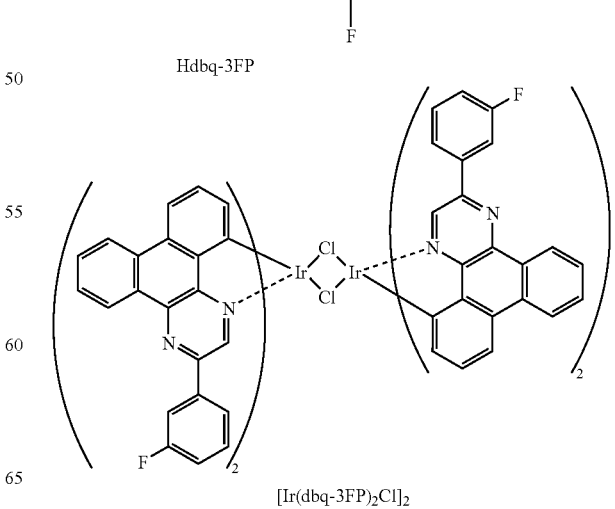

[Ir(dbq-3FP)$_2$Cl]$_2$

Step 3: Synthesis of (acetylacetonato)bis[2-(3-fluorophenyl)-dibenzo[f,h]quinoxalinato]iridium(III)

Abbreviation: Ir(dbq-3FP)₂(acac)

Subsequently to Step 2 described above, 20 mL of 2-ethoxyethanol, 2.06 g of the dinuclear complex [Ir(dbq-3FP)₂Cl]₂ that was obtained in Step 2, 0.43 g of sodium acetylacetonate hydrate (Na(CH₃COCHCOCH₃)·XH₂O) were put in an eggplant type flask with a reflux pipe. The atmosphere in the flask was substituted with argon. Then, the mixture was irradiated with a microwave (2.45 GHz, 100 W) for 30 minutes to be reacted. The reaction solution was filtered, and the obtained filtrate was condensed and dried to obtain a residue. This residue was dissolved in dichloromethane and filtered through celite, and then recrystallized with dichloromethane to obtain the organometallic complex of the present invention Ir(dbq-3FP)₂(acac) as a red powder (yield: 27%). Synthetic scheme of Step 3 is shown in the following (c-2).

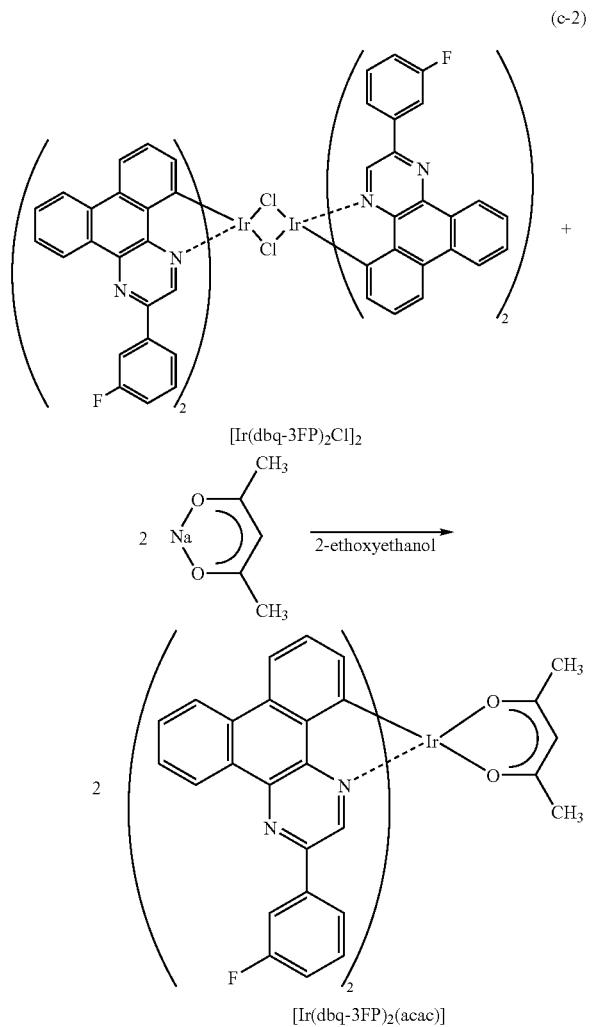

(c-2)

[Ir(dbq-3FP)₂Cl]₂

[Ir(dbq-3FP)₂(acac)]

Figure 23:
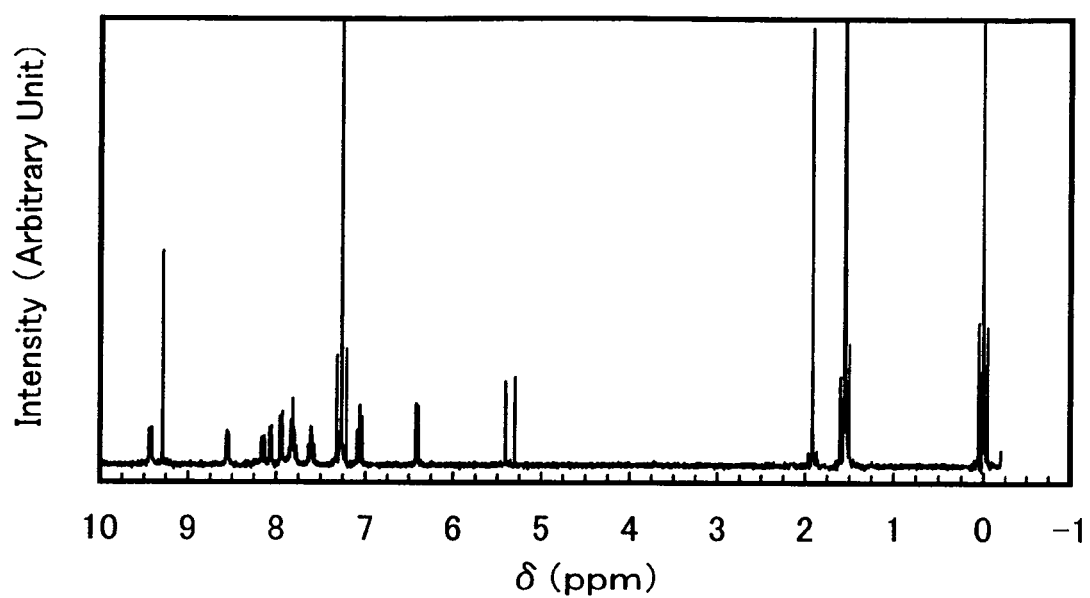
FIG. 23 is a $^1$H-NMR chart of (acetylacetonato)bis[2-(3-fluorophenyl)-dibenzo[f,h]quinoxalinato]iridium(III) which is synthesized in Example 2.

An analysis result of the red powder obtained in Step 3 by nuclear magnetic resonance spectrometry (¹H-NMR) is shown below. A ¹H-NMR chart is illustrated in FIG. 23. It is found that the organometallic complex of the present invention Ir(dbq-3FP)₂(acac) of the present invention, represented by the above structural formula (55), was obtained in Synthetic Example 2.

¹H-NMR. δ (CDCl₃): 1.92 (s, 6H), 5.41 (s, 1H), 6.41 (d, 2H), 7.06 (t, 2H), 7.60 (m, 2H), 7.81 (m, 6H), 7.94 (d, 2H), 8.06 (d, 2H), 8.15 (td, 2H), 8.57 (m, 2H), 9.29 (s, 1H), 9.44 (m, 2H).

Figure 24:
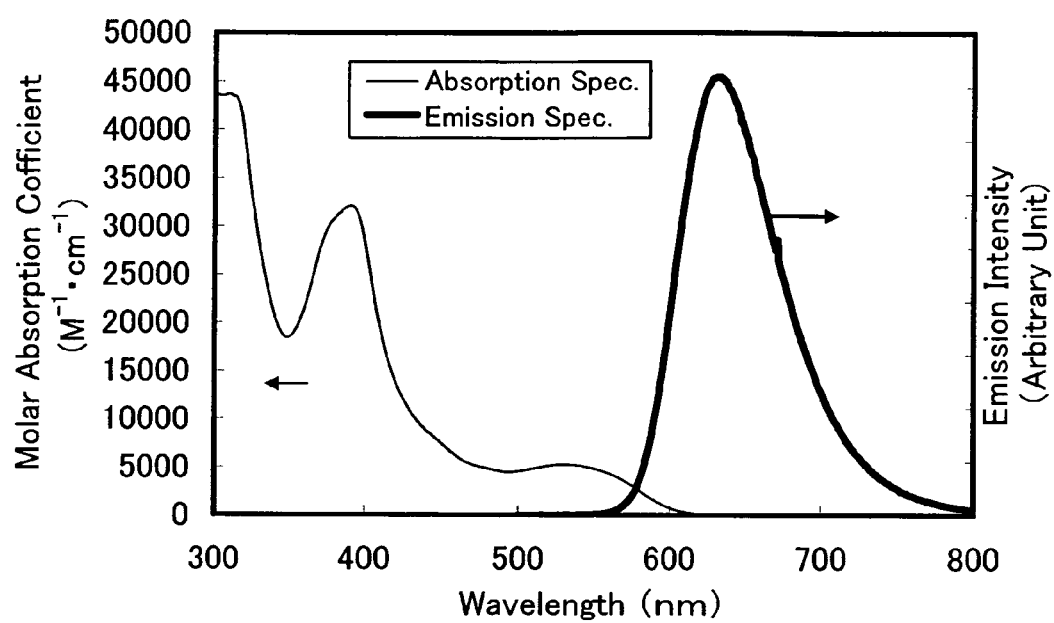
FIG. 24 is a graph illustrating an absorption spectrum and an emission spectrum of (acetylacetonato)bis[(2-(3-fluorophenyl)-dibenzo[f,h]quinoxalinato)iridium(III) which is synthesized in Example 2.

Next, an absorption spectrum of Ir(dbq-3FP)₂(acac) was measured with the use of an ultraviolet-visible light spectrophotometer (manufactured by Japan Spectroscopy Corporation, V550 type). The measurement was conducted by using a dichloromethane solution (0.093 mmol/L) at room temperature. Further, an emission spectrum of Ir(dbq-3FP)₂(acac) was measured with the use of a fluorescence spectrophotometer (manufactured by Hamamatsu Photonics Corporation, FS920). The measurement was conducted by using a degassed dichloromethane solution (0.33 mmol/L) at room temperature. FIG. 24 illustrates the measurement results. The horizontal axis indicates a wavelength and the vertical axis indicates a molar absorption coefficient and an emission intensity.

As illustrated in FIG. 24, the organometallic complex of the present invention Ir(dbq-3FP)₂(acac) of the present invention has a peak of emission spectrum at 633 nm, and red light was observed from the dichloromethane solution.

EXAMPLE 3

Synthetic Example 3

Synthetic Example 3 will specifically exemplify a synthetic example of bis(2-phenyldibenzo[f,h]quinoxalinato)(dipivaloylmethanato)iridium(III) (abbreviation: Ir(dbq-P)₂(dpm)) which is the organometallic complex of the present invention, represented by the structural formula (9) in Embodiment Mode 1.

First, 20 mL of 2-ethoxyethanol, 0.36 g of the dinuclear complex [Ir(dbq-P)₂Cl]₂ which was obtained in Step 2 of Synthetic Example 1, 0.13 mL of dipivaloylmethane, and 0.22 g of sodium carbonate were put in an eggplant type flask with a reflux pipe. The atmosphere in the flask was substituted with argon. Then, the mixture was irradiated with a microwave (2.45 GHz, 200 W) for 10 minutes to be reacted. The reaction solution was filtered, and the obtained filtrate was left for 15 hours to precipitate a solid. This solid was collected by filtration and then it was dissolved in dichloromethane to be recrystallized. Accordingly, the organometallic complex of the present invention Ir(dbq-P)₂(dpm) was obtained (red powder, yield 10%). Synthetic scheme is shown in the following (c-3).

(c-3)

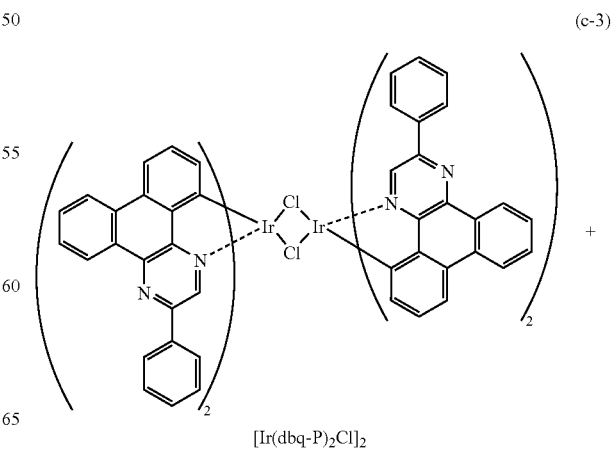

[Ir(dbq-P)₂Cl]₂

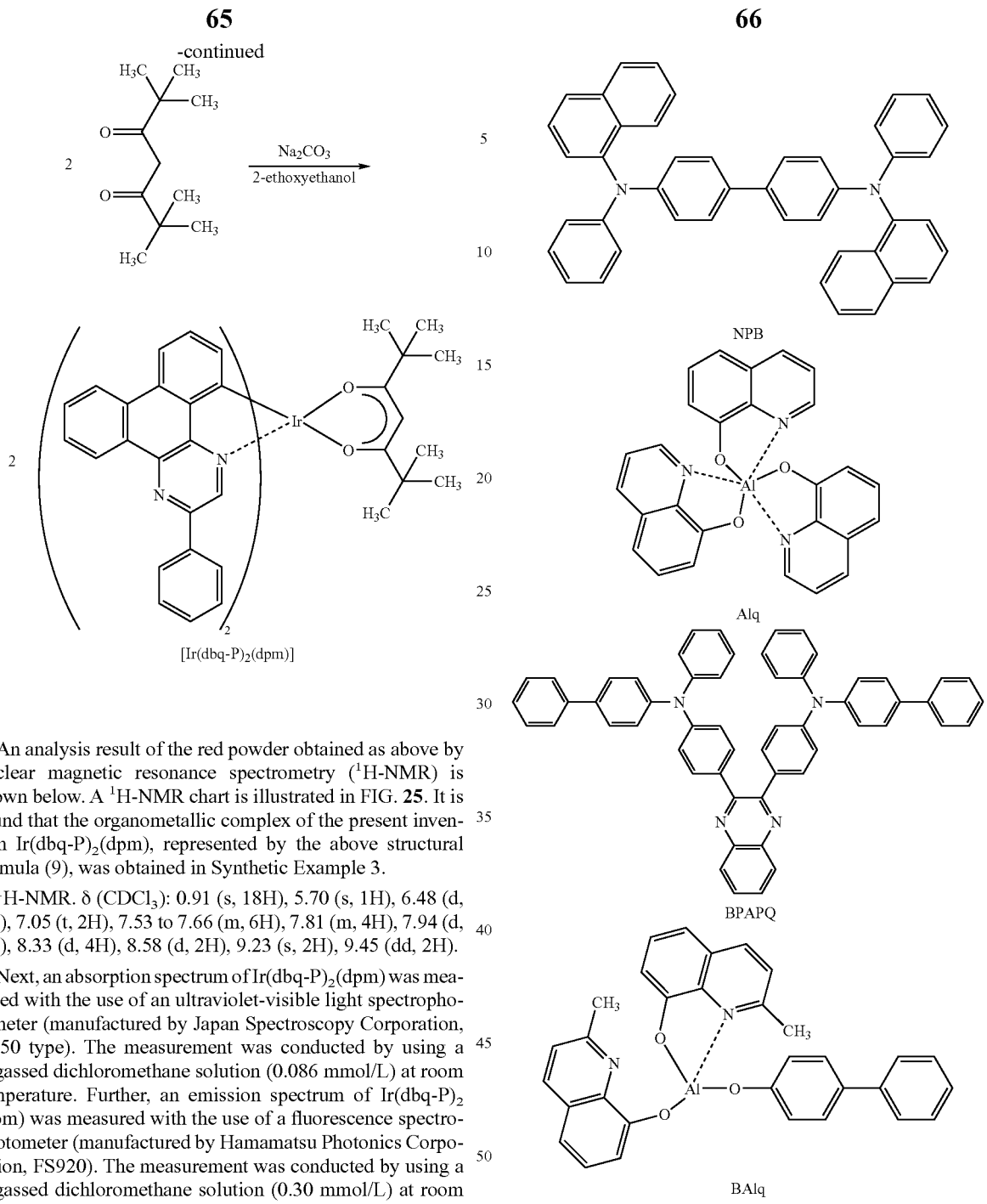

Figure 25:
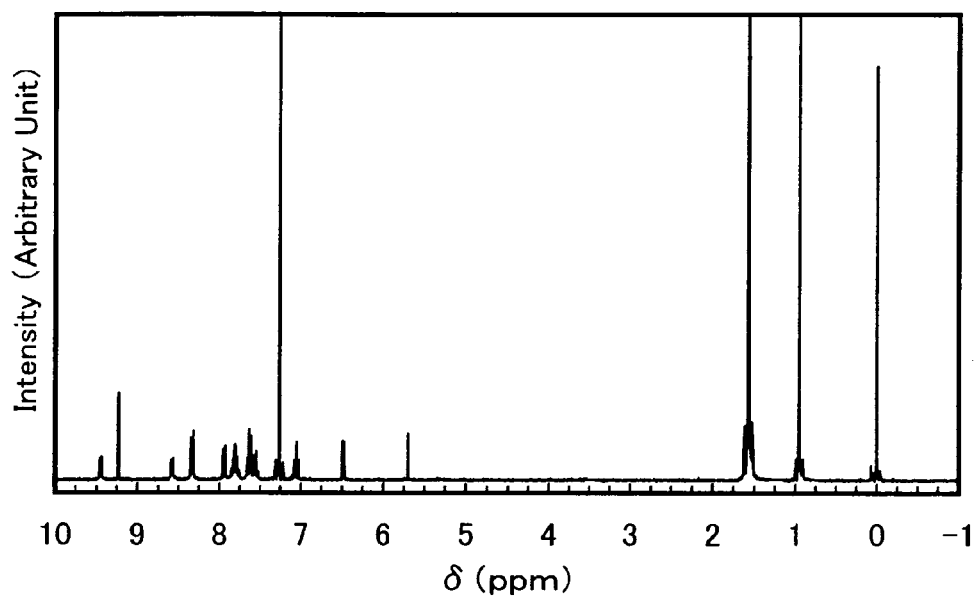
FIG. 25 is a $^1$H-NMR chart of bis(2-phenyldibenzo[f,h]quinoxalinato)(dipivaloylmethanato)iridium(III) which is synthesized in Example 3.

An analysis result of the red powder obtained as above by nuclear magnetic resonance spectrometry ($^1$H-NMR) is shown below. A $^1$H-NMR chart is illustrated in FIG. 25. It is found that the organometallic complex of the present invention Ir(dbq-P)$_2$(dpm), represented by the above structural formula (9), was obtained in Synthetic Example 3.

$^1$H-NMR. δ (CDCl$_3$): 0.91 (s, 18H), 5.70 (s, 1H), 6.48 (d, 2H), 7.05 (t, 2H), 7.53 to 7.66 (m, 6H), 7.81 (m, 4H), 7.94 (d, 2H), 8.33 (d, 4H), 8.58 (d, 2H), 9.23 (s, 2H), 9.45 (dd, 2H).

Figure 26:
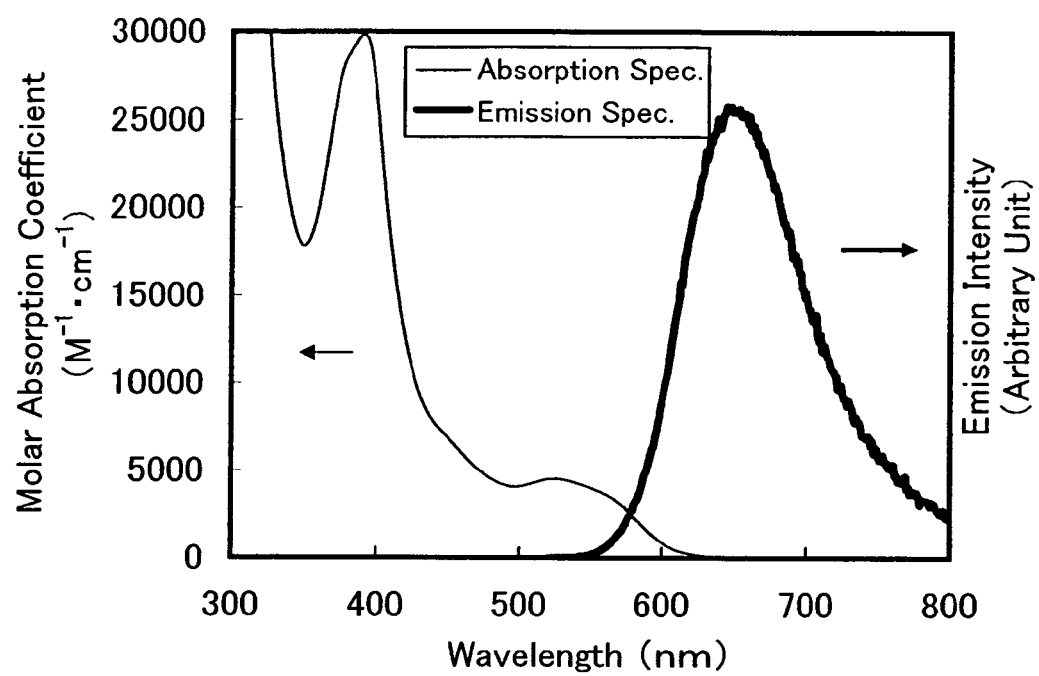
FIG. 26 is a graph illustrating an absorption spectrum and an emission spectrum of bis(2-phenyldibenzo[f,h]quinoxalinato)(dipivaloylmethanato)iridium(III) which is synthesized in Example 3.

Next, an absorption spectrum of Ir(dbq-P)$_2$(dpm) was measured with the use of an ultraviolet-visible light spectrophotometer (manufactured by Japan Spectroscopy Corporation, V550 type). The measurement was conducted by using a degassed dichloromethane solution (0.086 mmol/L) at room temperature. Further, an emission spectrum of Ir(dbq-P)$_2$(dpm) was measured with the use of a fluorescence spectrophotometer (manufactured by Hamamatsu Photonics Corporation, FS920). The measurement was conducted by using a degassed dichloromethane solution (0.30 mmol/L) at room temperature. FIG. 26 illustrates the measurement results. The horizontal axis indicates a wavelength and the vertical axis indicates a molar absorption coefficient and an emission intensity.

As illustrated in FIG. 26, the organometallic complex of the present invention Ir(dbq-P)$_2$(dpm) has a peak of emission spectrum at 650 nm, and red light was observed from the solution.

EXAMPLE 4

Figure 12:
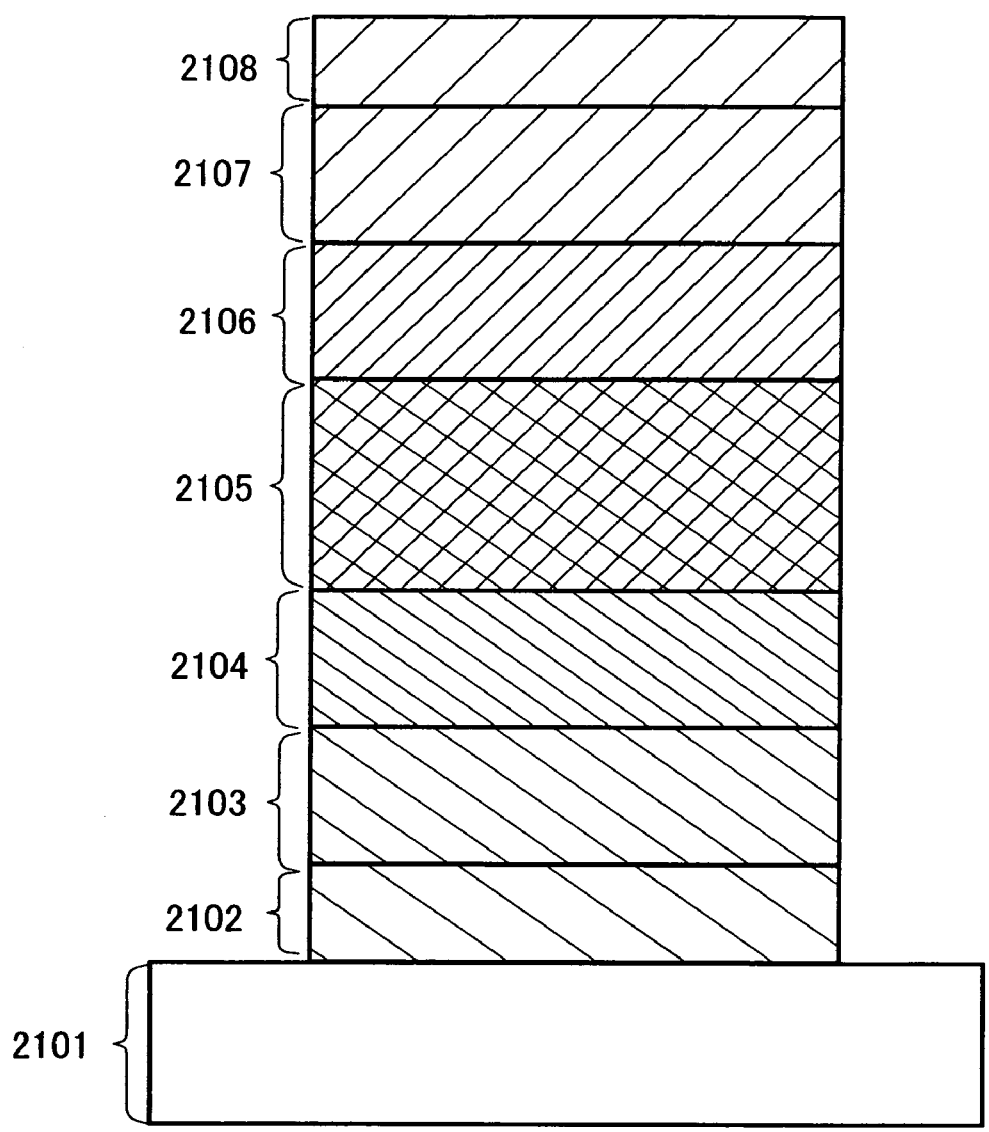
FIG. 12 is a view illustrating a light-emitting element of Examples.

Example 4 will describe the light-emitting element of the present invention with reference to FIG. 12. Chemical formulae of materials used in this example are shown below.

(Light-emitting Element 1)

First, a first electrode 2102 was formed using indium tin oxide containing silicon oxide over a glass substrate 2101 by sputtering. The film thickness of the first electrode 2102 was 110 nm and the area thereof was 2 mm×2 mm.

Next, the glass substrate 2101 provided with the first electrode 2102 was fixed on a substrate holder that was provided in a vacuum evaporation apparatus so that a surface provided with the first electrode 2102 faced downward. The pressure in the vacuum evaporation apparatus was reduced to approximately 10$^{-4}$ Pa. Then, a layer 2103 containing a composite material of an organic compound and an inorganic compound was formed on the first electrode 2102 by co-evaporation of NPB and molybdenum(VI)oxide. The film thickness was 50 nm and the weight ratio between NPB and molybdenum oxide was adjusted to be 4:1 (=NPB:molybdenum oxide). It is to be noted that the co-evaporation refers to an evaporation method by which evaporation is carried out simultaneously from a plurality of evaporation sources in one treatment chamber.

Next, a hole transporting layer 2104 was formed on the layer 2103 containing the composite material with a thickness of 10 nm using NPB by evaporation using resistance heating.

Further, a light-emitting layer 2105 was formed with a thickness of 30 nm on the hole transporting layer 2104 by co-evaporation of 2,3-bis{4-[N-(4-biphenyl)-N-phenylamino]phenyl}quinoxaline (abbreviation: BPAPQ) and Ir(dbq-P)$_2$(acac) which is represented by the structural formula (1). Here, the weight ratio between BPAPQ and Ir(dbq-P)$_2$(acac) was adjusted to be 1:0.06 (=BPAPQ:Ir(dbq-P)$_2$(acac)).

Then, an electron transporting layer 2106 was formed with a thickness of 10 nm on the light-emitting layer 2105 by evaporation using resistance heating by using bis(2-methyl-8-quinolinolato)(4-phenylphenolato)aluminum (abbreviation: BAlq).

Further, an electron injecting layer 2107 was formed with a thickness of 50 nm on the electron transporting layer 2106 by co-evaporation of tris(8-quinolinolato)aluminum (abbreviation: Alq) and lithium. The weight ratio between Alq and lithium was adjusted to be 1:0.01 (=Alq:lithium).

Lastly, a second electrode 2108 was formed with a thickness of 200 nm using aluminum on the electron injecting layer 2107 by evaporation using resistance heating. Thus, the light-emitting element 1 was manufactured.

Figure 13:
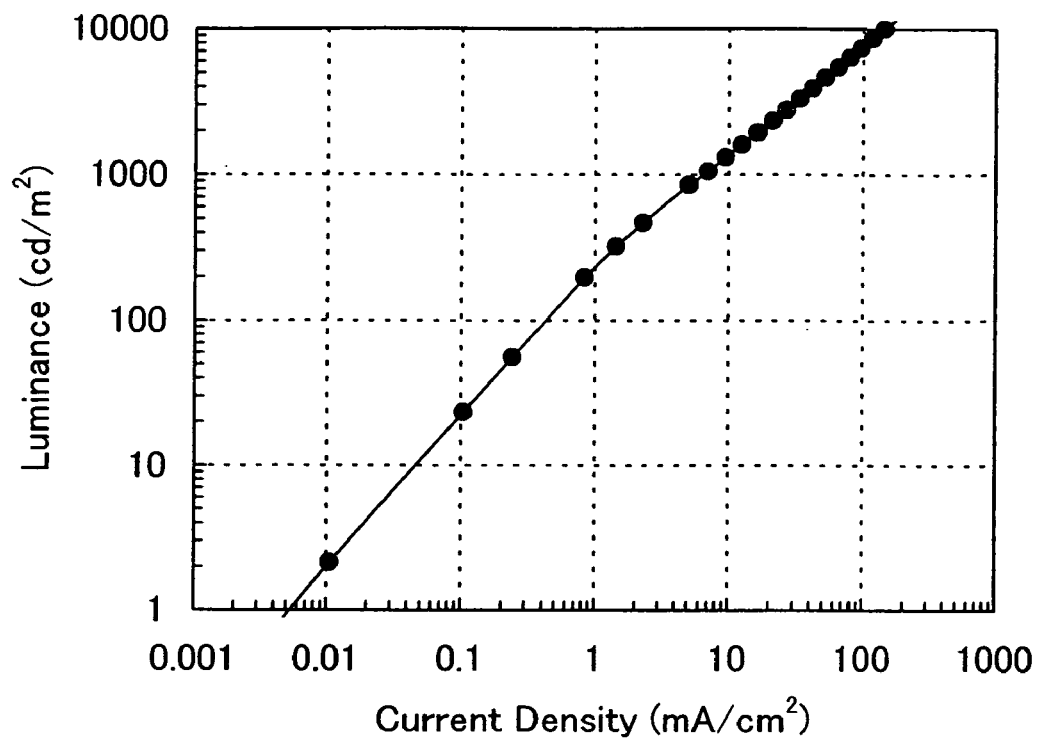
FIG. 13 is a graph illustrating current density-luminance characteristics of a light-emitting element manufactured in Example 4.
Figure 14:
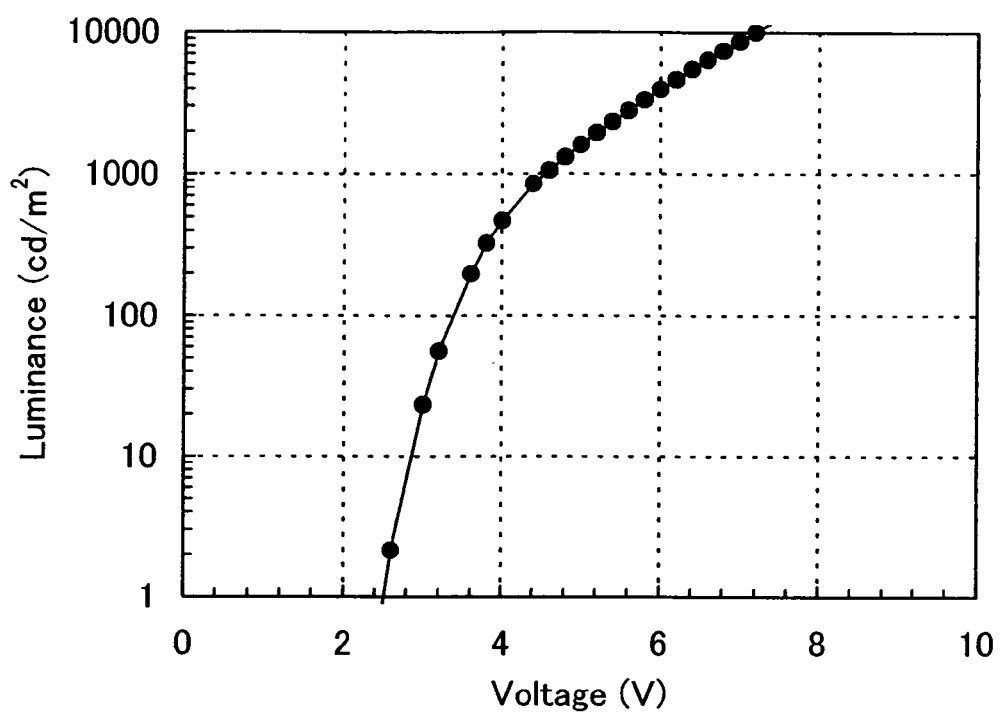
FIG. 14 is a graph illustrating voltage-luminance characteristics of a light-emitting element manufactured in Example 4.
Figure 15:
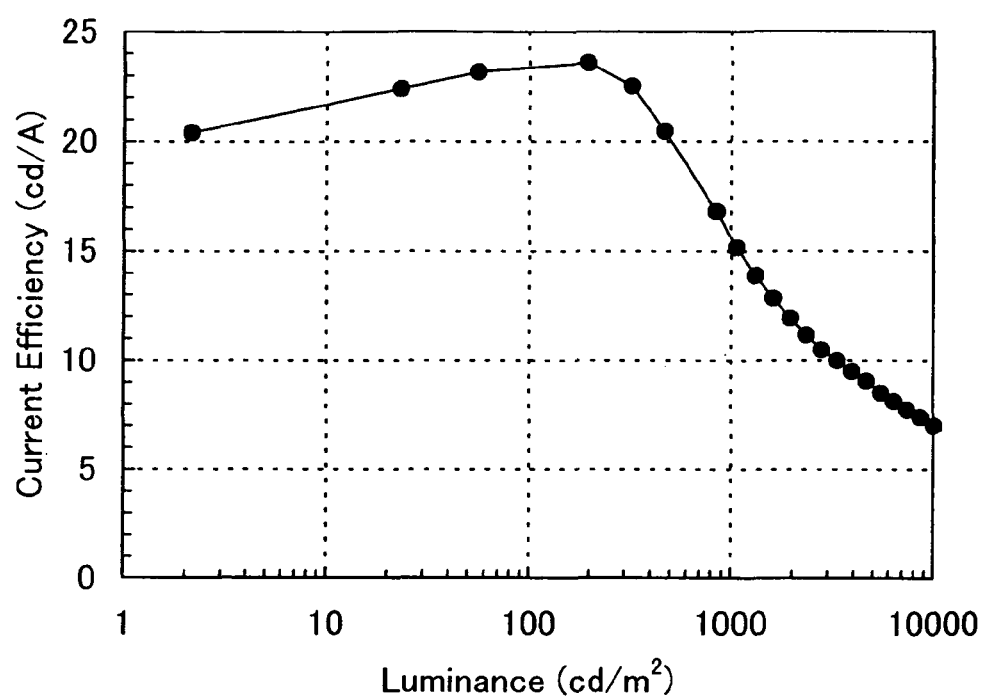
FIG. 15 is a graph illustrating luminance-current efficiency characteristics of a light-emitting element manufactured in Example 4.
Figure 16:
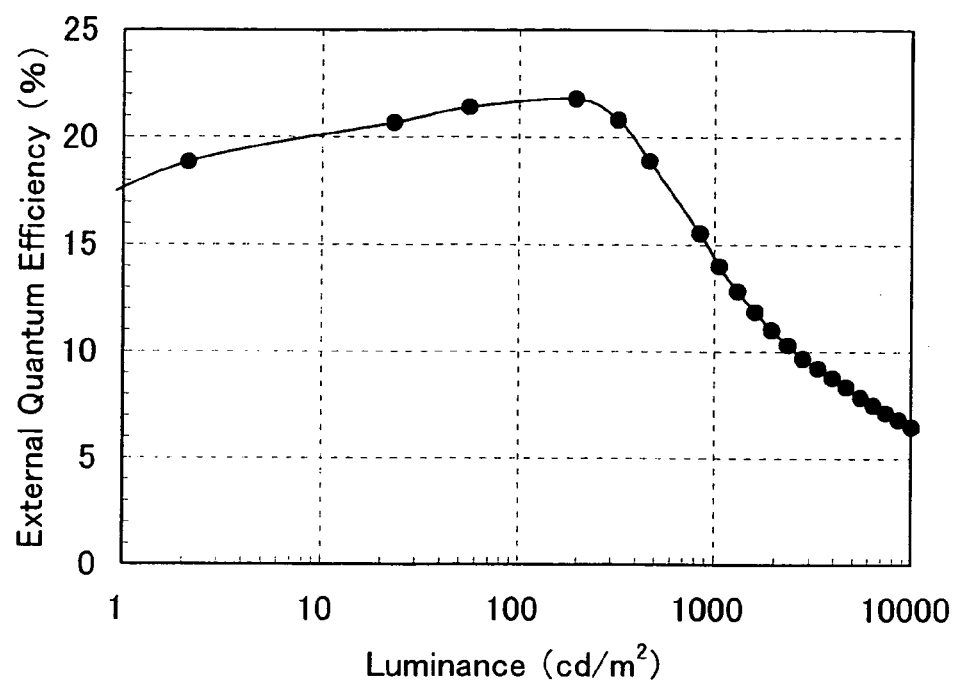
FIG. 16 is a graph illustrating luminance-external quantum efficiency characteristics of a light-emitting element manufactured in Example 4.
Figure 17:
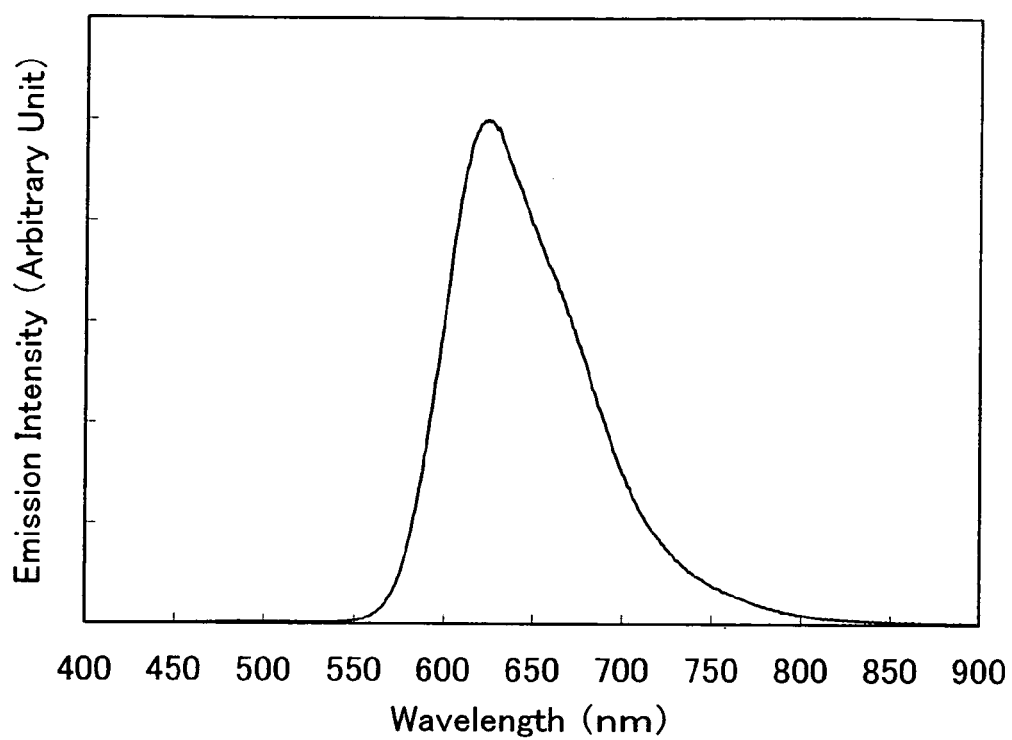
FIG. 17 is a graph illustrating an emission spectrum of a light-emitting element manufactured in Example 4.

FIG. 13 illustrates the current density-luminance characteristics of the light-emitting element 1. FIG. 14 illustrates the voltage-luminance characteristics thereof. FIG. 15 illustrates the luminance-current efficiency characteristics thereof. FIG. 16 illustrates the luminance-external quantum efficiency characteristics thereof. FIG. 17 illustrates an emission spectrum upon applying a current of 1 mA. From FIG. 17, it is found that light emission of the light-emitting element 1 corresponds to light emission of Ir(dbq-P)$_2$(acac). The CIE chromaticity coordinates of the light-emitting element 1 were (x, y)=(0.67, 0.33) when the luminance was 1000 cd/m$^2$, and the color of light emitted from the light-emitting element 1 corresponded to the red-color chromaticity defined by NTSC. Further, as found from FIG. 16, the external quantum efficiency of the light-emitting element 1 was as high as 14% when the luminance was 1000 cd/m$^2$. Therefore, the light-emitting element 1 has high emission efficiency. From FIG. 15, it is found that the current efficiency of the light-emitting element 1 was as high as 15 cd/A when the luminance was 1000 cd/m$^2$ and the light-emitting element 1 has high luminous efficiency. Further, from FIG. 14, the driving voltage of the light-emitting element 1 was 4.6 V when the luminance was 1000 cd/m$^2$, which shows that the voltage for obtaining a certain level of luminance is low. Therefore, it is found that the light-emitting element 1 has low power consumption.

An initial luminance was set at 1000 cd/m$^2$, and the light-emitting element 1 of this example was driven under a condition of a constant current density. After a lapse of 1000 hours, the light-emitting element 1 kept 86% of the initial luminance, which shows that the light-emitting element 1 hardly deteriorated.

Synthetic examples of the materials used in Example 4 will be described for reference.

<Synthetic Example of BPAPQ>

This synthetic example will specifically exemplify a synthetic example of BPAPQ.

Step 1: Synthesis of 2,3-bis(4-bromophenyl)quinoxaline

A chloroform solution (200 mL) of 30.0 g (81.5 mmol) of 4,4'-dibromobenzil and 9.00 g (83.2 mmol) of o-phenylenediamine was heated and refluxed at 80° C. for 3 hours under nitrogen atmosphere. The reaction solution was washed with water after being cooled to room temperature. An aqueous layer was extracted with chloroform. This extracted aqueous layer and an organic layer were put together and washed with a saturated saline solution. The organic layer was dried over magnesium sulfate and filtered. The filtrate was condensed to obtain 33 g (yield: 92%) of objective 2,3-bis(4-bromophenyl)quinoxaline as a white solid. Synthetic scheme of Step 1 is shown in the following (d-1).

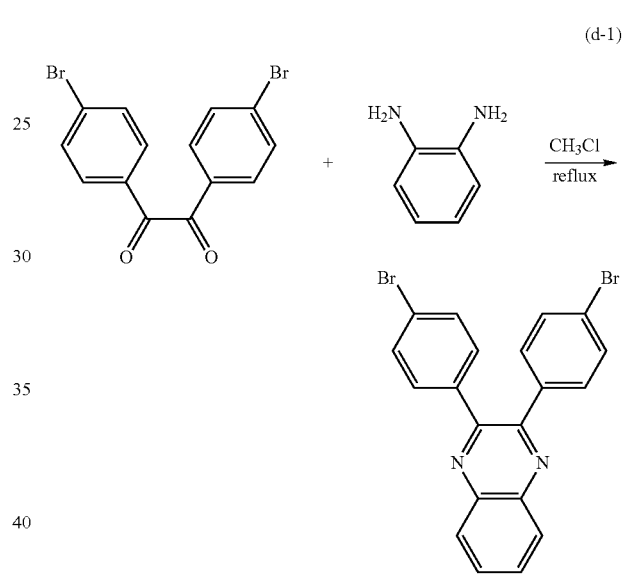

(d-1)

Step 2: Synthesis of N-(4-biphenyl)-N-phenylamine

To a xylene suspension (157 mL) containing 20.0 g (85.8 mmol) of 4-bromobiphenyl, 16.0 g (172 mmol) of aniline, 0.19 g (0.858 mmol) of palladium acetate, and 23.7 g (172 mmol) of potassium carbonate, 5.2 g (2.5 mmol) of tri-tert-butylphosphine (10% hexane solution) was added under nitrogen atmosphere. The mixture was refluxed at 120° C. for 10 hours. After completion of the reaction, the reaction mixture was washed with water to separate an organic layer and an aqueous layer. Then, the separated aqueous layer was extracted with toluene to separate an aqueous layer and a toluene layer. Next, the separated toluene layer and the organic layer, which had been separated from the aqueous layer after the washing of the reaction mixture with water, were put together, washed with a saturated saline solution, and dried over magnesium sulfate. The dried reaction solution was filtered, and the filtrate was condensed to obtain a residue. The residue was purified by silica gel chromatography (developing solvent: toluene) and then condensed. Accordingly, 13.5 g (yield: 64%) of N-(4-biphenyl)-N-phenylamine was obtained as a white solid. Synthetic scheme of Step 2 is shown in the following (d-2).

(d-2)

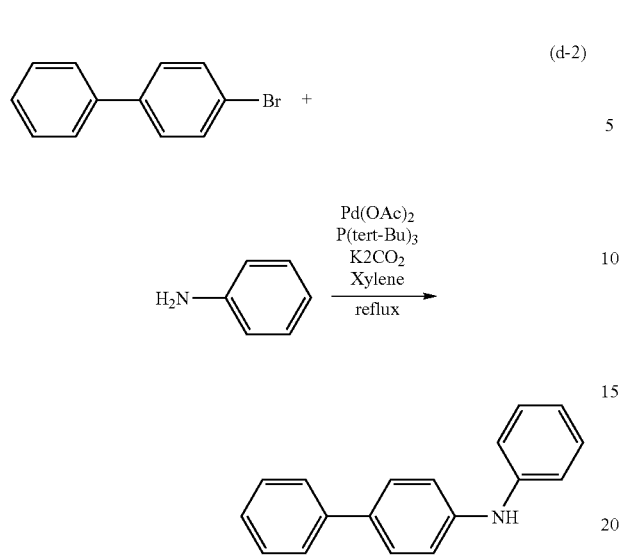

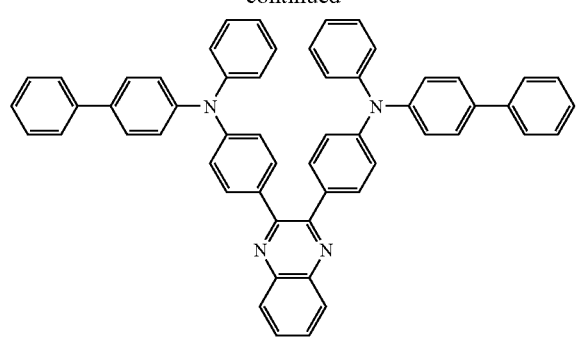

Step 3: Synthesis of BPAPQ 1.2 g (0.58 mmol) of tri-tert-butylphosphine (10% hexane solution) was added to a toluene suspension (80 mL) containing 5.0 g (11.4 mmol) of 2,3-bis(4-bromophenyl)quinoxaline, 6.1 g (25.0 mmol) of N-(4-biphenyl)-N-phenylamine, 0.33 g (0.58 mmol) of bis(dibenzylideneacetone)palladium, and 5.5 g (56.8 mmol) of sodium tert-butoxide under nitrogen atmosphere. The mixture was heated at 80° C. for 7 hours. After completion of the reaction, the reaction mixture was cooled to room temperature, and the precipitate was collected by filtration. The collected precipitate was again dissolved in toluene; this solution was filtered through celite, Florisil, and then alumina, and the filtrate was condensed. The residue was recrystallized with chloroform and hexane to obtain 8.1 g (yield: 78%) of BPAPQ as a yellow solid. Synthetic scheme of Step 3 is shown in the following (d-3).

(d-3)

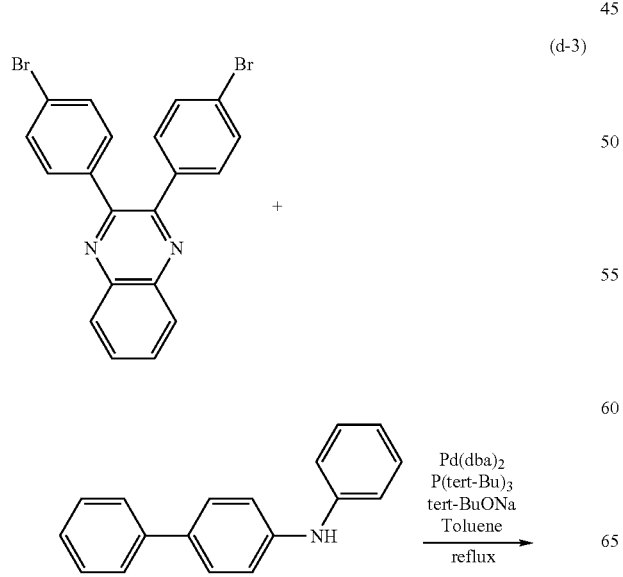

EXAMPLE 5

This example will describe the light-emitting element of the present invention with reference to FIG. 12. Chemical formulae of materials used in this example are described below.

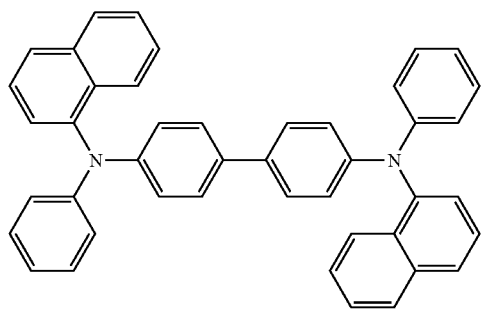

NPB

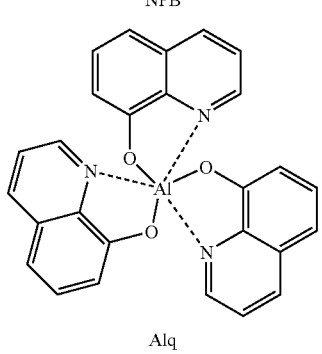

Alq

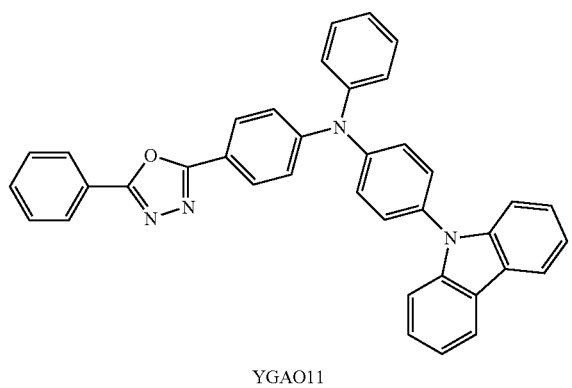

YGAO11

-continued

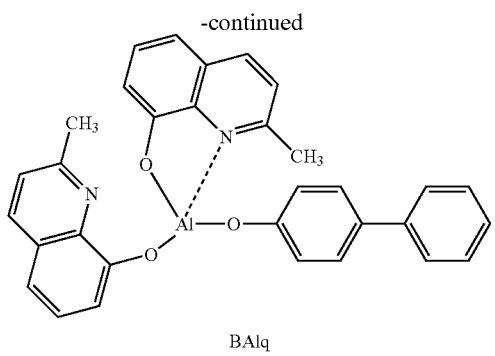

BAlq (Light-emitting Element 2)

First, the first electrode 2102 was formed using indium tin oxide containing silicon oxide over the glass substrate 2101 by sputtering. The film thickness of the first electrode 2102 was 110 nm and the area thereof was 2 mm×2 mm Then, the glass substrate 2101 provided with the first electrode 2102 was fixed on a substrate holder that was provided in a vacuum evaporation apparatus, in such a way that a surface provided with the first electrode 2102 should face downward. Then, the pressure in the vacuum evaporation apparatus was reduced to approximately $10^{-4}$ Pa. Then, the layer 2103 containing a composite material of an organic compound and an inorganic compound was formed on the first electrode 2102 by co-evaporation of NPB and molybdenum(VI)oxide. The film thickness was 50 nm and the weight ratio between NPB and molybdenum oxide was adjusted to be 4:1 (=NPB:molybdenum oxide). It is to be noted that the co-evaporation refers to an evaporation method by which evaporation is carried out simultaneously from a plurality of evaporation sources in one treatment chamber.

Next, the hole transporting layer 2104 was formed with a thickness of 10 nm using NPB on the layer 2103 containing the composite material by evaporation using resistance heating.

Further, the light-emitting layer 2105 was formed with a thickness of 30 nm on the hole transporting layer 2104 by co-evaporation of 2-(4-{N-[4-(carbazol-9-yl)phenyl]-N-phenylamino}phenyl)-5-phenyl-1,3,4-oxadiazole (abbreviation: YGAO11) and (acetylacetonato)bis(2-phenyldibenzo[f, h]quinoxalinato)iridium(III) (abbreviation: Ir(dbq-P)$_2$(acac)) which is represented by the structural formula (I). Here, the weight ratio between YGAO11 and Ir(dbq)$_2$(acac) was adjusted to be 1:0.06 (=YGAO11:Ir(dbq-P)$_2$(acac)).

Thereafter, the electron transporting layer 2106 was formed with a thickness of 10 nm using BAlq on the light-emitting layer 2105 by evaporation using resistance heating.

Further, the electron injecting layer 2107 was formed with a thickness of 50 nm on the electron transporting layer 2106 by co-evaporation of Alq and lithium. The weight ratio between Alq and lithium was adjusted to be 1:0.01 (=Alq:lithium).

Lastly, the second electrode 2108 was formed with a thickness of 200 nm using aluminum on the electron injecting layer 2107 by evaporation using resistance heating. Thus, the light-emitting element 2 was manufactured.

Figure 18:
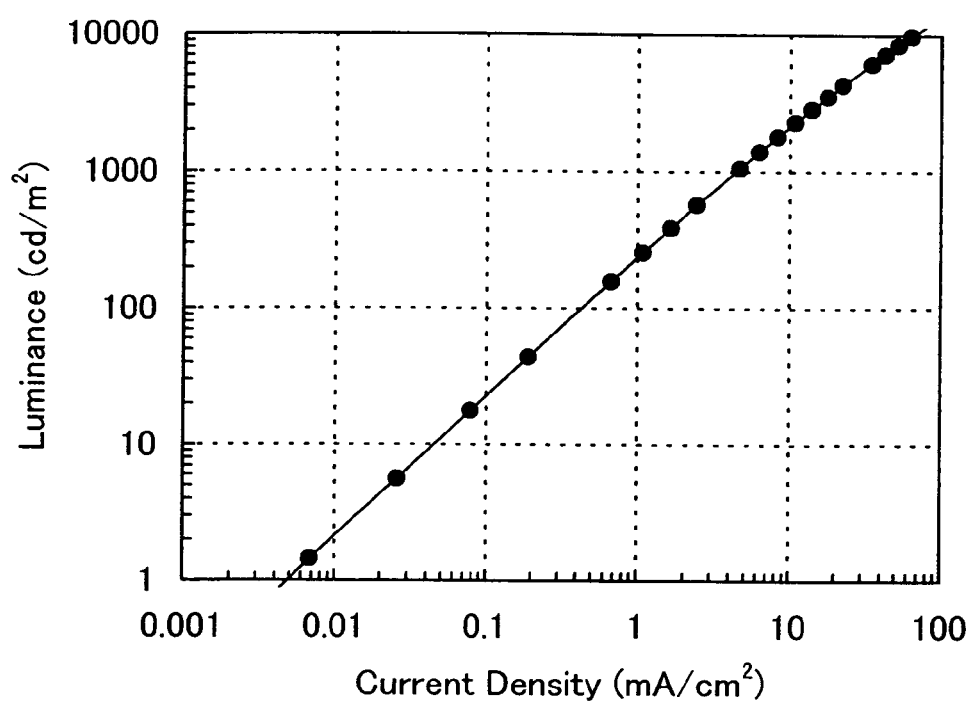
FIG. 18 is a graph illustrating current density-luminance characteristics of a light-emitting element manufactured in Example 5.
Figure 19:
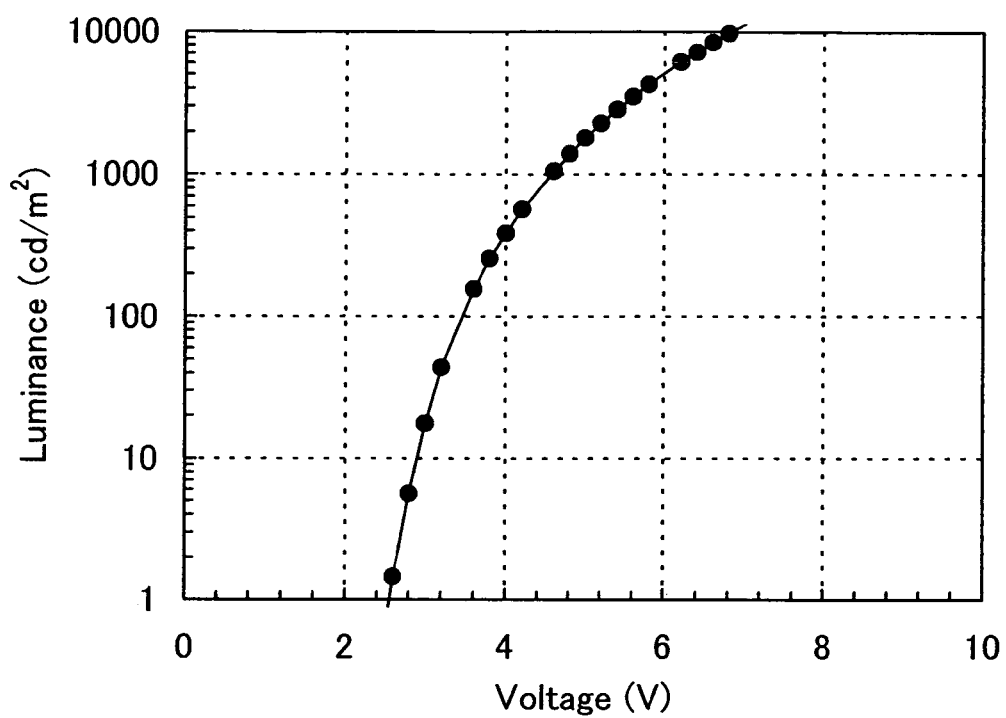
FIG. 19 is a graph illustrating voltage-luminance characteristics of a light-emitting element manufactured in Example 5.
Figure 20:
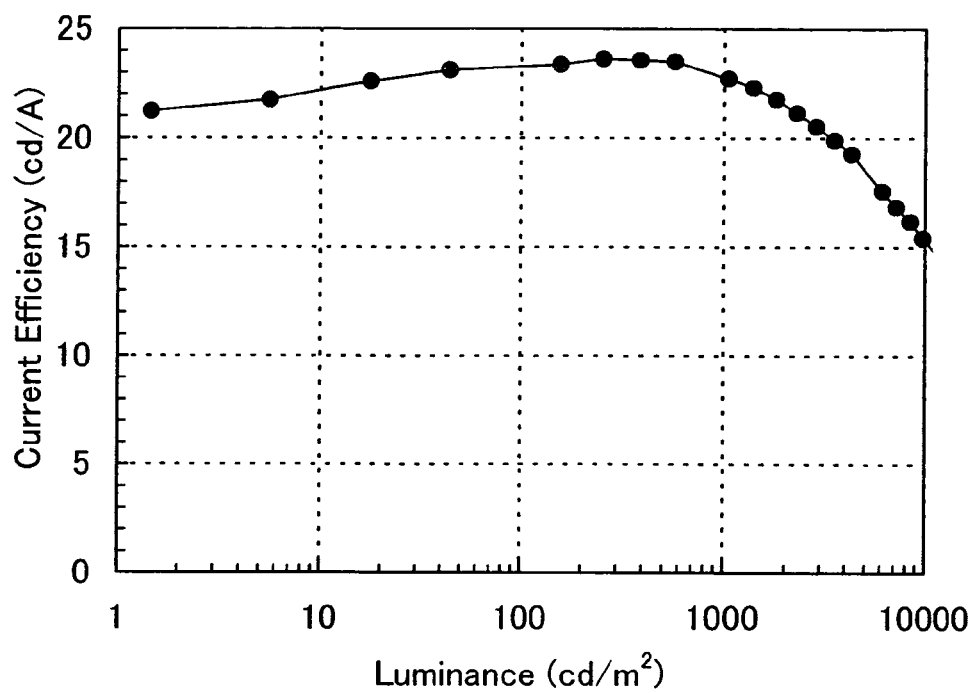
FIG. 20 is a graph illustrating luminance-current efficiency characteristics of a light-emitting element manufactured in Example 5.
Figure 21:
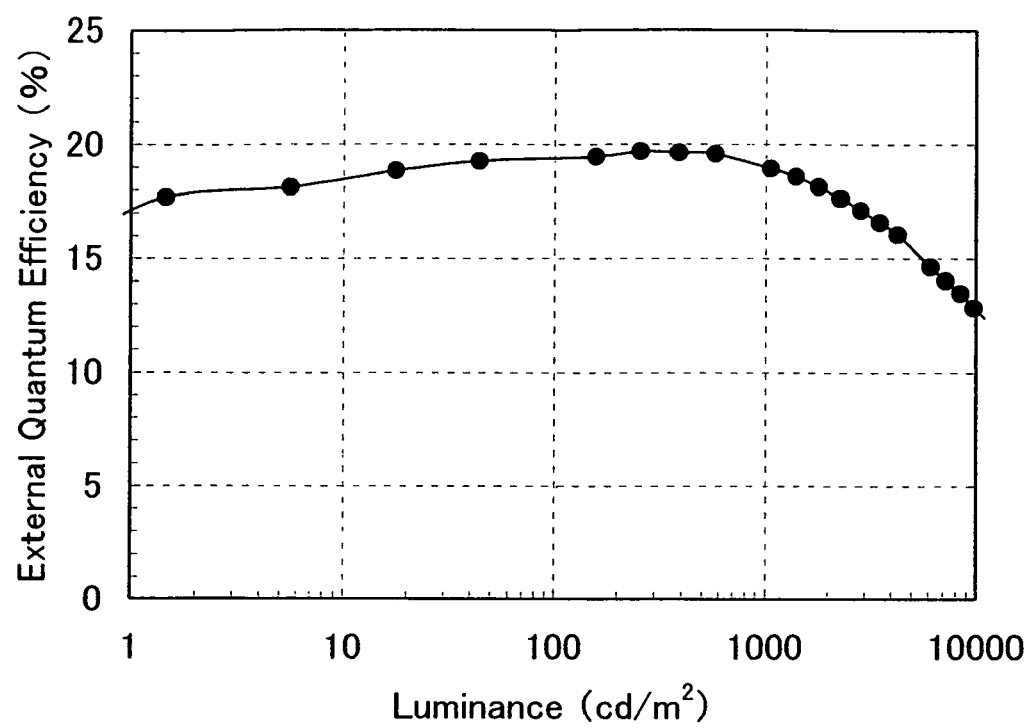
FIG. 21 is a graph illustrating luminance-external quantum efficiency of a light-emitting element manufactured in Example 5.
Figure 22:
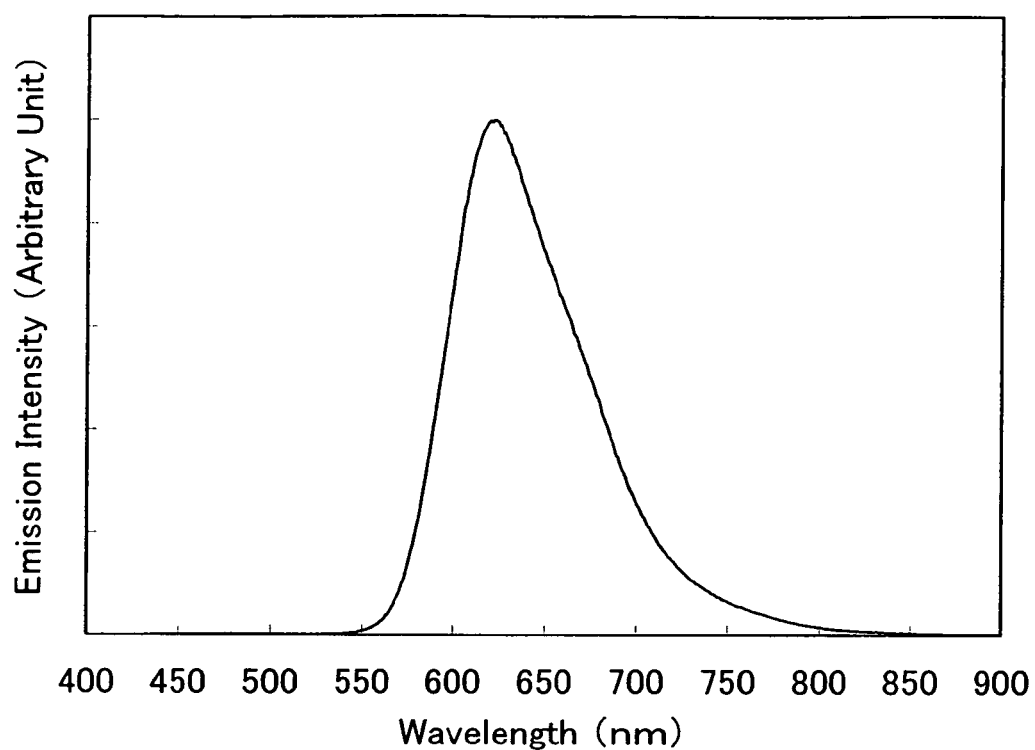
FIG. 22 is a graph illustrating an emission spectrum of a light-emitting element manufactured in Example 5.

FIG. 18 illustrates the current density-luminance characteristics of the light-emitting element 2. FIG. 19 illustrates the voltage-luminance characteristics thereof. FIG. 20 illustrates the luminance-current efficiency characteristics thereof. FIG. 21 illustrates the luminance-external quantum efficiency characteristics thereof. FIG. 22 illustrates an emission spectrum upon applying a current of 1 mA. From FIG. 22, it is found that light emission of the light-emitting element 2 corresponds to light emission of Ir(dbq-P)$_2$(acac). The CIE chromaticity coordinates of the light-emitting element 2 were (x, y)=(0.66, 0.34) when the luminance was 1000 cd/m$^2$, and the color of light emitted from the light-emitting element 2 corresponded to the red-color chromaticity defined by NTSC. Further, as found from FIG. 21, the external quantum efficiency of the light-emitting element 2 was as high as 19% when the luminance was 1000 cd/m$^2$. Therefore, the light-emitting element 2 has high emission efficiency. From FIG. 20, it is found that the current efficiency of the light-emitting element 2 was as high as 23 cd/A when the luminance was 1000 cd/m$^2$. Further, from FIG. 19, it is found that the driving voltage of the light-emitting element 2 was 4.6 V when the luminance was 1000 cd/m$^2$, which shows that the voltage for obtaining a certain level of luminance is low. Therefore, it is found that the light-emitting element 2 has low power consumption.

A synthetic example of the materials used in Example 5 will be described for reference.

<Synthetic Example of YGAO11>

This synthetic example describes a synthetic method of YGAO11.

To a toluene solution (45 mL) of 3.0 g (10.0 mmol) of 2-(4-bromophenyl)-5-phenyl-1,3,4-oxadiazole, 3.4 g (10.0 mmol) of 9-(4-[N-phenylamino]phenyl)carbazole, and 1.9 g (19.9 mmol) of sodium tert-butoxide, 0.3 mL of tri-tert-butylphosphine (10% hexane solution) and 0.3 g (0.6 mmol) of bis(dibenzylideneacetone)palladium(0) were added under nitrogen atmosphere. The mixture was heated at 120° C. for 5 hours. After completion of the reaction, the reaction solution was cooled to room temperature and filtered through celite. The filtrate was washed with water and dried over magnesium sulfate. The dried reaction solution was filtered and the filtrate was condensed to obtain a solid. The solid was dissolved in toluene and then purified by silica column chromatography (developing solvent:toluene and then toluene:ethyl acetate=1:1). The solution containing the purified substance was condensed. The resultant substance was recrystallized with chloroform and hexane to obtain 4.7 g (yield: 85%) of YGAO11 as a light yellow solid. Synthetic scheme is shown in the following (e-1).

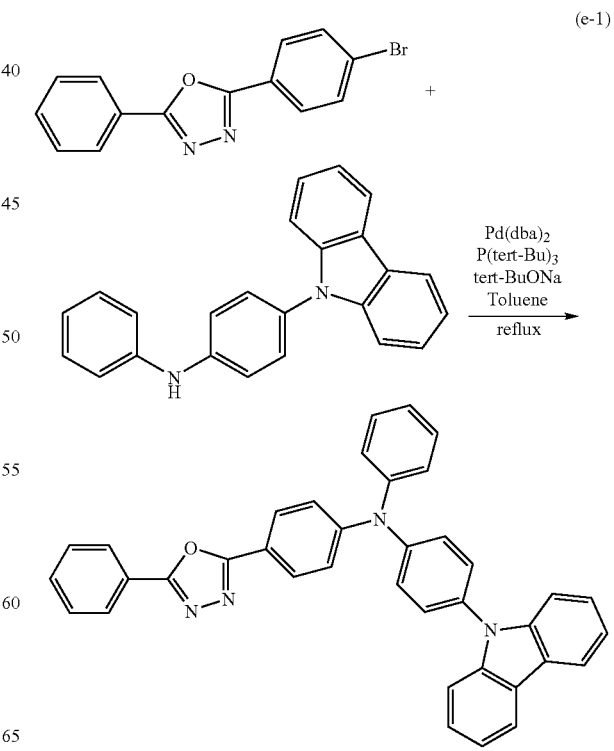

(e-1)

This application is based on Japanese Patent Application serial no. 2006-350895 and no. 2007-299175 which are filed with Japan Patent Office on Dec. 27, 2006 and Nov. 19, 2007, respectively, the entire contents of which are hereby incorporated by reference.

What is claimed is:

1. An organometallic complex having a structure represented by a general formula (G1),

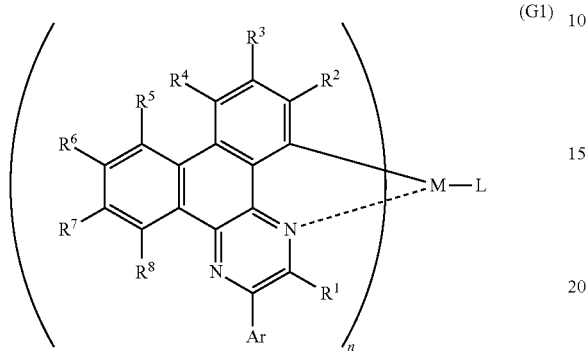

(G1)

wherein Ar represents an aryl group having 6 to 25 carbon atoms;

$R^1$ represents any one of hydrogen, an alkyl group having 1 to 4 carbon atoms, and an alkoxy group having 1 to 4 carbon atoms;

$R^2$ to $R^8$ each represent any one of hydrogen, an alkyl group having 1 to 4 carbon atoms, an alkoxy group having 1 to 4 carbon atoms, and a halogen element;

M represents a metal selected from Group 9 elements and Group 10 elements;

L represents a monoanionic ligand; and n is 2 when the metal is a Group 9 element, and n is 1 when the metal is a Group 10 element.

2. The organometallic complex according to claim 1, wherein the monoanionic ligand is any one of a monoanionic bidentate chelate ligand having a β-diketone structure, a monoanionic bidentate chelate ligand having a carboxyl group, a monoanionic bidentate chelate ligand having a phenolic hydroxyl group, and a monoanionic bidentate chelate ligand in which two ligand elements are both nitrogen.

3. The organometallic complex according to claim 1, wherein the monoanionic ligand is any one of monoanionic ligands represented by the following structural formulae (L1) to (L9):

(L1)

(L2)

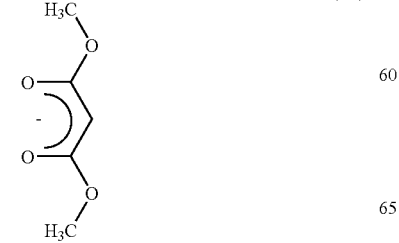

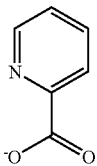

(L3)

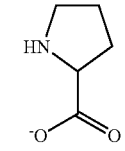

(L4)

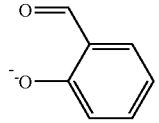

(L5)

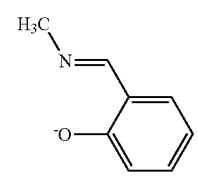

(L6)

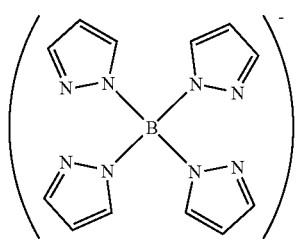

(L7)

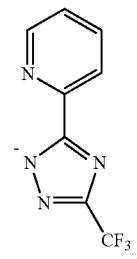

(L8)

(L9)

4. The organometallic complex according to claim 1, wherein the metal is iridium or platinum.

5. A light-emitting element comprising the organometallic complex according to claim 1.

6. A lighting device comprising the light-emitting element according to claim 5.

7. A light-emitting device comprising a light-emitting element including the organometallic complex according to claim 1.

8. An electronic device comprising a display portion, wherein the display portion includes the light-emitting device according to claim 7.

9. An organometallic complex having a structure represented by a general formula (G2),

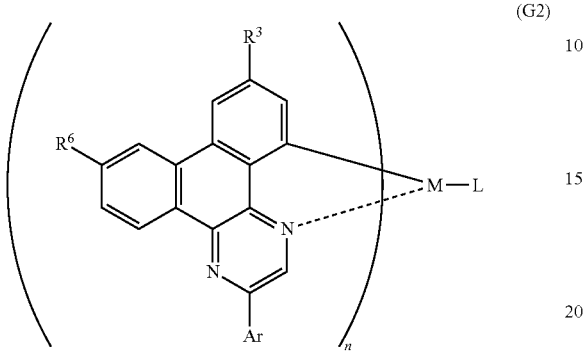

(G2)

wherein Ar represents an aryl group having 6 to 25 carbon atoms;

$R^3$ and $R^6$ each represent any one of hydrogen, an alkyl group having 1 to 4 carbon atoms, an alkoxy group having 1 to 4 carbon atoms, and a halogen element;

M represents a metal selected from Group 9 elements and Group 10 elements;

L represents a monoanionic ligand; and n is 2 when the metal is a Group 9 element, and n is 1 when the metal is a Group 10 element.

10. The organometallic complex according to claim 9, wherein the monoanionic ligand is any one of a monoanionic bidentate chelate ligand having a β-diketone structure, a monoanionic bidentate chelate ligand having a carboxyl group, a monoanionic bidentate chelate ligand having a phenolic hydroxyl group, and a monoanionic bidentate chelate ligand in which two ligand elements are both nitrogen.

11. The organometallic complex according to claim 9, wherein the monoanionic ligand is any one of monoanionic ligands represented by the following structural formulae (L1) to (L9):

(L1)

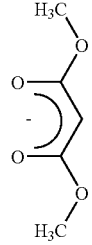

(L2)

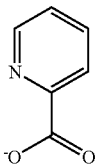

(L3)

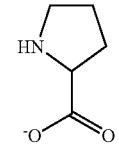

(L4)

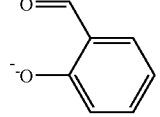

(L5)

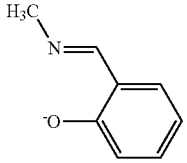

(L6)

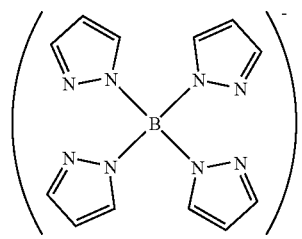

(L7)

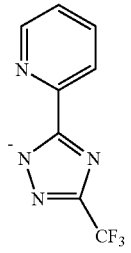

(L8)

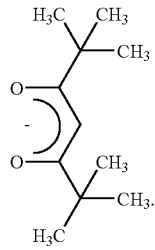

(L9)

12. The organometallic complex according to claim 9, wherein the metal is iridium or platinum.

13. A light-emitting element comprising the organometallic complex according to claim 9.

14. A lighting device comprising the light-emitting element according to claim 13.

15. A light-emitting device comprising a light-emitting element including the organometallic complex according to claim 9.

16. An electronic device comprising a display portion, wherein the display portion includes the light-emitting device according to claim 15.

17. The organometallic complex according to claim 9, wherein $R^3$ and $R^6$ each are hydrogen.

18. An organometallic complex having a structure represented by a general formula (G4),

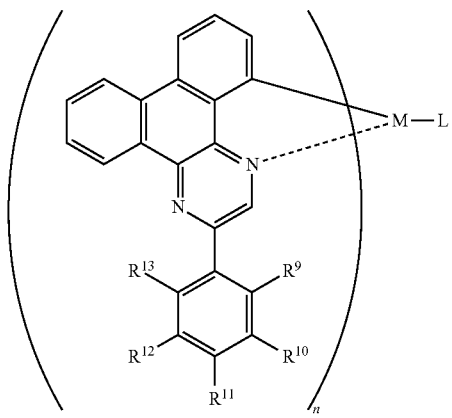
(G4)

wherein $R^9$ to $R^{13}$ each represent any one of hydrogen, an alkyl group having 1 to 4 carbon atoms, an alkoxy group having 1 to 4 carbon atoms, an aryl group having 6 to 12 carbon atoms, and a halogen element;

M represents a metal selected from Group 9 elements and Group 10 elements;

L represents a monoanionic ligand; and n is 2 when the metal is a Group 9 element, and n is 1 when the metal is a Group 10 element.

19. The organometallic complex according to claim 18, wherein the monoanionic ligand is any one of a monoanionic bidentate chelate ligand having a β-diketone structure, a monoanionic bidentate chelate ligand having a carboxyl group, a monoanionic bidentate chelate ligand having a phenolic hydroxyl group, and a monoanionic bidentate chelate ligand in which two ligand elements are both nitrogen.

20. The organometallic complex according to claim 18, wherein the monoanionic ligand is any one of monoanionic ligands represented by the following structural formulae (L1) to (L9):

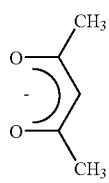
(L1)

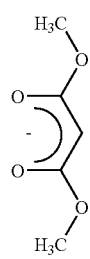
(L2)

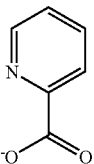
(L3)

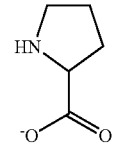
(L4)

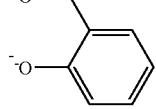
(L5)

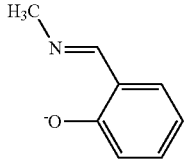
(L6)

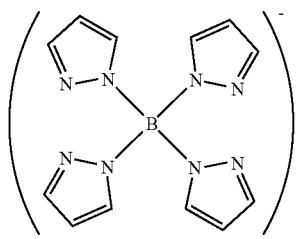
(L7)

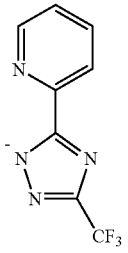
(L8)

(L9)

21. The organometallic complex according to claim 18, wherein the metal is iridium or platinum.

22. A light-emitting element comprising the organometallic complex according to claim 18.

23. A lighting device comprising the light-emitting element according to claim 22.

24. A light-emitting device comprising a light-emitting element including the organometallic complex according to claim 18.

25. An electronic device comprising a display portion, wherein the display portion includes the light-emitting device according to claim 24.

26. The organometallic complex according to claim 1, wherein the monoanionic ligand is bidentate and has a β-diketone structure, a carboxyl group, or a phenolic hydroxyl group.

27. The organometallic complex according to claim 9, wherein the monoanionic ligand is bidentate and has a β-diketone structure, a carboxyl group, or a phenolic hydroxyl group.

28. The organometallic complex according to claim 18, wherein the monoanionic ligand is bidentate and has a β-diketone structure, a carboxyl group, or a phenolic hydroxyl group.

29. The organometallic complex according to claim 1, wherein the monoanionic ligand is any one of monoanionic ligands represented by the following structural formulae:

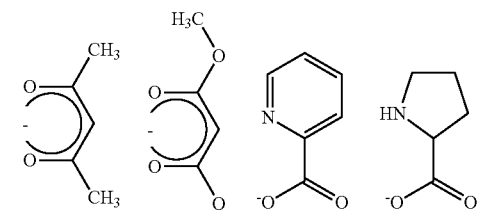

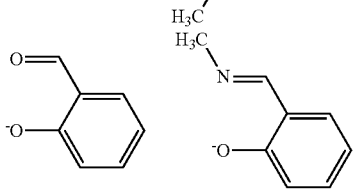

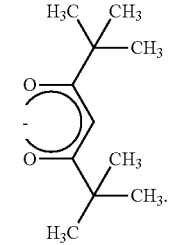

30. The organometallic complex according to claim 9, wherein the monoanionic ligand is any one of monoanionic ligands represented by the following structural formulae:

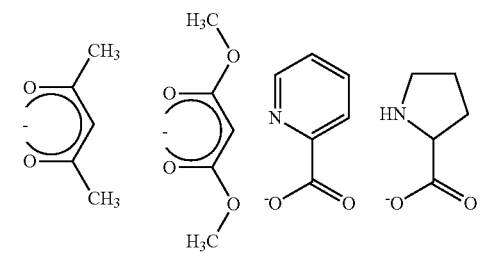

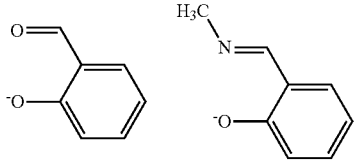

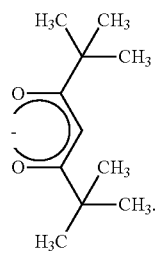

31. The organometallic complex according to claim 18, wherein the monoanionic ligand is any one of monoanionic ligands represented by the following structural formulae:

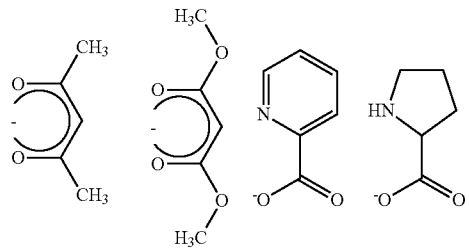

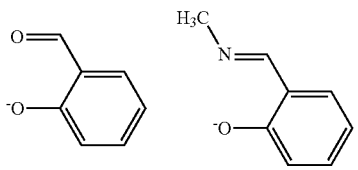

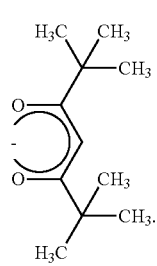

* * * * *